United States Patent
Irvine et al.

(10) Patent No.: US 12,018,315 B2
(45) Date of Patent: *Jun. 25, 2024

(54) PEPTIDE NUCLEIC ACID FUNCTIONALIZED HYDROGEL MICRONEEDLES FOR SAMPLING AND DETECTION OF INTERSTITIAL FLUID NUCLEIC ACIDS

(71) Applicants: Massachusetts Institute of Technology, Cambridge, MA (US); Imperial College Innovations Limited, London (GB)

(72) Inventors: Darrell J. Irvine, Arlington, MA (US); Jason Y. H. Chang, Cambridge, MA (US); Sylvain Ladame, Tring (GB); Dana Al Sulaiman, London (GB)

(73) Assignees: Massachusetts Institute of Technology, Cambridge, MA (US); Imperial College Innovations Limited, London (GB)

( * ) Notice: Subject to any disclaimer, the term of this patent is extended or adjusted under 35 U.S.C. 154(b) by 67 days.

This patent is subject to a terminal disclaimer.

(21) Appl. No.: 16/887,649

(22) Filed: May 29, 2020

(65) Prior Publication Data

US 2020/0377929 A1    Dec. 3, 2020

Related U.S. Application Data

(60) Provisional application No. 62/854,475, filed on May 30, 2019.

(51) Int. Cl.
| | |
|---|---|
| *C12Q 1/6806* | (2018.01) |
| *C12M 1/34* | (2006.01) |
| *C12Q 1/6823* | (2018.01) |
| *G01N 21/64* | (2006.01) |

(52) U.S. Cl.
CPC ......... *C12Q 1/6806* (2013.01); *C12M 41/36* (2013.01); *C12Q 1/6823* (2013.01); *G01N 21/6428* (2013.01); *C12Q 2565/1025* (2013.01); *C12Q 2565/629* (2013.01)

(58) Field of Classification Search
CPC combination set(s) only.
See application file for complete search history.

(56) References Cited

U.S. PATENT DOCUMENTS

| | | |
|---|---|---|
| 3,266,987 A | 8/1966 | Crowley et al. |
| 3,710,795 A | 1/1973 | Higuchi et al. |
| 3,962,414 A | 6/1976 | Michaels |
| 4,191,811 A | 3/1980 | Hodgdon |
| 4,250,029 A | 2/1981 | Kiser et al. |
| 4,460,563 A | 7/1984 | Calanchi |
| 4,638,045 A | 1/1987 | Kohn et al. |
| 4,794,000 A | 12/1988 | Ecanow |
| 4,806,355 A | 2/1989 | Goosen et al. |
| 4,806,621 A | 2/1989 | Kohn et al. |
| 4,946,929 A | 8/1990 | D'Amore et al. |
| 5,010,167 A | 4/1991 | Ron et al. |
| 5,015,476 A | 5/1991 | Cochrum et al. |
| 5,019,379 A | 5/1991 | Domb et al. |
| 5,093,489 A | 3/1992 | Diamantoglou |
| 5,114,719 A | 5/1992 | Sabel et al. |
| 5,208,111 A | 5/1993 | Decher et al. |
| 5,245,012 A | 9/1993 | Lombari et al. |
| 5,263,992 A | 11/1993 | Guire |
| 5,270,419 A | 12/1993 | Domb |
| 5,364,634 A | 11/1994 | Lew |
| 5,397,848 A | 3/1995 | Yang et al. |
| 5,399,665 A | 3/1995 | Barrera et al. |
| 5,462,990 A | 10/1995 | Hubbell et al. |
| 5,512,131 A | 4/1996 | Kumar et al. |
| 5,512,600 A | 4/1996 | Mikos et al. |
| 5,514,378 A | 5/1996 | Mikos et al. |
| 5,518,767 A | 5/1996 | Rubner et al. |
| 5,536,573 A | 7/1996 | Rubner et al. |
| 5,539,083 A | 7/1996 | Cook et al. |
| 5,576,881 A | 11/1996 | Doerr et al. |
| 5,630,941 A | 5/1997 | Burger et al. |
| 5,660,873 A | 8/1997 | Nikolaychik et al. |
| 5,696,175 A | 12/1997 | Mikos et al. |

(Continued)

FOREIGN PATENT DOCUMENTS

| | | |
|---|---|---|
| CN | 1679518 A | 10/2005 |
| DE | 19812083 A1 | 9/1999 |

(Continued)

OTHER PUBLICATIONS

Sayers ( Chemical Science (2018) vol. 9, p. 896, published online Nov. 22, 2017).*
Armitage (Biochemistry 1998) vol. 37, pp. 9417-9425).*
Abeloff et al., "Chapter 95: Cancer of the Breast," Abeloff's Clinical Oncology, Fourth Edition, Churchill Livingstone Elsevier, pp. 1875-1943 (2008).
Abramoff et al., "Image Processing with ImageJ," Biophotonics International, 11: 36-42 (2004).
Absolom et al., "Protein adsorption to polymer particles: role of surface properties," J Biomed Mater Res, 21(2): 161-71 (1987).
Afonin et al., "In vitro assembly of cubic RNA-based scaffolds designed in silico," Nature Nanotechnol, 5: 676-682 (2010).

(Continued)

*Primary Examiner* — Steven Pohnert
(74) *Attorney, Agent, or Firm* — Foley Hoag LLP; Alexander Akhiezer

(57) ABSTRACT

The present disclosure relates to a device, comprising a base and a plurality of microneedles attached to the base, wherein each microneedle has an outer surface; the outer surface of at least one microneedle being coated with a composition comprising at least one polymer and least one Peptide Nucleic Acid (PNA). The present disclosure additionally relates to a method of detecting an analyte in interstitial fluid (ISF), comprising contacting the device to a subject, for example, to human skin.

24 Claims, 14 Drawing Sheets

(10 of 14 Drawing Sheet(s) Filed in Color)

(56) References Cited

U.S. PATENT DOCUMENTS

| | | |
|---|---|---|
| 5,700,559 A | 12/1997 | Sheu et al. |
| 5,714,166 A | 2/1998 | Tomalia et al. |
| 5,716,303 A | 2/1998 | Scatterday |
| 5,716,404 A | 2/1998 | Vacanti et al. |
| 5,716,709 A | 2/1998 | Ferguson et al. |
| 5,736,372 A | 4/1998 | Vacanti et al. |
| 5,770,417 A | 6/1998 | Vacanti et al. |
| 5,797,898 A | 8/1998 | Santini, Jr. et al. |
| 5,804,178 A | 9/1998 | Vacanti et al. |
| 5,807,636 A | 9/1998 | Sheu et al. |
| 5,837,377 A | 11/1998 | Sheu et al. |
| 5,837,752 A | 11/1998 | Shastri et al. |
| 5,858,746 A | 1/1999 | Hubbell et al. |
| 5,902,599 A | 5/1999 | Anseth et al. |
| 5,902,800 A | 5/1999 | Green et al. |
| 5,904,927 A | 5/1999 | Amiji |
| 5,962,520 A | 10/1999 | Smith et al. |
| 6,022,590 A | 2/2000 | Ferguson et al. |
| 6,060,582 A | 5/2000 | Hubbell et al. |
| 6,089,853 A | 7/2000 | Biebuyck et al. |
| 6,095,148 A | 8/2000 | Shastri et al. |
| 6,103,266 A | 8/2000 | Tapolsky et al. |
| 6,114,099 A | 9/2000 | Liu et al. |
| 6,123,681 A | 9/2000 | Brown |
| 6,123,727 A | 9/2000 | Vacanti et al. |
| 6,127,143 A | 10/2000 | Gunasekaran |
| 6,131,211 A | 10/2000 | Hennessey |
| 6,180,239 B1 | 1/2001 | Whitesides et al. |
| 6,180,329 B1 | 1/2001 | Paris |
| 6,235,224 B1 | 5/2001 | Mathiowitz et al. |
| 6,235,334 B1 | 5/2001 | Donovan |
| 6,245,537 B1 | 6/2001 | Williams et al. |
| 6,267,776 B1 | 7/2001 | O'Connell |
| 6,267,784 B1 | 7/2001 | Benz et al. |
| 6,302,848 B1 | 10/2001 | Larson et al. |
| 6,310,188 B1 | 10/2001 | Mukherjee |
| 6,312,727 B1 | 11/2001 | Schacht et al. |
| 6,325,810 B1 | 12/2001 | Hamilton et al. |
| 6,337,198 B1 | 1/2002 | Levene et al. |
| 6,372,244 B1 | 4/2002 | Antanavich et al. |
| 6,379,690 B2 | 4/2002 | Blanchard et al. |
| 6,395,734 B1 | 5/2002 | Tang et al. |
| 6,402,918 B1 | 6/2002 | Schlenoff et al. |
| 6,433,134 B1 | 8/2002 | Patron et al. |
| 6,447,887 B1 | 9/2002 | Claus et al. |
| 6,451,871 B1 | 9/2002 | Winterton et al. |
| 6,479,146 B1 | 11/2002 | Caruso et al. |
| 6,492,096 B1 | 12/2002 | Liu et al. |
| 6,497,729 B1 | 12/2002 | Moussy et al. |
| 6,699,501 B1 | 3/2004 | Neu et al. |
| 6,716,813 B2 | 4/2004 | Lim et al. |
| 6,740,643 B2 | 5/2004 | Wolff et al. |
| 6,743,521 B2 | 6/2004 | Hubbell et al. |
| 6,833,192 B1 | 12/2004 | Caruso et al. |
| 6,860,980 B2 | 3/2005 | Locascio et al. |
| 6,896,926 B2 | 5/2005 | Qiu et al. |
| 6,919,373 B1 | 7/2005 | Lam et al. |
| 6,998,115 B2 | 2/2006 | Langer et al. |
| 7,045,087 B2 | 5/2006 | Kotov |
| 7,045,146 B2 | 5/2006 | Caruso et al. |
| 7,101,575 B2 | 9/2006 | Donath et al. |
| 7,101,947 B2 | 9/2006 | Schlenoff et al. |
| 7,112,361 B2 | 9/2006 | Lynn et al. |
| 7,223,327 B2 | 5/2007 | Schlenoff et al. |
| 7,303,814 B2 | 12/2007 | Lamberti et al. |
| 7,348,399 B2 | 3/2008 | Haynie |
| 7,364,585 B2 | 4/2008 | Weber |
| 7,365,142 B2 | 4/2008 | Schlenoff et al. |
| 7,427,354 B2 | 9/2008 | Eto |
| 7,427,394 B2 | 9/2008 | Anderson et al. |
| 7,491,263 B2 | 2/2009 | Wang et al. |
| 7,879,575 B2 | 2/2011 | Kricka et al. |
| 8,105,652 B2 | 1/2012 | Wood et al. |
| 8,685,538 B2 | 4/2014 | Torchilin et al. |
| 9,198,875 B2 | 12/2015 | Smith et al. |
| 9,320,750 B2 | 4/2016 | Yaffe et al. |
| 9,393,217 B2 | 7/2016 | Hammond et al. |
| 9,463,244 B2 | 10/2016 | Castleberry et al. |
| 9,610,252 B2 | 4/2017 | DeMuth et al. |
| 9,737,557 B2 | 8/2017 | Hammond et al. |
| 10,278,927 B2 | 5/2019 | Hammond et al. |
| 11,419,947 B2 | 8/2022 | Barberio et al. |
| 2002/0053514 A1 | 5/2002 | Locascio et al. |
| 2002/0131933 A1 | 9/2002 | Delmotte |
| 2002/0131951 A1 | 9/2002 | Langer et al. |
| 2002/0187197 A1 | 12/2002 | Caruso et al. |
| 2003/0059398 A1 | 3/2003 | Ranger et al. |
| 2003/0113368 A1 | 6/2003 | Nomoto et al. |
| 2003/0124368 A1 | 7/2003 | Lynn et al. |
| 2003/0236573 A1 | 12/2003 | Evans et al. |
| 2004/0013721 A1 | 1/2004 | Antipov et al. |
| 2004/0020423 A1 | 2/2004 | Lewis et al. |
| 2004/0044100 A1 | 3/2004 | Schlenoff et al. |
| 2004/0052865 A1 | 3/2004 | Gower et al. |
| 2004/0149572 A1 | 8/2004 | Schlenoff et al. |
| 2004/0258753 A1 | 12/2004 | Demeester et al. |
| 2005/0019404 A1 | 1/2005 | Sung et al. |
| 2005/0089890 A1 | 4/2005 | Cubicciotti |
| 2005/0152955 A1 | 7/2005 | Akhave et al. |
| 2005/0208100 A1 | 9/2005 | Weber et al. |
| 2005/0265961 A1 | 12/2005 | Langer et al. |
| 2005/0276841 A1 | 12/2005 | Davis et al. |
| 2006/0118754 A1 | 6/2006 | Lapen |
| 2006/0127437 A1 | 6/2006 | Kennedy et al. |
| 2006/0198897 A1 | 9/2006 | Pacetti et al. |
| 2006/0216494 A1 | 9/2006 | Furedi-Milhofer et al. |
| 2006/0246112 A1 | 11/2006 | Snyder et al. |
| 2006/0260777 A1 | 11/2006 | Rashba-Step et al. |
| 2007/0020469 A1 | 1/2007 | Wood et al. |
| 2007/0077276 A1 | 4/2007 | Haynie |
| 2007/0083186 A1 | 4/2007 | Carter et al. |
| 2007/0129792 A1 | 6/2007 | Picart et al. |
| 2007/0141100 A1 | 6/2007 | Sung et al. |
| 2007/0197568 A1 | 8/2007 | Bunn et al. |
| 2007/0276330 A1 | 11/2007 | Beck et al. |
| 2008/0139450 A1 | 6/2008 | Madhyastha et al. |
| 2008/0200982 A1 | 8/2008 | Your |
| 2008/0213461 A1* | 9/2008 | Gill ............... A61K 9/0021 427/2.3 |
| 2008/0228280 A1 | 9/2008 | Cohen et al. |
| 2008/0248108 A1 | 10/2008 | Krotz et al. |
| 2008/0286345 A1 | 11/2008 | Lynn et al. |
| 2008/0311177 A1 | 12/2008 | Hammond et al. |
| 2009/0018029 A1 | 1/2009 | Miao et al. |
| 2009/0047517 A1 | 2/2009 | Caruso et al. |
| 2009/0053139 A1 | 2/2009 | Shi et al. |
| 2009/0061006 A1 | 3/2009 | Leuschner et al. |
| 2009/0061451 A1 | 3/2009 | Achim et al. |
| 2009/0088479 A1 | 4/2009 | Allmendinger et al. |
| 2009/0088679 A1 | 4/2009 | Wood et al. |
| 2009/0155326 A1 | 6/2009 | Mack et al. |
| 2009/0170179 A1 | 7/2009 | Lynn et al. |
| 2009/0214615 A1 | 8/2009 | Zhao |
| 2009/0246142 A1 | 10/2009 | Bhatia et al. |
| 2009/0258045 A1 | 10/2009 | Chuang et al. |
| 2009/0263468 A1 | 10/2009 | McAnulty et al. |
| 2009/0275906 A1 | 11/2009 | Berland et al. |
| 2010/0003499 A1 | 1/2010 | Krogman et al. |
| 2010/0016439 A1 | 1/2010 | Thomes et al. |
| 2010/0040674 A1 | 2/2010 | Smith et al. |
| 2010/0143677 A1 | 6/2010 | Lee et al. |
| 2010/0189683 A1 | 7/2010 | Holmlund et al. |
| 2011/0038939 A1 | 2/2011 | Lvov et al. |
| 2011/0114244 A1 | 5/2011 | Yoo et al. |
| 2011/0143127 A1 | 6/2011 | Gupta et al. |
| 2011/0189292 A1 | 8/2011 | Lebreton et al. |
| 2011/0244048 A1 | 10/2011 | Amiji et al. |
| 2011/0301209 A1 | 12/2011 | Zaknoen et al. |
| 2012/0015146 A1 | 1/2012 | Advincula et al. |
| 2012/0027837 A1 | 2/2012 | DeMuth et al. |
| 2012/0058355 A1 | 3/2012 | Lee et al. |
| 2012/0156389 A1 | 6/2012 | Kotov |
| 2012/0207795 A1 | 8/2012 | Zink et al. |
| 2012/0277719 A1 | 11/2012 | Shukla et al. |

(56) References Cited

U.S. PATENT DOCUMENTS

| | | |
|---|---|---|
| 2012/0277852 A1 | 11/2012 | Shukla et al. |
| 2013/0130923 A1* | 5/2013 | Ehrich .................. G16B 25/20 506/7 |
| 2013/0190890 A1 | 7/2013 | Shah et al. |
| 2013/0243693 A1 | 9/2013 | Omenetto et al. |
| 2013/0273137 A1 | 10/2013 | Mandell et al. |
| 2014/0011759 A1 | 1/2014 | Yaffe et al. |
| 2014/0039575 A1 | 2/2014 | Bradley |
| 2014/0093575 A1 | 4/2014 | Hammond et al. |
| 2014/0302116 A1 | 10/2014 | Castleberry et al. |
| 2014/0328931 A1 | 11/2014 | Hammond et al. |
| 2015/0086599 A1 | 3/2015 | Hammond et al. |
| 2015/0125879 A1 | 5/2015 | Li et al. |
| 2015/0202304 A1 | 7/2015 | Kaplan et al. |
| 2015/0290669 A1 | 10/2015 | Li et al. |
| 2016/0038632 A1 | 2/2016 | Shah et al. |
| 2017/0181981 A1 | 6/2017 | Hammond et al. |
| 2017/0258738 A1 | 9/2017 | DeMuth et al. |
| 2017/0306399 A1* | 10/2017 | Bergsma .............. C12Q 1/6846 |
| 2020/0000713 A1 | 1/2020 | Bennett et al. |
| 2020/0377929 A1 | 12/2020 | Irvine et al. |
| 2023/0201367 A1 | 6/2023 | Barberio et al. |
| 2023/0242969 A1 | 8/2023 | Irvine et al. |

FOREIGN PATENT DOCUMENTS

| | | |
|---|---|---|
| DE | 29907804 U1 | 10/1999 |
| EP | 0 443 809 A2 | 8/1991 |
| EP | 1 116 516 A1 | 7/2001 |
| GB | 1213803 A | 11/1970 |
| GB | 1213805 A | 11/1970 |
| WO | WO-1995/11748 A1 | 5/1995 |
| WO | WO-1995/34595 A1 | 12/1995 |
| WO | WO-1996/03147 A1 | 2/1996 |
| WO | WO-97/08315 A1 | 3/1997 |
| WO | WO-1998/03573 A1 | 1/1998 |
| WO | WO-98/17330 A1 | 4/1998 |
| WO | WO-1998/47948 A1 | 10/1998 |
| WO | WO-1999/47253 A1 | 9/1999 |
| WO | WO-99/59647 A1 | 11/1999 |
| WO | WO-1999/56878 A1 | 11/1999 |
| WO | WO-2000/77281 A1 | 12/2000 |
| WO | WO-2001/57118 A2 | 8/2001 |
| WO | WO-2001/94441 A1 | 12/2001 |
| WO | WO-2002/12888 A2 | 2/2002 |
| WO | WO-2002/085500 A1 | 10/2002 |
| WO | WO-2003/035716 A1 | 5/2003 |
| WO | WO-2004/032974 A1 | 4/2004 |
| WO | WO-2006/051227 A1 | 5/2006 |
| WO | WO-2006/079928 A2 | 8/2006 |
| WO | WO-2006/086391 A2 | 8/2006 |
| WO | WO-2007/003054 A1 | 1/2007 |
| WO | WO-2007/140391 A2 | 12/2007 |
| WO | WO-2007/140402 A1 | 12/2007 |
| WO | WO-2008/057127 A1 | 5/2008 |
| WO | WO-2008/118133 A2 | 10/2008 |
| WO | WO-2008/157372 A2 | 12/2008 |
| WO | WO-2009/051734 A1 | 4/2009 |
| WO | WO-2009/117473 A2 | 9/2009 |
| WO | WO-2010/021973 A2 | 2/2010 |
| WO | WO-2010/026450 A1 | 3/2010 |
| WO | WO-2010/059963 A2 | 5/2010 |
| WO | WO-2010/097814 A2 | 9/2010 |
| WO | WO-2010/120531 A3 | 10/2010 |
| WO | WO-2011/140136 A2 | 11/2011 |
| WO | WO-2012/149492 A1 | 11/2012 |
| WO | WO-2012/149494 A2 | 11/2012 |
| WO | WO-2013/110047 A1 | 7/2013 |
| WO | WO-2013/163234 A1 | 10/2013 |
| WO | WO-2013/169479 A1 | 11/2013 |
| WO | WO-2014/012099 A1 | 1/2014 |
| WO | WO-2014/059269 A2 | 4/2014 |
| WO | WO-2014/066862 A2 | 5/2014 |
| WO | WO-2014/093934 A1 | 6/2014 |
| WO | WO-2014093934 A1 * | 6/2014 ......... A61B 10/0045 |
| WO | WO-2014/134029 A1 | 9/2014 |
| WO | WO-2014/150074 A1 | 9/2014 |
| WO | WO-2015/048315 A1 | 4/2015 |
| WO | WO-2016/022131 A1 | 2/2016 |
| WO | WO-2017/031060 A1 | 2/2017 |
| WO | WO-2017065696 A2 * | 4/2017 ........... A61K 31/713 |
| WO | WO-2017/117188 A1 | 7/2017 |
| WO | WO-2018/136754 A1 | 7/2018 |
| WO | WO-2018/202922 A1 | 11/2018 |
| WO | WO-2019/089567 A1 | 5/2019 |
| WO | WO-2021/002984 A1 | 1/2021 |

OTHER PUBLICATIONS

Ai et al., "Biomedical applications of electrostatic layer-by-layer nano-assembly of polymers, enzymes, and nanoparticles," Cell Biochem Biophys, 39(1):23-43 (2003).

Akinc et al., "A combinatorial library of lipid-like materials for delivery of RNAi therapeutics," Nature Biotechnol, 26:561-569 (2008).

Akinc et al., "Synthesis of poly(β-amino ester)s optimized for highly effective gene delivery," Bioconjugate Chem, 14:979-988 (2003).

Albeck et al., "Modeling a Snap-Action, Variable-Delay Switch Controlling Extrinsic Cell Death," PLoS Biology, 6(12): 2831-2852 (2008).

Albrektsson et al., "Osteoinduction, osteoconduction and osseointegration," Eur Spine J, 10(2):S96-101(2001).

Alsberg et al., "Craniofacial tissue engineering," Crit Rev Oral Biol Med, 12(1):64-75 (2001).

Alsberg et al., "Regulating bone formation via controlled scaffold degradation," J Dent Res, 82(11): 903-908 (2003).

Alvarez-Roman et al., "Skin penetration and distribution of polymeric nanoparticles," J Controlled Release, 99:53-62 (2004).

Alves et al., "Self assembling and crosslinking of polyelectrolyte multilayer films of chitosan and alginate studied by QCM and IR spectroscopy," Macromol Biosci, 9(8):776-85 (2009).

Anderson et al., "Biodegradation and Biocompatibility of PLA and PLGA Microspheres," Adv Drug Delivery Rev, 28: 5-24 (1997).

Anderson et al., "Semi-Automated Synthesis and Screening of a Large Library of Degradable Cationic Polymers for Gene Delivery," Angew Chem Int Ed, 42: 3151-3158 (2003).

Anderson, "Human Gene Therapy," Nature, 392: 25-30 (1998).

Ando et al., "PLGA Microspheres Containing Plasmid DNA: Preservation of Supercoiled DNA via Cryopreparation and Carbohydrate Stabilization," J Pharm Sci, 88: 126-130 (1999).

Antipov et al., "Sustained Release Properties of Polyelectrolyte Multilayer Capsules," J Phys Chem B, 105: 2281-2284 (2001).

Ariga et al., "Layer-by-layer assembly as a versatile bottom-up nanofabrication technique for exploratory research and realistic application," Phys Chem Chem Phys, 9(19):2319-40 (2007).

Armitage et al., "Hairpin-Forming Peptide Nucleic Acid Oligomers," Biochemistry, 37(26):9417-9425 (1998).

Balabushevich et al., "Protein-loaded microspheres prepared by sequential adsorption of dextran sulphate and protamine on melamine formaldehyde core," J Microencapsul, 26(7):571-9 (2009).

Balko et al., "Gene Expression Patterns that Predict Sensitivity to Epidermal Growth Factor Receptor Tyrosine Kinase Inhibitors in Lung Cancer Cell Lines and Human Lung Tumors," BMC Genomics, 7: 289-302 (2006).

Barberio, "Layer-by-Layer Nanoparticles for Cytokine Therapy," 2018 ACS Annual Meeting Boston (oral), 1-23 (Aug. 22, 2018).

Barberio, "Layer-by-Layer Nanoparticles for Cytokine Therapy," AIChE Bioengineering and Translational Medicine, presentation slides 1-20 (Sep. 27, 2018).

Barker et al., "Fabrication, Derivatization and Applications of Plastic Microfluidic Devices," Proceedings of SPIE—The International Society for Optical Engineering, 112-118 (2001).

Barrera et al., "Synthesis and RGD Peptide Modification of a New Biodegradable Copolymer: Poly (lactic acid-co-lysine)," J Am Chem Soc, 115: 11010-11011 (1993).

(56) References Cited

OTHER PUBLICATIONS

Baselga et al., "Phase II Multicenter Study of the Antiepidermal Growth Factor Receptor Monoclonal Antibody Cetuximab in Combination with Platinum-Based Chemotherapy in Patients with Platinum-Refractory Metastatic and/or Recurrent Squamous Cell Carcinoma of the Head and Neck," J. of Clinical Oncology, 23(24): 5568-5577 (2005).
Bass, "RNA Interference the Short Answer," Nature, 411: 428-429 (2001).
Behr, "Synthetic Gene-Transfer Vectors," Acc Chem Res, 26: 274-278 (1993).
Behr, "The Proton Sponge: A Trick to Enter Cells the Viruses Did Not Exploit," Chimia, 51: 34-36 (1997).
Benkirane-Jessel et al., "Build-up of Polypeptide Multilayer Coatings with Anti-Inflammatory Properties Based on the Embedding of Piroxicam-Cyclodextrin Complexes," Advanced Functional Materials, 14(2): 174-182 (2004).
Berg et al., "Controlling mammalian cell interactions on patterned polyelectrolyte multilayer surfaces," Langmuir, 20(4): 1362-8 (2004).
Bernards et al., "Nanotemplating of Biodegradable Polymer Membranes for Constant-Rate Drug Delivery," Adv Mater, 22: 2358-2362 (2010).
Bershteyn et al., "Polymer-supported lipid shells, onions, and flowers," Soft Matter, 4(9):1787-1791 (2008).
Beyer et al., "Periodic DNA nanotemplates synthesized by rolling circle amplification," Nano Lett, 5: 719-722 (2005).
Biggs et al., "The use of nanoscale topography to modulate the dynamics of adhesion formation in primary osteoblasts and ERK/MAPK signalling in STRO-1+ enriched skeletal stem cells," Biomaterials, 30(28):5094-103 (2009).
Bins et al., "A rapid and potent DNA vaccination strategy defined by in vivo monitoring of antigen expression," Nat. Med, 11:899-904 (2005).
Blacklock et al., "Cross-linked bioreducible layer-by-layer films for increased cell adhesion and transgene expression" J Phys Chem B, 114(16):5283-91 (2010).
Boes et al., "T-cell engagement of dendritic cells rapidly rearranges MHC class II transport," Nature, 418: 983-988 (2002).
Bonewald et al., "Von Kossa staining alone is not sufficient to confirm that mineralization in vitro represents bone formation," Calcified Tissue Int, 72(5):537-47 (2003).
Bott, "Applications of "Wired" Enzyme Electrodes," Current Separations, 21(1): 3-6 (2004).
Boudou et al., "Internal composition versus the mechanical properties of polyelectrolyte multilayer films: the influence of chemical cross-linking," Langmuir, 25(24):13809-19 (2009).
Boudou et al., "Multiple functionalities of polyelectrolyte multilayer films: new biomedical applications," Adv Mater, 22(4):441-467 (2010).
Boussif et al., "A Versatile Vector for Gene and Oligonucleotide Transfer into Cells in Culture and In Vivo: Polyethylenimine," Proc Natl Acad Sci, USA, 92: 7297-7301 (1995).
Brama et al., "Effect of titanium carbide coating on the osseointegration response in vitro and in vivo," Biomaterials, 28(4):595-608 (2007).
Brange et al., "Insulin formulation and delivery," Pharm Biotechnol, 10:343-409 (1997).
Brazeau et al., "In Vitro Myotoxicity of Selected Cationic Macromolecules Used in Non-Viral Gene Delivery," Pharm Res, 15: 680-684 (1998).
Breger et al., "Synthesis of "click" alginate hydrogel capsules and comparison of their stability, water swelling, and diffusion properties with that of $Ca^{+2}$ crosslinked alginate capsules," J. Biomed. Mat. Res. B Appl. Biomat., 103:1120-1132 (2015).
Brewer et al., "Condensation of DNA by spermatid basic nuclear proteins," J Biol Chem, 277(41):38895-900 (2002).
Brewster et al., "Cyclodextrins as Pharmaceutical Solubilizers," Advanced Drug Delivery Reviews, 59: 645-666 (2007).
Bryzgunova et al., "Isolation and Comparative Study of Cell?Free Nucleic Acids from Human Urine," Annals of the New York Academy of Sciences, 1075:334-340 (2006).
Burke et al., "pH Responsive Properties of Multilayered Poly(L-lysine)/Hyaluronic Acid Surfaces," Biomacromolecules, 4: 1773-1783 (2003).
Buser et al., "The Crystal Structure of Prussian Blue: $Fe4[Fe(CN)5]3XH2O$," Inorganic Chemistry, 16(11): 2704-2710 (1977).
Calvo et al., "Donnan Permselectivity in Layer-by-Layer Self-Assembled Redox Polyelectrolyte Thin Film," J Am Chem Soc, 124: 8490-8497 (2002).
Carey et al., "EGFR Inhibition with Cetuximab Added to Carboplatin in Metastatic Triple-negative (basal-like) Breast Cancer," Supplement to Journal of Clinical Oncology, ASCO Annual Meeting Proceedings, TBCRC 001: Clinical Science Symposium, 43S (2009).
Carpenter et al., "A Single-Film Electrochromic Device," J Electrochem Soc, 137(8): 2464-2467 (1990).
Carpenter et al., "CellProfiler: Image Analysis Software for Identifying and Quantifying Cell Phenotypes," Genome Biology, 7(10): R100-R100.11 (2006).
Carragee et al., "A critical review of recombinant human bone morphogenetic protein-2 trials in spinal surgery: emerging safety concerns and lessons learned," Spine J, 11(6): 471-491 (2011).
Carrell et al., "The aetiology of sperm protamine abnormalities and their potential impact on the sperm epigenome," Int J Androl, 31(6):537-45 (2008).
Caruso, "COLL 34-Polymer Design and Assembly for Next-Generation Particle Delivery," Abstracts of Papers, The 237th ACS National Meeting and Exposition, Salt Lake City, UT (Mar. 22-26, 2009).
Castleberry et al., "220-Surface Mediated Delivery of siRNA from Layer-By-Layer Assembled Polyelectrolyte Films for the Acceleration of Wound Healing," Abstracts of Papers, 244th ACS National Meeting and Exposition, Philadelphia, PA (Aug. 19-23, 2012).
Castleberry et al., "Nanolayered siRNA Dressing for Sustained Localized Knockdown," ACS NANO, 7(6): 5251-5261 (2013).
Cavalieri et al., "Assembly and functionalization of DNA-polymer microcapsules," ACS Nano 3(1):234-240 (2009).
Chen, "Preparation, Characterization, and Electrocatalytic Oxidation Properties of Iron, Cobalt, Nickel, and Indium Hexacyanoferrate," Journal of Electroanalytical Chemistry, 521: 29-52 (2002).
Chikh et al., "Attaching histidine-tagged peptides and proteins to lipid-based carriers through use of metal-ion-chelating lipids," Biochim Biophys Acta 1567:204-212 (2002).
Cho, "MicroRNAs: Potential biomarkers for cancer diagnosis, prognosis and targets for therapy," The International Journal of Biochemistry & Cell Biology, 42(8):1273-1281 (2010).
Choksakulnimitr et al., "In Vitro Cytotoxicity of Macromolecules in Different Cell Culture Systems," Journal of Controlled Release 34: 233-241 (1995).
Chou et al., "Quantitative Analysis of Dose-Effect Relationships: The Combined Effects of Multiple Drugs or Enzymes Inhibitors," Advances in Enzyme Regulation, 22: 27-55 (1984).
Christensen et al., "Heparin Coating of the Stent Graft-effects on Platelets, Coagulation and Complement Activation," Biomaterials, 22: 349-355 (2001).
Chua et al., "Effect of microneedles shape on skin penetration and minimally invasive continuous glucose monitoring in vivo," Sensors and Actuators A: Physical, 203:373-381 (2013).
Cini et al., "Step-by-step assembly of self-patterning polyelectrolyte films violating (almost) all rules of layer-by-layer deposition," J Am Chem Soc, 132(24):8264-5 (2010).
Clark et al., "Selective Deposition in Multilayer Assembly: SAMs as Molecular Templates," Supramolecular Science, 4: 141 (1997).
Corkery et al., "Epidermal Growth Factor Receptor as a Potential Therapeutic Target in Triple-negative Breast Cancer," Annals of Oncology, 20: 862-867 (2009).
Correa et al., "Tuning Nanoparticle Interactions with Ovarian Cancer through Layer-by-Layer Modification of Surface Chemistry," ACS Nano, 14: 2224-2237 (2020) : Supporting Information.

(56) References Cited

OTHER PUBLICATIONS

Correa et al., "Tuning Nanoparticle Interactions with Ovarian Cancer through Layer-by-Layer Modification of Surface Chemistry," ACS Nano, 14: 2224-2237 (2020).
Cotten et al., "Receptor-Mediated Transport of DNA into Eukaryotic Cells," Methods Enzym, 217: 618-644 (1993).
Crane et al., Cyclodextrin Inclusion Complexes with a Solvatochromic Fluorescent Probe, Journal of Chemical Education, 79(10): 1261-1263 (2002).
Crouzier et al., "Ion pairing and hydration in polyelectrolyte multilayer films containing polysaccharides," Biomacromolecules, 10(2):433-42 (2009).
Crouzier et al., "The performance of BMP-2 loaded TCP/HAP porous ceramics with a polyelectrolyte multilayer film coating," Biomaterials, 32(30): 7543-7554 (2011).
Crystal, "Transfer of Genes to Humans: Early Lessons and Obstacles to Success," Science, 270: 404-410 (1995).
Dalby et al., "The control of human mesenchymal cell differentiation using nanoscale symmetry and disorder," Nat Mater, 6(12):997-1003 (2007).
Danese et al., "Circulating Nucleic Acids and Hemostasis: Biological Basis behind Their Relationship and Technical Issues in Assessment," Semin Thromb Hemost, 40:766-773 (2014).
Danhier et al., "PLGA-based nanoparticles: an overview of biomedical applications," J Control Release, 161(2): 505-522 (2012).
Danusso et al., "Synthesis of Tertiary Amine Polymers," Polymer, 11: 88-113 (1970).
Daubendiek et al., "Rolling-circle RNA-synthesis—circular oligonucleotides as efficient substrates for T7 RNA polymerase," J Am Chem Soc, 117:7818-7819 (1995).
Davis et al., "Evidence of RNAi in humans from systemically administered siRNA via targeted nanoparticles," Nature, 464: 1067-1070 (2010).
Davis et al., "Challenges and potential for RNA nanoparticles (RNPs)," J Biomed Nanotechnol, 5(1):36-44 (2009).
Davis et al., "Cyclodextrin-Based Pharmaceutics: Past, Present and Future," Nature Reviews, 3: 1023-1035 (2004).
de Jonge et al., "The osteogenic effect of electrosprayed nanoscale collagen/calcium phosphate coatings on titanium," Biomaterials, (9):2461-9 (2010).
Decher et al., "Buildup of Ultrathin Multilayer Films by a Self-Assembly Process, 1 Consecutive Adsorption of Anionic and Cationic Bipolar Amphiphiles on Charged Surfaces," Makromol Chem, Macro Mol Symp, 46: 321-327 (1991).
Decher et al., "Buildup of Ultrathin Multilayer Films by a Self-Assembly Process, II. Consecutive Adsorption of Anionic and Cationic Bipolar Amphilphiles and Polyelectrolytes on Charged Surfaces," Ber Bunsenges Phys Chem, 95(11): 1430-1434 (1991).
Decher et al., "Fuzzy Nanoassemblies: Toward Layer Polymeric Multicomposites," Science, 277: 1232-1237 (1997).
Decher et al., "Layer-by-layer assembled multicomposite Films," Current Opinion in Colloid & Interface Science, 3: 32-39 (1998).
Decher et al., "New Nanocomposite Films for Biosensors: Layer-by-layer Absorbed Films of Polyelectrolytes, Protein or DNA," Biosensors & Bioelectronics, 9: 677-684 (1994).
Delongchamp et al., "Fast Ion Conduction in Layer-By-Layer Polymer Films," Chem Mater, 15: 1165-1173 (2003).
Delongchamp et al., "High-Contrast Electrochromism and Controllable Dissolution of Assembled Prussian Blue/Polymer Nanocomposites," Adv Funct Mater, 14(3): 224-231 (2004).
Delongchamp, "High-Contrast Electrochromism from Layer-By-Layer Polymer Films," Chem Mater, 15: 1575-1586 (2003).
Demeneix et al., "The Proton Sponge: A Trick the Viruses did not Exploit," in ACS Conference Proceedings Series ; 146-151, Artificial self-assembling systems for gene delivery; 1995; Washington; DC.
Demidov et al., "Stability of peptide nucleic acids in human serum and cellular extracts," Biochem. Pharmacol., 48:1310-1313 (1994).

DeMuth et al., "Implantable silk composite microneedles for programmable vaccine release kinetics and enhanced immunogenicity in transcutaneous immunization," Adv. Healthcare Mater., 3(1):47-58 (2014).
DeMuth et al., "Implantable Silk Composite Microneedles for Programmable Vaccine Release Kinetics and Enhanced Immunogenicity in Transcutaneous Immunization," Advance Healthcare Materials, 3(1): 47-58 (2014).
DeMuth et al., "Nano-layered microneedles for transcutaneous delivery of polymer nanoparticles and plasmid DNA," Adv Mater, 22(43):4851-6 (2010).
DeMuth et al., "Polymer multilayer tattooing for enhanced DNA vaccination," Nat Mater, 12(4): 367-376 (2013).
Dent et al., "Triple-Negative Breast Cancer: Clinical Features and Patterns of Recurrence," Clinical Cancer Research, 13: 4429-4434 (2007).
Deshmukh et al., "Liposome and Polylysine Mediated Gene Transfer," New J Chem, 21: 113-124 (1997).
Diaz et al., "Antitumor and Antiangiogenic Effect of the Dual EGFR and HER-2 Tyrosine Kinase Inhibitor Lapatinib in a Lung Cancer Model," BMC Cancer, 10: 188 (2010).
Diegelman et al., "Generation of circular RNAs and trans-cleaving catalytic RNAs by rolling transcription of circular DNA oligonucleotides encoding hairpin ribozymes," Nucleic Acids Res, 26:3235-3241 (1998).
Dimitriou et al., "Bone regeneration: current concepts and future directions," BMC medicine, 9:66 (2011).
Dimitrova et al., "Sustained delivery of siRNAs targeting viral infection by cell-degradable multilayered polyelectrolyte films," PNAS, 105(42): 16320-16325 (2008).
Dixon, "Quartz crystal microbalance with dissipation monitoring: enabling real-time characterization of biological materials and their interactions," J Biomol Tech, 19(3):151-8 (2008).
Doh et al., "Aqueous-processible photoresist polymer for multiple protein patterning: Synthesis, characterization and application to T cell activation," Polymeric Materials Science and Engineering, 93:327-328 (2005).
Doh et al., "Photogenerated polyelectrolyte bilayers from an aqueous-processible photoresist for multicomponent protein patterning," J Am Chem Soc, 126: 9110-9171 (2004).
Dowben, "General Physiology: A Molecular Approach," Harper & Row Publishers, pp. 142-143 (1969).
Dubas et al., "Multiple Membranes from "True" Polyelectrolyte Multilayers," J Am Chem Soc, 123: 5368-5369 (2001).
Dubas et al., "Polyelectrolyte Multilayers Containing a Weak Polyacid: Construction and Deconstruction," Macromolecules, 34: 3736-3740 (2001).
Duek et al., "A Solid-State Electrochromic Device Based on Polyaniline, Prussian Blue and an Elastomeric Electrolyte," Advanced Materials, 5(9): 650-652 (1993).
Egholm et al., "PNA hybridizes to complementary oligonucleotides obeying the Watson-Crick hydrogen-bonding rules," Nature, 365:566-568 (1993).
Ekins et al., "24: Pathway Mapping Tools for Analysis of High Content Data," Methods in Molecular Biology, 356: 319-350 (2007).
Ekwueme et al., "Model-based estimates of risks of disease transmission and economic costs of seven injection devices in sub-Saharan Africa," Bulletin of the World Health Organization, 80:859-870 (2002).
El-Ghannam et al., "Model surfaces engineered with nanoscale roughness and RGD tripeptides promote osteoblast activity," J Biomed Mater Res, 68(4):615-27 (2004).
Elbakry et al., "Layer-by-layer assembled gold nanoparticles for siRNA delivery," Nano Lett, 9:2059-2064 (2009).
Elbashir et al., "Duplexes of 21-nucleotide RNAs mediate RNA interference in cultured mammalian cells," Nature, 411:494-498 (2011).
Elbert et al., "Self-assembly and Steric Stabilization at Heterogeneous, Biological Surfaces Using Absorbing Block Copolymers," Chemistry & Biology, 5(3): 177-183 (1998).
European Search Report for EP Application No. 13781212.9 dated Aug. 18, 2015.

(56) References Cited

OTHER PUBLICATIONS

Facca et al., "Active multilayered capsules for in vivo bone formation," Proc Natl Acad Sci, 107(8): 3406-3411 (2010).
Ferruti et al., "Amphoteric Linear Poly(amido-amine)s as Endosomolytic Polymers: Correlation between Physicochemical and Biological Properties," Macromolecules, 33(21): 7793-7800 (2000).
Ferruti et al., "Linear Amino Polymers: Synthesis, Protonation and Complex Formation," Advances in Polymer Science, 58: 55-92 (1984).
Ferruti et al., "Recent Results on Functional Polymers and Macromonomers of Interest as Biomaterials or for Biomaterial Modification," Biomaterials, 15: 1235-1241 (1994).
Ferruti et al., "Synthesis, Characterisation and Antitumour Activity of Platinum (II) Complexes of Novel Functionalised Poly(amidoamine)s," Macromol Chem Phys, 200: 1644-1654 (1999).
Ferruti et al., "Synthesis, Physico-Chemical Properties and Biomedical Applications of Poly(aminoamine)s," Polymer, 26: 1336 (1985).
Fire et al., "Potent and Specific Genetic Interference by Double-Stranded RNA in Caenorhabditis Elegans," Nature, 391: 806-811 (1998).
Fitzgerald et al., "Systems Biology and Combination Therapy in the Quest for Clinical Efficacy," Nature Chemical Biology, 2(9): 458-466 (2006).
Fleischhacker et al., "Circulating nucleic acids (CNAs) and cancer—A survey," Biochimica et Biophysica Acta (BBA)—Reviews on Cancer, 1775:181-232 (2007).
Flessner et al., "Degradable Polyelectrolyte Multilayers that Promote the Release of siRNA," Langmuir, 27(12): 7868-7876 (2011).
Freiberg et al., "Polymers Microspheres for Controlled Drug Release," Int J Pharm, 282: 1-18 (2004).
Friedman, "Human Gene Therapy—An Immature Genie, but Certainly Out of the Bottle," Nature Med, 2: 144-147 (1996).
Gao et al., "Layer-by-layer Electrodeposition of Redox Polymers and Enzymes on Screen-printed Carbon Electrodes for the Preparation of Reagentless Biosensors," ChemComm 7(1): 30-1 (2003).
Gaudet et al., "A Compendium of Signals and Responses Triggered by Prodeath and Prosurvival Cytokines," Molecular & Cellular Proteomics, 4: 1569-1590 (2005).
Gemici et al., "Hydrothermal treatment of nanoparticle thin films for enhanced mechanical durability," Langmuir, 24(5):2168-77 (2008).
Gerasimov et al., "Cytosolic Drug Delivery Using pH-and Light-Sensitive Liposomes," Adv Drug Delivery Rev, 38: 317-338 (1999).
Giljohann et al., "Gene regulation with polyvalent siRNA-nanoparticle conjugates," J Am Chem Soc, 131: 2072-2073 (2009).
Gill et al., "Coated microneedles for transdermal delivery," J Controlled Release, 117:227-237 (2007).
Gill et al., "Cutaneous vaccination using microneedles coated with hepatitis C DNA vaccine," Gene Ther, 17:811-814 (2010).
Giudice et al., "Needle-free vaccine delivery," Adv Drug Delivery Rev, 58(1): 68-89 (2006).
Glenn et al., "Transcutaneous immunization and immunostimulant strategies: capitalizing on the immunocompetence of the skin," Expert Rev Vaccines, 2:253 (2003).
Gonzalez et al., "New Class of Polymers for the Delivery of Macromolecular Therapeutics," Bioconjugate Chem, 10: 1068-1074 (1999).
Grabow et al., "Loaded-up Microsponges," Nature Materials, 11(4): 268-269 (2012).
Grabowski et al., "Bone graft and bone graft substitutes in spine surgery: current concepts and controversies," J Am Acad Orthop Sur, 21(1): 51-60 (2013).
Graham et al., "Phase inversion dynamics of PLGA solutions related to drug delivery," J Controlled Release 58(2): 233-245 (1999).
Grayson et al., "Electronic MEMS for Triggered Drug Delivery," Advanced Drug Delivery Reviews, 56: 173-184 (2004).
Greenland et al., "Beta-amino ester polymers facilitate in vivo DNA transfection and adjuvant plasmid DNA immunization," Molecular Therapy, 12(1):164-170 (2005).

Grewal et al., "Heterochromatin and epigenetic control of gene expression," Science, 301:798-802 (2003).
Guo, "RNA nanotechnology: engineering, assembly and applications in detection, gene delivery and therapy," J. Nanosci Nanotechnol, 5:1964-1982 (2005).
Guo, "Rolling Circle Transcription of Tandem siRNA to Generate Spherulitic RNA Nanoparticles for Cell Entry," Molecular Therapy, Nucleic Acids, 1: 3162-2531 (2012).
Guo, "The emerging field of RNA nanotechnology," Nature Nanotechnol, 5:833-842 (2010).
Habib et al., "A Tungsten-trioxide/prussian Blue Complementary Electrochromic Cell with a Polymer Electrolyte," Journal of Applied Electrochemistry, 21: 203-207 (1991).
Habib et al., "Effect of Temperature on a Complementary W03-Prussian Blue Electrochromic System," J Electrochem Soc, 139(8): 2155-2157 (1992).
Haensler et al., "Polyamidoamine Cascade Polymers Mediate Efficient Transfection of Cells in Culture," Bioconjugate Chem, 4: 372-379 (1993).
Hammond et al., "Formation of Polymer Microstructures by Selective Deposition of Polyion Multilayers Using Patterned Self-Assembled Monolayers as a Template," Macromolecules, 28: 7569-7571 (1995).
Hammond, "Building biomedical materials layer-by-layer," Mater Today, 15(5):196-206 (2012).
Hammond, "Form and Function in Multilayer Assembly: New Applications at the Nanoscale," Adv Mater, 16: 1271-1293 (2004).
Hanahan et al., "The Hallmarks of Cancer," Cell, 100: 57-70 (2000).
Hanes et al., "New Advances in Microsphere-Based Single-Dose Vaccines," Adv Drug Delivery Rev, 28: 97-119 (1997).
Hansen et al., "Re-Examination and Further Development of a Precise and Rapid Dye Method for Measuring Cell Growth/Cell Kill," Immunol Methods, 119: 203-210 (1989).
Haq et al., "Clinical administration of microneedles: Skin puncture, pain and sensation," Biomed Microdevices, 11:35 (2009).
Harper et al., "The DNA Damage Response: Ten Years After," Molecular Cell, 28(5): 739-745 (2007).
Haynie et al., "Protein-inspired multilayer nanofilms: science, technology and medicine," Nanomedicine, 2(3):150-7 (2006).
Hehrlein et al., "Drug-eluting Stent: The "Magic Bullet" for Prevention of Restenosis?" Basic Res Cardiol, 97: 417-423 (2002).
Helfrich et al., "Antitumor Activity of the Epidermal Growth Factor Receptor (EGFR) Tyrosine Kinase Inhibitor Gefitinib (ZD1839, Iressa) in Non-Small Cell Lung Cancer Cell Lines Correlates with Gene Copy Number and EGFR Mutations but not EGFR Protein Levels," Clinical Cancer Research, 12: 7117-7125 (2006).
Heller, "Redox Hydrogel-based Electrochemical Biosensors," Biosensors, Second Edition, edited by Jonathan Cooper, Anthony Cass, OUP Oxford, pp. 1-18 (2004).
Hendrix, "Bacteriophage DNA packaging: RNA gears in a DNA transport machine," Cell, 94(2):147-50 (1998).
Hill et al., "In Vitro Cytotoxicity of Poly(amidoamine)s: Relevance to DNA Delivery," Biochim Biophys Acta, 1427: 161-174 (1999).
Hillberg et al., "Effect of genipin cross-linking on the cellular adhesion properties of layer-by-layer assembled polyelectrolyte films," Biomaterials, 30(27):4463-70 (2009).
Hope et al., "Cationic Lipids, Phosphatidylethanolamine and the Intracellular Delivery of Polymeric, Nucleic Acid-Based Drugs (Review)," Molecular Membrane Biology, 15: 1-14 (1998).
Hossfeld et al., "Bioactive Coronary Stent Coating Based on Layer-By-Layer Technology for SiRNA Release," Acta Biomaterialia, 9(5): 6741-6752 (2013).
Hu et.al., "Regulation of Silk Material Structure by Temperature-Controlled Water Vapor Annealing," Biomacromolecules, 12: 1686-1696 (2011).
Hyrup et al., "Peptide Nucleic Acids (PNA): Synthesis, properties and potential applications," Bioorganic & Medicinal Chemistry, 4(1):5-23 (1996).
Isakoff et al., "Triple Negative Breast Cancer: Role of Specific Chemotherapy Agents," Cancer Journal, 16(1): 53-61 (2010).
Itaya et al., "Prussian-blue-modified Electrodes: An Application for a Stable Electrochromic Display Device," J Appl Phys, 53: 804-805 (1982).

(56) References Cited

OTHER PUBLICATIONS

Janes et al., "A Systems Model of Signaling Identifies a Molecular Basis Set for Cytokine-Induced Apoptosis," Science, 310: 1646-1653 (2005).
Janes et al., "Cytokine-Induced Signaling Networks Prioritize Dynamic Range over Signal Strength," Cell, 135: 343-354 (2008).
Jelle et al., "Transmission Spectra of an Electrochromic Window Consisting of Polyaniline, Prussian Blue and Tungsten Oxide," Electrochimica Acta, 38(11): 1497-1500 (1993).
Jessel et al., "Multiple and Time-scheduled in Situ DNA Delivery Mediated by ?-cyclodextrin Embedded in a Polyelectrolyte Multilayer," Proc Nat Acad Sci, 103(23): 8618-8621 (2006).
Jewell et al., "Multilayered polyelectrolyte assemblies as platforms for the delivery of DNA and other nucleic acid-based therapeutics" Adv. Drug Delivery Rev. 60: 979 (2008).
Jewell et al., "Multilayered polyelectrolyte films promote the direct and localized delivery of DNA to cells," J Controlled Release, 106: 214-223 (2005).
Jewell et al., "Release of Plasmid DNA from Intravascular Stents Coated with Ultrathin Multilayered Polyelectrolyte Films," Biomacromolecules, 7: 2483-2491 (2006).
Jiang et al., "Selective Deposition in Layer-by-Layer Assembly: Functional Graft," Langmuir, 16: 8501-8509 (2000).
Jin et al., "Electrospinning Bombyx mori Silk with Poly(ethylene oxide)," Biomacromolecules, 3: 1233-9 (2002).
Johannsmann et al., "Effect of sample heterogeneity on the interpretation of QCM(-D) data: comparison of combined quartz crystal microbalance/atomic force microscopy measurements with finite element method modeling," Anal Chem, 80(23): 8891-8899 (2008).
Johansen et al., "Antigen kinetics determines immune reactivity," Proc Natl Acad Sci U.S. A., 105: 5189-5194 (2008).
John Wiley and Sons, Lysozyme: Substrate Structure, accessed Oct. 15, 2014, p. 1.
Johnston et al., "Targeting Cancer Cells: Controlling the Binding and Internalization of Antibody-Functionalized Capsules," ACS Nano, 6(8): 6667-6674 (2012).
Kabanov et al., "DNA Complexes with Polycations for the Delivery of Genetic Material into Cells," Bioconjugate Chem, 6: 7-20 (1995).
Kang et al., "Inhibition of EGFR Signaling Augments Oridonin-induced Apoptosis in Human Laryngeal Cancer Cells via Enhancing Oxidative Stress Coincident with Activation of Both the Intrinsic and Extrinsic Apoptotic Pathways," Cancer Letters, 294: 147-158 (2010).
Kearney et al., "Macroscale delivery systems for molecular and cellular payloads," Nat Mater, 12(11): 1004-1017 (2013).
Keselowsky et al., "Integrin as controls osteoblastic proliferation and differentiation responses to titanium substrates presenting different roughness characteristics in a roughness independent manner," J Biomed Mater Res A, 80(3): 700-710 (2007).
Khan et al., "Tissue engineering of bone: material and matrix considerations," J Bone Joint Surg, 90(Suppl 1): 36-42 (2008).
Khopade et al., "Electrostatically Assembled Polyelectrolyte/Dendrimer Multilayer Films as Ultrathin Nanoreservoirs," Nano Letters, 2: 415 (2002).
Kim et al., "Enhanced memory responses to seasonal H1N1 influenza vaccination of the skin with the use of vaccine-coated microneedles," J Infect Dis, 201(2): 190-198 (2010).
Kim et al., "Hydrogen-Bonding Layer-by-Layer-Assembled Biodegradable Polymeric Micelles as Drug Delivery Vehicles from Surfaces," ACS Nano, 2(2): 386-392 (2008).
Kim et al., "MAD (multiagent delivery) nanolayer: delivering multiple therapeutics from hierarchically assembled surface coatings," Langmuir, 25(24): 14086-14092 (2009).
Kim, "Recent Advances in Understanding the Cell Death Pathways Activated by Anticancer Therapy," Cancer, 103(8): 1551-1560 (2005).
Kinsella et al., "BMP-2- mediated regeneration of large-scale cranial defects in the canine: an examination of different carriers," Plast Reconstr Surg, 127(5): 1865-1873 (2011).
Klopman et al., "Recent Methodologies for the Estimation of N-Octanol/Water Partition Coefficients and their Use in the Prediction of Membrane Transport Properties of Drugs," Mini-Reviews in Medicinal Chemistry, 5: 127-133 (2005).
Knapp et al., "Crystal Structure of the Human Ecto-50-Nucleotidase (CD73): Insights into the Regulation of Purinergic Signaling," Structure, 20: 2161-2173 (2012).
Kolluru et al., "Recruitment and Collection of Dermal Interstitial Fluid Using a Microneedle Patch," Adv Healthc Mater., 8(3):e1801262 (2019).
Krebs et al., "The formation of spherulites by amyloid fibrils of bovine insulin," Proc Natl Acad Sci USA, 101: 14420-14424 (2004).
Krogman et al., "Industrial-scale spray layer-by-layer assembly for production of biomimetic photonic systems," Bioinspiration & Biomimetics, 8(4): 045005 (2013).
Krogman et al., "Spraying asymmetry into functional membranes layer-by-layer," Nat Mater, 8: 512-518 (2009).
Kuchler-Bopp et al., "Nanostructured hybrid materials for bone-tooth unit regeneration," Open Journal of Regenerative Medicine, 2(1): 47-52 (2013).
Kukowska-Latallo et al., "Efficient Transfer of Genetic Material into Mammalian Cells Using Starburst Polyamidoamine Dendrimers," Proc Nat Acad Sci USA, 93: 4897-4902 (1996).
Kumar et al., "Patterning Self-Assembled Monolayers: Applications in Materials Science," Langmuir, 10: 1498-1511 (1994).
Kwon et al., "Pseudopoly(amino acids): A Study of the Synthesis and Characterization of Poly(trans-4-hydroxy-N-acyi-L-proline esters)," Macromolecules, 22: 3250-3255 (1989).
Landes et al., "Maxillary and mandibular osteosyntheses with PLGA and P(L/DL)LA implants: A 5-year inpatient biocompatibility and degradation experience," Plastic and Reconstructive Surgery, 117(7): 2347-2360 (2006).
Langer, "Biomaterials in Drug Delivery and Tissue Engineering: One Laboratory's Experience," Acc Chem Res, 33: 94-101 (2000).
Langer, "Selected Advances in Drug Delivery and Tissue Engineering," J Control Release, 62: 7-11 (1999).
Lavan et al., "Small-scale Systems for in vivo Drug Delivery," Nature Biotechnology, 21(10): 1184-1191 (2003).
Lavos-Valereto et al., "In vitro and in vivo biocompatibility testing of Ti—6Al—7Nb alloy with and without plasma-sprayed hydroxyapatite coating," J Biomed Mater Res, 58(6):727-733 (2001).
Lawrence et al., "Bioactive Silk Protein Biomaterial Systems for Optical Devices," Biomacromolecules, 9(4): 1214-1220 (2008).
Lawrence et al., "Processing methods to control silk fibroin film biomaterial features," Journal of Material Sciences, 43: 6967-6985 (2008).
Lee et al., "Gold, poly(β-amino ester) nanoparticles for small interfering RNA delivery," Nano Lett, 9: 2402-2406 (2009).
Lee et al., "Growth factor delivery-based tissue engineering: general approaches and a review of recent developments," Journal of the Royal Society Interface, 8(55): 153-170 (2011).
Lee et al., "Self-assembled RNA Interference Microsponges for Efficient siRNA Delivery," Nature Materials, 11(4): 316-322 (2012).
Leguen et al., "Bioactive coatings based on polyelectrolyte multilayer architectures functionalized by embedded proteins, peptides or drugs," Biomol Eng, 24(1): 33-41 (2007).
Liang et al., "The minimal functional sequence of protamine," Biochem Biophys Res Commun, 336(2): 653-659 (2005).
Liao et al., "Response of rat osteoblast-like cells to microstructured model surfaces in vitro," Biomaterials, 24(4): 649-654 (2003).
Lichter et al., "Recent Advances in Radiation Oncology," New England Journal of Medicine, 332(6): 371-379 (1995).
Lieschke et al., "Bioactive murine and human interleukin-12 fusion proteins which retain antitumor activity in vivo," Nat Biotech 15:35-40 (1997).
Lim et al., "A Self-Destroying Polycationic Polymer: Biodegradable Poly(4-Hydroxy-L-proline Ester)," J Am Chem Soc, 121: 5633-5639 (1999).
Lim et al., "Cationic Hyperbranched Poly(amino ester): A Novel Class of DNA Condensing Molecule with Cationic Surface, Biodegradable Three-Dimensional Structure, and Tertiary Amine Groups in the Interior," J Am Chem Soc, 123: 2460-2461 (2001).

(56) References Cited

OTHER PUBLICATIONS

Lim et al., "Development of a Safe Gene Delivery System Using Biodegradable Polymer, Poly [?-(4-Aminobutyl-L-qlycolic Acid]," J Am Chem Soc, 122: 6524-6525 (2000).
Lin et al., "PEG hydrogels for the controlled release of biomolecules in regenerative medicine," Pharmaceutical Research, 26(3): 631-643 (2009).
Linhardt et al., "Free-Radical Synthesis of Poly(2-Ethylacrylic Acid) Fractions of Low Polydispersity: Effects of Molecular Weight and Polydispersity on the pH-Dependent Conformational Transition in Aqueous Solution," Macromolecules, 32: 4457-4459 (1999).
Linhardt et al., "pH-Induced Fusion and Lysis of Phosphatidylcholine Vesicles by Hydrophobic Polyelectrolyte Poly(2-ethylacrylic Acid)," Langmuir, 16: 122-127 (2000).
Liu, "Ultrathin Multilayered Films that Promote the Release of Two DNA Constructs with Separate and Distinct Release Profiles," Adv Mater, 20: 4148-4153 (2008).
Livingstone et al., "Theoretical Property Predictions," J Curr Top Med Chem, 3: 1171-1192 (2003).
Lo et al., "Fabrication of controlled release biodegradable foams by phase separation," Tissue Eng, 1(1): 15-28 (1995).
Lopez et al., "Gefitinib Inhibition of Drug Resistance to Doxorubicin by Inactivating ABCG2 in Thyroid Cancer Cell Lines," Archives of Otolaryngology—Head & Neck Surgery, 133(10): 1022-1027 (2007).
Luo et al., "Synthetic DNA Delivery Systems," Nat Biotechnol, 18: 33-37 (2000).
Lynn et al., "Accelerated Discovery of Synthetic Transfection Vectors: Parallel Synthesis and Screening of a Degradable Polymer Library," Journal of the American Chemical Society, 123: 8155-8156 (2001).
Lynn et al., "Construction of Degradable Thin Films via Layer-by-Layer Deposition of Polyelectrolytes: Fabrication, Characterization, and Application to Controlled Release," MIT Proposal (2001).
Lynn et al., "Degradable Poly(Beta-amino esters): Synthesis, Characterization, and Self-Assembly with Plasmid DNA," J Am Chem Soc, 122: 10761-10768 (2000).
Lynn et al., "pH-Responsive Polymer Microspheres: Rapid Release of Encapsulated Material Within the Range of Intracellular pH," Angewandte Chemie International Edition, 40: 1707-1710 (2001).
Lynn, "Peeling Back the Layers: Controlled Erosion and Triggered Disassembly of Multilayered Polyelectrolyte Thin Films," Adv Mater, 19: 4118-4130 (2007).
Ma et al., "Collagen/chitosan porous scaffolds with improved biostability for skin tissue engineering," Biomaterials, 24: 4833-4841 (2003).
MacBeath, "Protein Microarrays and Proteomics," Nature Genetics Supplement, 32: 526-532 (2002).
Macdonald et al., "Release of a model protein from biodegradable self assembled films for surface delivery applications," J Controlled Release, 131(3): 228-234 (2008).
MacDonald et al., "Tissue Integration of Growth Factor-Eluting Layer-by-Layer Polyelectrolyte Multilayer Coated Implants," Biomaterials, 32(5): 1446-1453 (2010).
Mansouri et al., "Modulating the release kinetics through the control of the permeability of the layer-by-layer assembly: a review," Expert Opin Drug Deliv, 6(6): 585-597 (2009).
Martin et al., "Solubility and Kinetic Release Studies of Naproxen and Ibuprofen in Soluble Epichlorohydrin-β-cyclodextrin Polymer," Supramolecular Chemistry, 18(8): 627-631 (2006).
Martinez et al., "Single-stranded antisense siRNAs guide target RNA cleavage n RNAi," Cell, 110: 563-574 (2002).
Martino et al., "Engineering the growth factor microenvironment with fibronectin domains to promote wound and bone tissue healing," Sci Transl Med, 3(100): 100ra189 (2011).
Mathiowitz et al., "Polyanhydride Microspheres as Drug Carriers I. Hot-Melt Microencapsulation," J Controlled Release, 5: 13-22 (1987).
Mathiowitz et al., "Polyanhydride Microspheres as Drug Carriers II. Microencapsulation," J Appl Polymer Sci, 35: 755-774 (1988).
Mehrotra et al., "Time Controlled Protein Release from Layer-by-Layer Assembled Multilayer Functionalized Agarose Hydrogels," Adv Funct Mater, 20(2): 247-258 (2010).
Meinel et al., "Silk based biomaterials to heal critical sized femur defects," Bone, 39(4): 922-31 (2006).
Mendelsohn et al., "Rational design of cytophilic and cytophobic polyelectrolyte multilayer thin films," Biomacromolecules, 4(1): 96-106 (2003).
Merriam-Webster, "Definition of peel," merriam-webster.com (Accessed Dec. 18, 2018).
Michel et al., "Printing Meets Lithography: Soft Approaches to High-Resolution Patterning," IBM Journal of Research and Development, 45(5): 697-719 (2001).
Mikos et al., "Preparation and Characterization of Poly(L-Lactic Acid) Foams," Polymer, 35(5): 1068-1077 (1994).
Mikszta et al., "Improved genetic immunization via micromechanical disruption of skin-barrier function and targeted epidermal delivery," Nat Med, 8: 415-419 (2002).
Milano et al., "EGFR-targeting Drugs in Combination with Cytotoxic Agents: From Bench to Bedside, a Contrasted Reality," British Journal of Cancer, 99: 1-5 (2008).
Miller et al., "Microneedle-based sensors for medical diagnosis," J. Mater. Chem. B, 4:1379-1383 (2016).
Miller, "Cationic Liposomes for Gene Therapy," Angew Chem Int Ed, 37: 1769-1785 (1998).
Mistry et al., "Tissue engineering strategies for bone regeneration," Regenerative Medicine II. Springer, 94: 1-22 (2005).
Mizushima et al., "Methods in Mammalian Autophagy Research," Cell, 140: 313-326 (2010).
Mok et al., "Multimeric small interfering ribonucleic acid for highly efficient sequence-specific gene silencing," Nature Mater, 9: 272-278 (2010).
Montesano et al., "Test for Malignant Transformation of Rat Liver Cells in Culture: Cytology, Growth in Soft Agar, and Production of Plasminogen Activator," Journal of the National Cancer Institute, 59(6): 1651-1658 (1977).
Moor et al., "Proteolytic Activity in Wound Fluids and Tissues Derived from Chronic Venous Leg Ulcers," Wound Repair and Regeneration, 17(6): 832-839 (2009).
Moran et al., "Mixed protein carriers for modulating DNA release," Langmuir, 25(17): 10263-10270 (2009).
Morgillo et al., "Antitumor Activity of Bortezomib in Human Cancer Cells with Acquired Resistance to Anti-Epidermal Growth Factor Receptor Tyrosine Kinase Inhibitors," Lung Cancer, 71: 283-290 (2011).
Moriguchi et al., "Synthesis of Ultrathin Films of Prussian Blue by Successive Ion Adsorption Technique," Chemistry Letters, 31(3): 310-311 (2002).
Moskowitz et al., "The effectiveness of the controlled release of gentamicin from polyelectrolyte multilayers in the treatment of *Staphylococcus aureus* infection in a rabbit bone model," Biomaterials, 31(23): 6019-6030 (2010).
Mukerjee et al., "Microneedle array for transdermal biological fluid extraction and in situ analysis," Sens. Actuators A Phys., 114:267-275 (2004).
Mulligan, "The Basic Science of Gene Therapy," Science, 260: 926-932 (1993).
Murphy et al., "A Combinatorial Approach to the Delivery of Efficient Cationic Peptoid Reagents for Gene Delivery," Proc Natl Acad Sci USA, 95: 1517-1522 (1998).
Nagashima et al., "BCRP/ABCG2 levels account for the resistance to topoisomerase I inhibitors and reversal effects by gefitinib in non-small cell lung cancer," Cancer Chemotherapy and Pharmacology, 58: 594-600 (2006).
Nam et al., "Porous biodegradable polymeric scaffolds prepared by thermally induced phase separation," J Biomed MaterRes, 47(1): 8-17 (1999).
Neovius et al., "Craniofacial reconstruction with bone and biomaterials: review over the last 11 years," J Plast Reconstr Aesthet Surg, 63(10): 1615-1623 (2010).
Neve et al., "A Collection of Breast Cancer Cell Lines or the Study of Functionally Distinct Cancer Subtypes," Cancer Cell, 10: 515-527 (2006).

(56) References Cited

OTHER PUBLICATIONS

Nevins et al., "Platelet-derived growth factor stimulates bone fill and rate of attachment level gain: results of a large multicenter randomized controlled trial," J Periodontol, 76(12): 2205-2215 (2005).
Newman et al., "Natural Products as Sources of New Drugs over the Period 1981-2002," Journal of Natural Products, 66: 1022-1037 (2003).
Nguyen et al., "Extended Release Antibacterial Layer-by-Layer Films Incorporating Linear-Dendritic Block Copolymer Micelles," Chemistry of Materials, 19: 5524-5530 (2007).
Niemiec et al., "Nanoheterogeneous multilayer films with perfluorinated domains fabricated using the layer-by-layer method," Langmuir, 26(14): 11915-11920 (2010).
Notice of Allowance and Fees Due for U.S. Appl. No. 14/811,263 dated Apr. 10, 2017.
O'Donnell et al., "Preparation of Microspheres by the Solvent Evaporation Technique," Adv Drug Delivery Rev, 28: 25-42 (1997).
Oh et al., "Stem cell fate dictated solely by altered nanotube dimension," Proc Natl Acad Sci U S A, 106(7): 2130-2135 (2009).
Okada, "One-and Three-Month Release Injectable Microspheres of the LH-RH Superagonist Leuprorelin Acetate," Adv Drug Delivery Rev, 28: 43-70 (1997).
Oliva et al., "Antiproliferative Drug-Eluting Stents: Systematic Review of the Benefits and Estimate of Economic Impact," Rev Esp Cardiol, 57(7): 617-628 (2004).
Pan et al., "Cancer Immunotherapy Using a Membrane-bound Interleakin-12 with B7-1 Transmembrane and Cytoplasmic Domains," Molecular Therapy, 20(5): 927-937 (2012).
Papanas et al., "Benefit-risk assessment of becaplermin in the treatment of diabetic foot ulcers," Drug Safety: An International Journal of Medical Toxicology and Drug Experience, 33(6): 455-461 (2010).
Pareta et al., "An understanding of enhanced osteoblast adhesion on various nanostructured polymeric and metallic materials prepared by ionic plasma deposition," J Biomed Mater Res A, 92(3): 1190-1201 (2010).
Park et al., "Biodegradable polymer microneedles: fabrication, mechanics and transdermal drug delivery," J Controlled Release, 104: 51-66 (2005).
Park et al., "Osteoconductivity of hydrophilic microstructured titanium implants with phosphate ion chemistry," Acta Biomater, 5(6): 2311-2321 (2009).
Park et al., "Polymer microneedles for controlled-release drug delivery," Pharm Res, 23: 1008-1019 (2006).
Pasco et al., "Characterization of a Thermophilic L-glutamate Dehydrogenase Biosensor for Amperometric Determination of L-glutamate by Flow Injection Analysis," Biosensors & Bioelectronics, 14: 171-178 (1999).
Pashuck et al., "Designing Regenerative Biomaterial Therapies for the Clinic," Science Translational Medicine, 4(160): 160sr164 (2012).
Patil et al., "Surface-modified and internally cationic polyamidoamine dendrimers for efficient siRNA delivery," Bioconjug Chem, 19: 1396-1403 (2008).
Pawson et al., "Network Medicine," FEBS Letters, 582: 1266-1270 (2008).
Pearton et al., "Gene delivery to the epidermal cells of human skin explants using microfabricated microneedles and hydrogel formulations," Pharm Res, 25(2): 407-416 (2008).
Peer et al., "Selective gene silencing in activated leukocytes by targeting siRNAs to the integrin lymphocyte function-associated antigen-1," Proc Natl Acad Sci USA, 104(10): 4095-4100 (2007).
Peer et al., "Systemic leukocyte-directed siRNA delivery revealing cyclin D1 as an anti-inflammatory target," Science, 319: 627-630 (2008).
Peerce et al., "Polymer Films on Electrodes, Part III. Digital Simulation Model for Cyclic Voltammetry of Electroactive Polymer Film and Electrochemistry of Poly(vinylferrocene) on Platinum," J Electroanal Chem, 114: 89-115 (1980).

Perou et al., "Molecular Portraits of Human Breast Tumours," Nature, 406: 747-752 (2000).
Perry et al., "Nano- and Micro patterning of Optically Transparent, Mechanically Robust, Biocompatible Silk Fibroin Films," Advanced Materials, 20(16): 3070-3072 (2008).
Petrie et al., "The effect of integrin-specific bioactive coatings on tissue healing and implant osseointegration" Biomaterials, 29(19): 2849-2857 (2008).
Pfeifer et al., "Formulation and surface modification of poly( ester-anhydride) micro- and nanospheres," Biomaterials, 26: 117-124 (2005).
Picart et al., "Molecular Basis for the Explanation of the Exponential Growth of Polyelectrolyte Multilayers," Proc Natl Acad Sci, 99(20): 12531-12535 (2002).
Place et al., "Complexity in biomaterials for tissue engineering," Nat Mater, 8(6): 457-470 (2009).
Poerner et al., "Drug-coated Stent," Minimally Invasive Therapy & Allied Technologies, 11(4): 185-192 (2002).
Porcel et al., "From exponential to linear growth in polyelectrolyte multilayers" Langmuir, 22(9): 4376-4383 (2006).
Porcel et al., "Influence of the polyelectrolyte molecular weight on exponentially growing multilayer films in the linear regime," Langmuir, 23(4): 1898-1904 (2007).
Porter et al., "Bone tissue engineering: a review in bone biomimetics and drug delivery strategies," Biotechnology Progress, 25(6): 1539-1560 (2009).
Portin., "Layer-by-Layer Assembly of the Polyelectrolytes on Mesoporous Silicon Nanoparticles," Master's Thesis, University of Eastern Finland, Joensuu, Finland (2012).
Prausnitz et al., "Transdermal drug delivery," Nat Biotechnol, 26(11): 1261-1268 (2008).
Prausnitz, "Microneedles for transdermal drug delivery," Adv Drug Delivery Rev, 56: 581-587 (2004).
Pritchard et al., "Silk fibroin encapsulated powder reservoirs for sustained release of adenosine," Journal of Controlled Release, 144(2): 159-67 (2010).
Pruss-Ustun et al., "Introduction and methods: assessing the environmental burden of disease at national and local levels," Geneva, World Health Organization, 2003 (WHO Environmental Burden of Disease Series, No. 1).
Putnam et al., "Poly(4-hydroxy-L-proline ester): Low-Temperature Polycondensation and Plasmid DNA Complexation," Macromolecules, 32: 3658-3662 (1999).
Qiu et al., "Studies on the Drug Release Properties of Polysaccharide Multilayers Encapsulated Ibuprofen Microparticles," Langmuir, 17: 5375-5380 (2001).
Quan et al., "Stabilization of influenza vaccine enhances protection by microneedle delivery in the mouse skin," PLOS One, 4(9):e7152 (2009).
Quarles et al., "Distinct proliferative and differentiated stages of murine MC3T3-E1 cells in culture: an in vitro model of osteoblast development," J Bone Miner Res, 7(6):683-92 (1992).
Rainer et al., "Circulating Nucleic Acids and Critical Illness," Annals of the New York Science Academy of Science, 1075:271-277 (2006).
Rajan et al., "Electrochromism in the Mixed-Valence Hexacyanides. 2. Kinetics of the Reduction of Ruthenium Purple and Prussian Blue," J Phys Chem, 86: 4361-4368 (1982).
Ramaswamy et al., "Sphene ceramics for orthopedic coating applications: an in vitro and in vivo study," Acta Biomater, 5(8):3192-204 (2009).
Rao et al., "Poly(butanediol Spermate): A Hydrolytically Labile Polyester-Based Nitric Oxide Carrier," J Bioactive and Compatible Polymers, 14: 54-63 (1999).
Rausch-fan et al., "Differentiation and cytokine synthesis of human alveolar osteoblasts compared to osteoblast-like cells (MG63) in response to titanium surfaces," Dent Mater, 24(1):102-10 (2008).
Razzacki et al., "Integrated Microsystems for Controlled Drug Delivery," Advanced Drug Delivery Reviews, 56: 185-198 (2004).
Richards, et al., "R. Mode of DNA packing within bacteriophage heads," J Mol Biol, 78: 255-259 (1973).
Richert et al., "Cell interactions with polyelectrolyte multilayer films," Biomacromolecules, 3(6):1170-8 (2002).

(56) References Cited

OTHER PUBLICATIONS

Roach et al., "Interpretation of protein adsorption: surface-induced conformational changes," J Am Chem Soc, 127(22):8168-73 (2005).
Roach et al., "Modern biomaterials: a review—bulk properties and implications of surface modifications," J Mater Sci Mater Med, 18(7):1263-77 (2007).
Roberts et al., "Preliminary Biological Evaluation of Polyamidoamine (P AMAM) Starburst TM Dendrimers," J Biomed Mater Res, 30: 53-65 (1996).
Robin et al., "The Color and Electronic Configurations of Prussian Blue," Inorg Chem, 1(2): 337-342 (1962).
Rockwood et al., "Materials fabrication from *Bombyx mori* silk fibroin," Nature Protocols, 6: 1612-1631 (2011).
Rohanizadeh et al., "Gelatin Sponges (Gelfoam®) as a scaffold for Osteoblasts", J Mater Sci Mater Med, 19:1173-1182 (2008).
Runge et al., "Paramagnetic NMR contrast agents. Development and evaluation," Investigative Radiology, 19(5): 408-415 (1984).
Rusnak et al., "Assessment of Epidermal Growth Factor Receptor (EGFR, ErbB1) and HER2 (ErbB2) Protein Expression Levels and Response to Lapatinib (Tykerb®, GW572016) in an Expanded Panel of Human Normal and Tumour Cell Lines," Cell Proliferation, 40: 580-594 (2007).
Sachs et al., "Casual Protein-Signaling Networks Derived from Multiparameter Single-Cell Data," Science, 308: 523-529 (2005).
Saha et al., "Designing synthetic materials to control stem cell phenotype," Curr Opin Chem Biol,11(4):381-7 (2007).
Sallusto et al., "Central memory and effector memory T cell subsets: Function, generation, and maintenance," Annu Rev Immunol, 22:145-163, (2004).
Samuel et al., "Osteoconductive protamine-based polyelectrolyte multilayer functionalized surfaces," Biomaterials, 32:1491-1502 (2011).
Sanford, "The Biolistic Process," Trends Biotechnol, 6: 299-302 (1988).
Santin et al., "In vitro evaluation of the inflammatory potential of the silk fibroin," Journal of Biomedical Materials Research, 46(3): 382-389 (1999).
Santini et al., "Microchips as Controlled Drug-Delivery Devices," Angew Chem Int Ed, 39: 2396-2407 (2000).
Santini et al., "Microchips for Drug Delivery," Abstracts of Meeting of the American Chemical Society, 219(174): U34-U34 (2000).
Sapi et al., "Ets-2 Transdominant Mutant Abolishes Anchorage-independent Growth and Macrophage Colony-stimulating Factor-stimulated Invasion by BT20 Breast Carcinoma Cells," Cancer Research, 58: 1027-1033 (1998).
Sato et al., "Layered Assemblies Composed of Sulfonated Cyclodextrin and Poly(allylamine)," Colloid & Polymer Science, 282: 287-290 (2004).
Schaefer et al., "In vivo nuclear magnetic resonance imaging of myocardial perfusion using the paramagnetic contrast agent manganese gluconate," Journal of The American College of Cardiology, 14(2): 472-480 (1989).
Schaffer et al., "Vector Unpacking as a Potential Barrier for Receptor-Mediated PolyplexGene Delivery," Biotechnol Bioeng, 61: 598-606 (2000).
Schechter et al., "The Neu Oncogene: an Erb-8-related Gene Encoding a 185,000-Mr Tumour antigen," Nature, 312: 513-516 (1984).
Schlenoff, "Retrospective on the future of polyelectrolyte multilayers" Langmuir 25(24):14007-10 (2009).
Schmidt et al., "Electrochemically controlled swelling and mechanical properties of a polymer nanocomposite," ACS Nano, 3(8):2207-16 (2009).
Schmitz et al., "The Critical Size Defect as an Experimental-Model for Craniomandibulofacial Nonunions," Clinical Orthopaedics and Related Research, 205: 299-308 (1986).
Schuler, "Decomposable Hollow Biopolymer-Based Capsules," Biomacromolecules, 2: 921-926 (2001).
Schwarz et al., "Potential of chemically modified hydrophilic surface characteristics to support tissue integration of titanium dental implants," J Biomed Mater Res B Appl Biomater, 88(2):544-57 (2009).
Schweikl et al., "Triethylene Glycol Dimethacrylate Induces Large Deletions in the Hprt Gene of V79 Cells," Mutat Res, 438: 71-78 (1999).
Seeman, "Nanomaterials based on DNA," Annu Rev Biochem, 79:65-87 (2010).
Semple et al., "Rational design of cationic lipids for siRNA delivery," Nature Biotechnol, 28:172-176 (2010).
Sengupta et al., "Temporal Targeting of Tumor Cells and Neovasculature with a Nanoscale Delivery System," Nature, 436: 568-572 (2005).
Seo et al., "Effect of the layer-by-layer (LbL) deposition method on the surface morphology and wetting behavior of hydrophobically modified PEO and PAA LbL films," Langmuir, 24(15):7995-8000 (2008).
Sevecka et al., "State-based Discovery: A Multidimensional Screen for Small-Molecule Modulators of EGF Signaling," Nature Methods, 3(10): 825-831 (2006).
Seyhan et al., "RNA Interference from Multimeric shRNAs Generated by Rolling Circle Transcription," Oligonucleotides, 16(4): 353-363 (2006).
Shah et al., "Surface-Mediated Bone Tissue Morphogenesis from Tunable Nanolayered Implant Coatings," Science Translational Medicine, 5, 191ra83 (2013).
Shakeel et al., "Peptide nucleic acid (PNA)—a review," J. Chem. Technol. Biotechnol., 81:892-899 (2006).
Shi et al., "The epidermal growth factor tyrosine kinase inhibitor AG1478 and erlotinib reverse ABCG2-meditated drug resistance," Oncology Reports, 21: 483-489 (2008).
Shiratori et al., "pH-Dependent Thickness Behavior of Sequentially Adsorbed Layers of Weak Polyelectrolytes," Macromolecules, 33: 4213-4219 (2000).
Shkula et al., "Tunable Vancomycin Releasing Surfaces for Biomedical Applications," Small Nano Micro, 21(6): 2392-2404 (2010).
Shreve et al., "Monoclonal antibodies labeled with polymeric paramagnetic ion chelates," Magnetic Resonance in Medicine , 3(2): 336-340 (1986).
Shukla et al., "Controlling the release of peptide antimicrobial agents from surfaces," Biomaterials, 31(8):2348-2357 (2010).
Shutava et al., "Layer-by-Layer-Coated Gelatin Nanoparticles as a Vehicle for Delivery of Natural Polyphenols," ACS Nano, 3(7):1877-85 (2009).
Singh et al., "Cationic Microparticles: A Potent Delivery System for DNA Vaccines," Proc Natl Acad Sci USA, 97: 811-816 (2000).
Slamon et al., "Human Breast Cancer: Correlation of Relapse and Survival with Amplification of the HER-2/neu Oncogene," Science, 235: 177-182 (1987).
Smiell et al., "Efficacy and safety of becaplermin (recombinant human platelet-derived growth factor-BB) in patients with nonhealing, lower extremity diabetic ulcers: a combined analysis of four randomized studies," Wound Repair Regen, 7(5): 335-346 (1999).
Smith et al., "Enhancing DNA vaccination by sequential injection of lymph nodes with plasmid vectors and peptides," Vaccine, 27:2603-2615 (2009).
Smith et al., "Layer-by-Layer Platform Technology for Small-Molecule Delivery," Angew Chem Int Ed, 48: 8974-8977 (2009).
Smith et al., "Multivalent immunity targeting tumor-associated antigens by intra-lymph node DNA-prime ,peptide-boost vaccination," Cancer Gene Ther, 18:63-76 (2011).
Smith et al., "Silicon microneedle array for minimally invasive human health monitoring," Proc. SPIE 10491, Microfluidics, BioMEMS, and Medical Microsystems XVI, 1049102 (2018).
Sofia et al., "Functionalized silk-based biomaterials for bone formation," Journal of Biomedical Materials Research, 54(1): 139-148 (2001).
Song et al., "Growth of Endothelial Cell on the Surface of Intravascular Sent Material: Bionic Construction of Bioactive Extracellular Matrix," Journal of clinical Rehabilitative Tissue Engineering Research, 13(43): 8425-8431 (2009).

(56) References Cited

OTHER PUBLICATIONS

Sordella et al., "Gefitinib-Sensitizing EGFR Mutations in Lung Cancer Activate Anti-Apoptotic Pathways," Science, 305: 1163-1167 (2004).
Spicer et al., "Evaluation of bone regeneration using the rat critical size calvarial defect," Nature protocols, 7(10): 1918-1929 (2012).
Stevens, "Biomaterials for bone tissue engineering," Materials Today, 11(5): 18-25 (2008).
Strathmann, "Membrane separation processes: current relevance and future opportunities," AIChE Journal, 47(5): 1077-1087 (2001).
Stubbs et al, "The interaction of thrombin with fibrinogen," Eur J Biochem, 206:187-195 (1992).
Su et al., "Layer-by-layer-assembled multilayer films for transcutaneous drug and vaccine delivery," ACS Nano, 3: 3719-3729 (2009).
Subramanian et al., "Gene Set Enrichment Analysis: A Knowledge-based Approach for Interpreting Genome-wide Expression Profiles," Proc Natl Acad Sci USA, 102(43): 15545-15550 (2005).
Sulaiman et al., "Chemically Modified Hydrogel-Filled Nanopores: A Tunable Platform for Single-Molecule Sensing," Nano Lett., 18:6084-6093 (2018).
Sulaiman et al., "Subnanomolar Detection of Oligonucleotides through Templated Fluorogenic Reaction in Hydrogels: Controlling Diffusion to Improve Sensitivity," Angew. Chem. Int., 56:1-6 (2017).
Sullivan et al., "Dissolving polymer microneedle patches for influenza vaccination," Nat Med, 16:915-920 (2010).
Sullivan et al., "Minimally invasive protein delivery with rapidly dissolving polymer microneedles," Adv Mater, 20:933-938 (2008).
Sun et al., "Activation of Multiple Proto-oncogenic Tyrosine Kinases in Breast Cancer via Loss of the PTPN12 Phosphatase," Cell, 144: 703-718 (2011).
Tang et al., "Adhesion and Endothelialization of Endothelial Cells on the Surface of Endovascular Stents by the Novel Rotational Culture of Cells," Applied Surface Science, 255: 315-319 (2008).
Tang et al., "In Vitro Gene Delivery by Degraded Polyamidoamine Dendrimers," Bioconjugate Chem, 7:703-714 (1996).
Taratula et al. "Surface-engineered targeted PPI dendrimer for efficient intracellular and intratumoral siRNA delivery," J Control. Release, 140:284-293 (2009).
Tetko et al., "Virtual Computational Chemistry Laboratory-design and Description," Computer-Aided Mol Des, 19: 453-463 (2005).
Thompson et al., "Biochemical functionalization of polymeric cell substrata can alter mechanical compliance," Biomacromolecules, 7(6):1990-5 (2006).
Thompson et al., "Tuning compliance of nanoscale polyelectrolyte multilayers to modulate cell adhesion," Biomaterials, 26(34):6836-45 (2005).
Tijsterman et al., "The genetics of RNA silencing," Annu Rev Genet, 36:489-519 (2002).
Toniolo et al., "Protamines. II. Circular dichroism study of the three main components of clupeine," Biochim Biophys Acta, 576(2):429-39 (1979).
Trubetskoy et al., "Layer-by-layer deposition of oppositely charged polyelectrolytes on the surface of condensed DNA particles," Nucleic Acids Res, 27:3090-3095 (1999).
Turner et al., "ABCG2 Expression, Function, and Promoter Methylation in Human Multiple Myeloma," Blood, 108(12): 3881-3889 (2006).
Uhrich et al., "Polymeric Systems for Controlled Drug Release," Chem Rev, 99: 3181-3198 (1999).
Uhrich, "Hyperbranched Polymers for Drug Delivery," Trends Polym Sci, 5: 388-393 (1997).
van de Wetering et al., "Structure-Activity Relationships of Water-Soluble Cationic Methacrylate/Methacrylamide Polymers for Nonviral Gene Delivery," Bioconjugate Chem, 10: 589-597 (1999).
Vazquez et al., "Variation of polyelectrolyte film stiffness by photo-cross-linking: a new way to control cell adhesion," Langmuir, 25(6):3556-63 (2009).
Vittal et al., "Surfactant Promoted Enhancement on Electrochemical and Electrochromic Properties of Film and Prussian Blue and Its Analogs," Journal of the Electrochemical Society, 146(2): 786-793 (1999).
Vo et al., "Strategies for controlled delivery of growth factors and cells for bone regeneration," Adv Drug Deliv Rev, 64(12): 1292-1309 (2012).
Vrdoljak et al., "Induction of broad immunity by thermostabilised vaccines incorporated in dissolvable microneedles using novel fabrication methods," J Control Release, 225:192-204 (2016).
Wang et al., "A Novel Biodegradable Gene Carrier Based on Polyphosphoester," J Am Chem Soc, 123: 9480-9481 (2001).
Wang et al., "Minimally Invasive Extraction of Dermal Interstitial Fluid for Glucose Monitoring Using Microneedles," Diabetes Technol. Ther., 7:131-141 (2005).
Wang et al., "Precise Microinjection into Skin Using Hollow Microneedles," J Invest Dermatol, 126:1080-1087 (2006).
Warner et al., "Nonsteroid Drug Selectives for Cyclo-Oxygenase-1 Rather Than Cyclo-Oxygenase-2 are Associated with Human Gastrointestinal Toxicity: A Full in vitro Analysis," Proc Natl Acad Sci USA, 96: 9966 (1999).
Watts et al., "Long-Term Use of Bisphosphonates in Osteoporosis," J Clin Endocr Metab, 95(4): 1555-1565 (2010).
Wick et al., "Profound CD8+ T cell immunity elicited by sequential daily immunization with exogenous antigen plus the TLR3 agonist poly(I:C)," Vaccine 29: 984-993 (2011).
Wikipedia, Heparin, accessed Oct. 15, 2014, pp. 1-18.
Will et al., "Porous ceramic bone scaffolds for vascularized bone tissue regeneration," Journal of Materials Science, 19(8): 2781-2790 (2008).
Winer et al., "Optimizing Treatment of 'Triple-Negative,'" Breast Cancer. SABCS 2007: Improvising Outcomes in Advanced and Meta-static Breast Cancer (2007).
Woeblecke et al., "Reversal of Breast Cancer Resistance Protein-Mediated Drug Resistance by Tryoprostatin A," International Journal of Cancer, 107: 721-728 (2003).
Wood et al., "A Unique Structure for Epidermal Growth Factor Receptor Bound to GW572016 (Lapatinib): Relationships Among Protein Conformation, Inhibitor Off-Rate, and Receptor Activity in Tumor Cells," Cancer Research, 64: 6652-6659 (2004).
Wood et al., "Controlling Interlayer Diffusion to Achieve Sustained, Multiagent Delivery from Layer-by-Layer Thin Films," Proc Natl Acad Sci USA, 103(27): 10207-10212 (2006).
Wood et al., "Tunable drug release from hydrolytically degradable layer-by-layer thin films," Langmuir, 21(4):1603-9 (2005).
Woodruff et al., "Bone tissue engineering: from bench to bedside," Materials Today, 15(10): 430-435 (2012).
Yoon et al., "Activation of p38 Mitogen-Activated Protein Kinase Is Required for Death Receptor-Independent Caspase-8 Activation and Cell Death in Response to Sphingosine," Molecular Cancer Research, 7(3): 361-370 (2009).
Zauner et al., "Polylysine-Based Transfection Systems Utilizing Receptor-Mediated Delivery," Adv Drug Del Rev, 30: 97-113 (1998).
Zhang et al., "In Vitro Observations of Self-Assembled ECM-Mimetic Bioceramic; Nanoreservoir Delivering rFN/CDH to Modulate Osteogenesis", Biomaterials, 33(30): 7468-7477 (2012).
Zhang et al., "Multilayered Thin Films that Sustain the Release of Functional DNA under Physiological Conditions," Langmuir, 20(19): 8015-8021 (2004).
Zhang et al., "Structure/property relationships in erodible multilayered films: influence of polycation structure on erosion profiles and the release of anionic polyelectrolytes," Langmuir, 22:239-245 (2006).
Zheng et al., "Controlling cell attachment selectively onto biological polymer-colloid templates using polymer-on-polymer stamping," Langmuir, 20(17):7215-22 (2004).
Zhou et al., "Preparation of Poly(L-serine) ester): A Structural Analogue of Conventional Poly(L-serine)," Macromolecules, 23: 3399-3406 (1990).
Dash et al., "The influence of size and charge of chitosan/polyglutamic acid hollow spheres on cellular internalization, viability, and blood compatibility," Biomaterials, 31: 8188-8197 (2010).

(56) References Cited

OTHER PUBLICATIONS

Krasnici et al., "Effect of the Surface Charge of Liposomes on Their Update by Angiogenic Tumor Vessels," Int J Cancer, 105: 561-567 (2003).
Ambros, "The functions of animal microRNAs," Nature, 431:350-355 (2004).
Bakhtiar, "Peptide nucleic acids: deoxyribonucleic acid mimics with a peptide backbone," Biochemical Education, 26:277-280 (1998).
Bartel, "MicroRNAs: Genomics, Review Biogenesis, Mechanism, and Function," Cell, 116:281-297 (2004).
Brock et al., "Liquid biopsy for cancer screening, patient stratification and monitoring," Transl Cancer Res, 4(3):280-290 (2015).
Chan et al., "Cell-free nucleic acids in plasma, serum and urine: a new tool in molecular diagnosis," Ann. Clin. Biochem., 40:122-130 (2003).
Chen et al., "Characterization of microRNAs in serum: a novel class of biomarkers for diagnosis of cancer and other diseases," Cell Res., 18:997-1006 (2008).
Croce, "Causes and consequences of microRNA dysregulation in cancer," Nat. Rev. Genet., 10(10):704-714 (2009).
Crowley et al., "Liquid biopsy: monitoring cancer-genetics in the blood," Nature Reviews Clinical Oncology, 10:472-484 (2013).
DeMuth et al., "Composite Dissolving Microneedles for Coordinated Control of Antigen and Adjuvant Delivery Kinetics in Transcutaneous Vaccination," Adv. Funct. Mater., 23:161-172 (2013).
DeMuth et al., "Nano-layered Microneedles for Transcutaneous Delivery of Polymer Nanoparticles and Plasmid DNA," Adv. Mater., 22:4851-4856 (2010).
DeMuth et al., "Releasable Layer-by-Layer Assembly of Stabilized Lipid Nanocapsules on Microneedles for Enhanced Transcutaneous Vaccine Delivery," ACS Nano, 6(9):8041-8051 (2012).
DeMuth et al., "Vaccine delivery with microneedle skin patches in nonhuman primates," Nat. Biotechnol., 31(12):1082-1085 (2013).
Halvorsen et al., "Profiling of microRNAs in tumor interstitial fluid of breast tumors—a novel resource to identify biomarkers for prognostic classification and detection of cancer," Mol. Oncol., 11:220-234 (2017).
Huang et al., "Liquid biopsy utility for the surveillance of cutaneous malignant melanoma patients," Mol. Oncol., 10:450-463 (2016).
Ito et al., "Therapeutic Drug Monitoring of Vancomycin in Dermal Interstitial Fluid Using Dissolving Microneedles," Inter. J. Med. Sci., 13(4):271-276 (2016).
Jensen et al., "Characterization of Alginates by Nuclear Magnetic Resonance (NMR) and Vibrational Spectroscopy (IR, NIR, Raman) in Combination with Chemometrics," Methods Mol. Biol., 1308:347-363 (2015).
Liu et al., "Porous polymer microneedles with interconnecting microchannels for rapid fluid transport," RSC Adv., 6:48630-48635 (2016).
Lu et al., "MicroRNA expression profiles classify human cancers," Nature, 435:834-838 (2005).
Mandal et al. "Cell and fluid sampling microneedle patches for monitoring skin-resident immunity." Science Translational Medicine 10(467):eaar2227 (2018).
Meltzer, "Small RNAs with big impacts," Nature, 435:745-746 (2005).
Metcalf et al., "Amplification-Free Detection of Circulating microRNA Biomarkers from Body Fluids Based on Fluorogenic Oligonucleotide-Templated Reaction between Engineered Peptide Nucleic Acid Probes: Application to Prostate Cancer Diagnosis," Anal. Chem., 88:8091-8098 (2016).
Miller et al., "Extraction and biomolecular analysis of dermal interstitial fluid collected with hollow microneedles," Commun. Biol., 1:173 (2018).

Nielsen et al., "An Introduction to Peptide Nucleic Acid," Current Issues Molec. Biol., 1(2):89-104 (1999).
Ono et al., "A direct plasma assay of circulating microRNA-210 of hypoxia can identify early systemic metastasis recurrence in melanoma patients," Oncotarget, 6(9):7053-7064 (2015).
Ono et al., "Circulating microRNA Biomarkers as Liquid Biopsy for Cancer Patients: Pros and Cons of Current Assays," J. Clin. Med., 4:1890-1907 (2015).
Presolski et al., "Copper-Catalyzed Azide-Alkyne Click Chemistry for Bioconjugation," Curr. Protoc. Chem. Biol., 3(4):153-162 (2011).
Romanyuk et al., "Collection of Analytes from Microneedle Patches," Anal. Chem., 86:10520-10523 (2014).
Saito et al., "Epigenetic Activation of Tumor Suppressor MicroRNAs in Human Cancer Cells," Cell Cycle, 5(19):2220-2222 (2006).
Samant et al., "Mechanisms of sampling interstitial fluid from skin using a microneedle patch," Proc. Natl Acad. Sci. U.S.A., 115(18):4583-4588 (2018).
Siravegna et al., "Integrating liquid biopsies into the management of cancer," Nature Reviews Clinical Oncology, 14:531-548 (2017).
Sita-Lumsden et al., "Circulating microRNAs as potential new biomarkers for prostate cancer," British Journal of Cancer, 108:1925-1930 (2013).
Swarup et al., "Circulating (cell-free) nucleic acids—A promising, non-invasive tool for early detection of several human diseases," FEBS Letters, 581:795-799 (2007).
Ulivi et al., "miRNAs as Non-Invasive Biomarkers for Lung Cancer Diagnosis," Molecules, 19:8220-8237 (2014).
Ventrelli et al., "Microneedles for Transdermal Biosensing: Current Picture and Future Direction," Adv. Healthc. Mat., 4:2606-2640 (2015).
Volinia et al., "Breast cancer signatures for invasiveness and prognosis defined by deep sequencing of microRNA," Proc. Nat. Acad. Sci. USA, 109(8):3024-3029 (2012).
Weber et al., "The MicroRNA Spectrum in 12 Body Fluids," Clin. Chem., 56(11):1733-1741 (2010).
Sulaiman et al., "Hydrogel-coated microneedle arrays for minimally-invasive sampling and sensing of specific circulating nucleic acids from skin interstitial fluid," ACS Nano, 13(8): 9620-9628 (2019).
Ellis et al., "Electrochromism in the Mixed-Valence Hexacyanides. 1. Voltammetric and Spectral Studies of the Oxidation and Reduction of Thin Films of Prussian Blue," J Phys Chem, 85: 1225-1231 (1981).
Feiler et al., "Adsorption and viscoelastic properties of fractionated mucin (BSM) and bovine serum albumin (BSA) studied with quartz crystal microbalance (QCM-D)," J Colloid Interface Sci, 315(2):475-81 (2007).
Kargina et al., "Self-Splitting Water-Soluble Ionogenic Polymers" Vysokomol. Soedin. Seriya A, 28: 1139-1144, 1986. (with English abstract).
Morris et al., "Small interfering RNA-induced transcriptional gene silencing in human cells," Science, 305: 1289-1202 (2004).
Wang et al., "Synthesis and evaluation of water-soluble polymeric bone-targeted drug delivery systems," Bioconjugate Chemistry 14(5): 853-859 (2003).
Written Opinion for PCT/US06/04295, date of mailing: Oct. 2, 2006.
Written Opinion for PCT/US08/66948 dated Aug. 23, 2008.
Written Opinion for PCT/US11/35057, dated Feb. 8, 2012.
Written Opinion for PCT/US2002/34191 mailed Jun. 17, 2003.
Written Opinion for PCT/US2014/018284, dated Jul. 30, 2014.
Written Opinion for PCT/US2014/022107, dated Jun. 5, 2014.
Written Opinion for PCTUS2007/69937 dated Aug. 13, 2008.
Written Opinion for PCTUS2007/69964 dated: Oct. 29, 2007.
Yang et al., "A New Approach to Identifying Genotoxic Carcinogens: p53 Induction as an Indicator of Genotoxic Damage," Carcinogenesis, 19:1117-1125 (1998).

* cited by examiner

PEPTIDE NUCLEIC ACID FUNCTIONALIZED HYDROGEL MICRONEEDLES FOR SAMPLING AND DETECTION OF INTERSTITIAL FLUID NUCLEIC ACIDS

RELATED APPLICATION(S)

This application claims the benefit of U.S. Provisional Application No. 62/854,475, filed on May 30, 2019. The entire teachings of the above application are incorporated herein by reference.

GOVERNMENT SUPPORT

This invention was made with government support under Grant No. W911NF-13-D-0001 awarded by the Army Research Office (ARO). The government has certain rights in the invention.

BACKGROUND OF THE INVENTION

Minimally-invasive technologies that can sample and detect cell-free nucleic acid biomarkers from liquid biopsies have recently emerged as clinically useful for early diagnosis and longitudinal monitoring of a broad range of pathologies, including cancer. Although blood has been so far the most commonly interrogated body fluid, skin interstitial fluid has been mostly overlooked despite containing the same broad variety of molecular biomarkers originating from cells and surrounding blood capillaries. Minimally-invasive technologies have emerged as a method to sample this fluid in a pain-free manner and often take the form of microneedle patches.

Liquid biopsies have the potential to revolutionize the way patients are screened, treated and monitored, all of which are key drivers of precision medicine (G. Siravegna, S. Marsoni, S. Siena, A. Bardelli, *Nat. Rev. Clin. Oncol.* 2017, 14, 531-548; E. Crowley, F. Di Nicolantonio, F. Loupakis, A. Bardelli, *Nat. Rev. Clin. Oncol.* 2013, 10, 472-484; S. Ono, S. Lam, M. Nagahara, D. S. B. Hoon, *J. Clin. Med.* 2015, 4, 1890-1907; G. Brock, E. Castellanos-Rizaldos, L. Hu, C. Coticchia, J. Skog, *Transl. Cancer Res.* 2015, 4, 280-290.) Although affordable full genome sequencing may help identify individuals at risk of developing specific pathologies, snapshots provided by point-of-care testing through simple technologies that are both low-cost and highly automated remain essential for public screening or personalized longitudinal monitoring. Circulating, cell-free nucleic acids (cfNAs) in liquid biopsies have been reported as predictive, diagnostic and prognostic biomarkers for a broad range of conditions, most notably cancer (T. H. Rainer, N. Y. L. Lam, *Ann. N. Y. Acad. Sci.* 2006, 1075, 271-277; M. Fleischhacker, B. Schmidt, *Biochim. Biophys. Acta* 2007, 1775, 181-232; V. Swamp, M. R. Rajeswari, *FEBS Lett.* 2007, 581, 795-799; E. Danese, M. Montagnana, C. Fava, G. C. Guidi, *Semin. Thromb. Hemost.* 2014, 40, 766-773). Among them microRNAs (or miRs) (D. P. Bartel, Cell 2004, 116, 281-297; V. Ambros, *Nature* 2004, 431, 350-355; P. S. Meltzer, *Nature* 2005, 435, 745-746; Y. Saito, P. A. Jones, Cell Cycle 2006, 5, 2220-2222; C. M. Croce, *Nat. Rev. Genet.* 2009, 10, 704-714; W. C. S. Cho, *Int. J. Biochem. Cell Biol.* 2010, 42, 1273-1281), a class of non-coding RNAs 19-25 nucleotides in length, hold the greatest promise as either individual biomarkers or in combinations (J. Lu, G. Getz, E. A. Miska, E. Alvarez-Saavedra, J. Lamb, D. Peck, A. Sweet-Cordero, B. L. Ebert, R. H. Mak, A. A. Ferrando, J. R. Downing, T. Jacks, H. R. Horvitz, T. R. Golub, *Nature* 2005, 435, 834-838; S. Volinia, M. Galasso, M. E. Sana, T. F. Wise, J. Palatini, K. Huebner, C. M. Croce, *Proc. Nat. Acad. Sci. USA* 2012, 109, 3024-3029; A. Sita-Lumsden, D. A. Dart, J. Waxman, C. Bevan, *Br. J. Cancer* 2013, 108, 1925-1930; P. Ulivi, W. Zoli, *Molecules* 2014, 19, 8220; A. R. Halvorsen, ø. Helland, P. Gromov, V. T. Wielenga, M. L. M. Talman, N. Brunner, V. Sandhu, A. L. Børresen-Dale, I. Gromova, V. D. Haakensen, *Mol. Oncol.* 2017, 11, 220-234). Hence, there is a growing demand for sensing technologies that can detect specific nucleic acids in biological fluids and that can be implemented in the clinic.

Peptide nucleic acids (PNAs) recently emerged as promising probes for nucleic acid detection. PNAs are class of oligonucleotide mimics wherein the entire deoxyribose phosphate backbone has been replaced by a chemically different, structurally homomorphous backbone composed of (2-aminoethyl)glycine units. The synthetic backbone provides PNA with unique hybridization characteristics. Unlike DNA and RNA, the PNA backbone is not charged. Consequently, there is no electrostatic repulsion when PNAs hybridize to its target nucleic acid sequence, giving a higher stability to the PNA-DNA or PNA-RNA duplexes than the natural homo- or heteroduplexes. In addition, selective hybridization of PNA to DNA is less tolerant of base pair mismatches than DNA-DNA hybridization.

A further advantage of PNAs is that they are less susceptible to enzymatic degradation and are more stable than nucleic acid in various chemical environments.

PNAs can be synthesized to target particular nucleic acid sequences, thus providing an opportunity for highly selective nucleic acid analysis. Peptide Nucleic Acids (PNAs) are known per se and can be prepared in accordance with any of the various procedures referred to in B. Hyrup, P. E. Nielsen, *Bioorganic & Medicinal Chemistry,* 1996, 4, 5-23. Examples of PNA syntheses are disclosed, for example, in U.S. Pat. Nos. 5,539,083 and 6,433,134, each of which is incorporated herein by reference in its entirety.

In summary, PNAs can be used as stable, efficient, and selective probes for detection and isolation of nucleic acids, including cfNAs.

Research on cfNAs has so far been limited almost exclusively to those found in blood or urine (J. A. Weber, D. H. Baxter, S. Zhang, D. Y. Huang, K. H. Huang, M. J. Lee, D. J. Galas, K. Wang, *Clin. Chem.* 2010, 56, 1733-1741; X. Chen, Y. Ba, L. Ma, X. Cai, Y. Yin, K. Wang, J. Guo, Y. Zhang, J. Chen, X. Guo, Q. Li, X. Li, W. Wang, Y. Zhang, J. Wang, X. Jiang, Y. Xiang, C. Xu, P. Zheng, J. Zhang, R. Li, H. Zhang, X. Shang, T. Gong, G. Ning, J. Wang, K. Zen, J. Zhang, C.-Y. Zhang, *Cell Res.* 2008, 18, 997-1006; A. K. Chan, R. W. Chiu, Y. D. Lo, *Ann. Clin. Biochem.* 2003, 40, 122-130; O. E. Bryzgunova, T. E. Skvortsova, E. V. Kolesnikova, A. V. Starikov, E. Y. Rykova, V. V. Vlassov, P. P. Laktionov, *Ann. N. Y. Acad. Sci.* 2006, 1075, 334-340). However, recent experimental evidence suggests that all species of RNA (including miRs) previously found in blood are also present, in similar proportions, within interstitial fluid (ISF) (P. R. Miller, R. M. Taylor, B. Q. Tran, G. Boyd, T. Glaros, V. H. Chavez, R. Krishnakumar, A. Sinha, K. Poorey, K. P. Williams, S. S. Branda, J. T. Baca, R. Polsky, *Commun. Biol.* 2018, 1, 173), validating this type of bodily fluid as a greatly overlooked source of biomarkers for personalized medicine. Surrounding cells within a tissue, ISF serves as an exchange medium between blood plasma and cells and contains a combination of molecular constituents found in both sources. Skin ISF is found within several hundred microns of the skin surface, primarily in the connective tissue dermis where only few capillary beds and pain receptors reside. It can therefore be sampled in a pain-free manner, without any risk of blood contamination. This contrasts with blood drawing techniques that can be invasive (venous blood) or result in poor quality samples (fingerstick capillary blood).

Additionally, sampling ISF can allow one to determine localized concentrations of biomarkers, thus providing information that is particularly valuable in the cases of certain infections or malignancies. In those cases, the necessary information about the local biomarker concentrations cannot be determined through blood or urine analysis.

Minimally-invasive technologies for skin ISF sampling have emerged that are based on compact patches of microneedles (MNs) (C. Kolluru, M. Williams, J. Chae, M. R. Prausnitz, *Adv. Healthc. Mater.* 2019 8, e1801262; P. P. Samant, M. R. Prausnitz *Proc. Natl Acad. Sci. U.S.A.* 2018, 115, 4583-4588; P. R. Miller, R. J. Narayan, R. Polsky, *J. Mater. Chem.* B 2016, 4, 1379-1383; L. Ventrelli, L. Marsilio Strambini, G. Barillaro, *Adv. Healthc. Mat.* 2015, 4, 2606-2640; B. Chua, S. P. Desai, M. J. Tierney, J. A. Tamada, A. N. Jina, *Sens. Actuators A Phys.* 2013, 203, 373-381; Y. Ito, Y. Inagaki, S. Kobuchi, K. Takada, T. Sakaeda, *Inter. J. Med. Sci.* 2016, 13, 271; E. V. Mukerjee, S. D. Collins, R. R. Isseroff, R. L. Smith, *Sens. Actuators A Phys.* 2004, 114, 267-275; P. M. Wang, M. Cornwell, M. R. Prausnitz, *Diabetes Technol. Ther.* 2005, 7, 131-141). They are typically made of an array of microscale solid, porous or hollow needles from materials such as glass, metal, silicon or other polymers (A. V. Romanyuk, V. N. Zvezdin, P. Samant, M. I. Grenader, M. Zemlyanova, M. R. Prausnitz, *Anal. Chem.* 2014, 86, 10520-10523; L. Liu, H. Kai, K. Nagamine, Y. Ogawa, M. Nishizawa, *RSC Adv.* 2016, 6, 48630-48635). Hollow needles were designed to create pathways for ISF extraction via capillary force or vacuum-induced suction. They represent useful alternatives to invasive sampling technologies traditionally based on microdialysis and requiring tubing implantation under local anesthetics. Current limitations of many of the MN patches engineered so far include low sampling capacity (<2 µL) and/or long sampling times (e.g. >1 h to sample enough ISF volumes for subsequent biomarker analysis). In addition, there has been no report of MNs engineered to sample and detect specific nucleic acid biomarkers from skin ISF. So far, MN were at best used for sampling and releasing total skin ISF and circulating nucleic acids detected after heavy sample processing and PCR-based analysis (R. L. Smith, S. D. Collins, J. Duy, T. D. Minogue, *Proc. SPIE* 2018, 10491, doi: 10.1117/12.2299264).

SUMMARY OF THE INVENTION

The present disclosure relates to a device for detecting an analyte, comprising a base, and a plurality of microneedles attached to the base, wherein: each microneedle has an outer surface; and the outer surface of at least one microneedle is coated with a composition comprising at least one polymer and least one first Peptide Nucleic Acid (PNA).

The present disclosure relates to a method of detecting an analyte in interstitial fluid (ISF) of a subject, comprising: contacting the subject with the device of the disclosure, exposing the device to the ISF of the subject; detaching the device from the subject; and measuring an intensity of the detectable signal.

The present disclosure relates to a method of detecting an analyte in interstitial fluid (ISF) of a subject, comprising: contacting the subject with the device of the disclosure, and exposing the device to the ISF of the subject.

The present disclosure additionally relates to a method of detecting an analyte in interstitial fluid (ISF) of a subject, comprising: contacting the subject with the device; exposing the device to the ISF of the subject; detaching the device from the subject; eluting the analyte from the device; and exposing the analyte to a detection agent, wherein the detection agent binds to the analyte.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present disclosure relates to a sampling and sensing device comprising microneedles that are coated with an alginate-peptide nucleic acid (PNA) hybrid material for sequence-specific sampling, isolation and detection of nucleic acid biomarkers from skin interstitial fluid. Characterized by fast sampling kinetics and large sampling capacity (~6.5 µL in 2 min), this platform technology also enables for the first time the detection of specific nucleic acid biomarkers either on the patch itself or in solution after light-triggered release from the hydrogel. Considering the emergence of cell-free nucleic acids in bodily fluids as clinically informative biomarkers, platform technologies that can detect them in an automated and minimally invasive fashion have great potential for personalized diagnosis and longitudinal monitoring of patient-specific disease progression.

Figure 1:
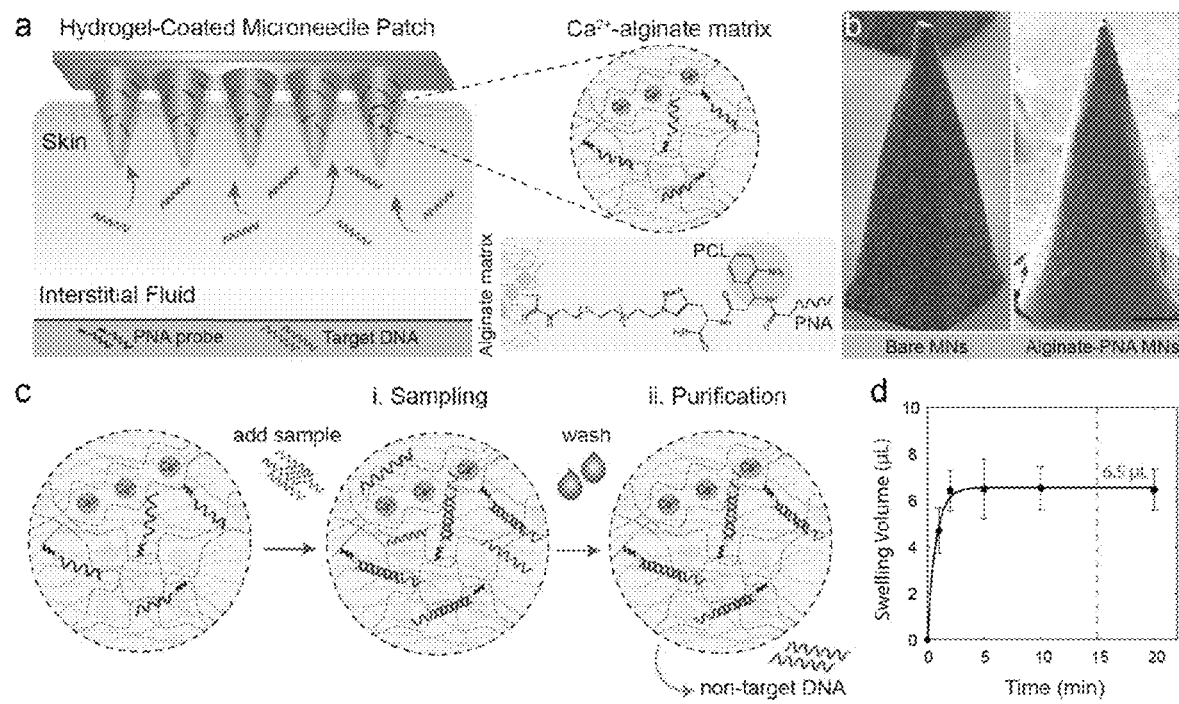
FIG. 1. Schematic representation of the hydrogel-coated microneedle platform during sampling of the interstitial fluid. (a) Microneedle arrays (MN) are functionalized with bespoke peptide nucleic acid (PNA) probes (blue) which are covalently bound to an alginate hydrogel matrix via a photo-cleavable linker (PCL, yellow). Minimally-invasive sampling of skin interstitial fluid can be achieved by pressing the coated MN patch onto the skin for 15 min. (b) Scanning electron micrograph (5.0 kV, 100× magnification, 10 nm gold sputter coating) of the bare MNs and alginate-PNA hydrogel coated MNs (scale bar=100 µm). (c) Schematic illustration of the generic protocol for MN sampling of target biomarker (red) and purification to remove non-target sequences (green). Circles represent a magnification of the alginate hydrogel coating on the MN patches. (i) When the MN is applied to sample a solution containing DNA, the target DNA sequence (red) hybridizes to the PNA probe (blue), forming a PNA:DNA complex. (ii) The MNs are washed to remove any non-specific molecules (green) which have diffused into the hydrogel matrix. (d) Swelling kinetics of the hydrogel MNs fitted by the Spring and Dashpot Voight-based model (black solid line), showing an equilibrium swelling capacity of 6.5±0.2 µL and a sampling rate constant of 0.74. Error bars show S.E.M. (N=6 MN patches).

Hydrogel-coated MN patches can sample and isolate specific miRNA biomarkers from skin ISF at the fastest rate yet, while enabling the captured miRNA to be detected in situ (FIG. 1a). The versatile platform also offers the capability of light-triggered release of the miRNA for post-sampling off-chip analysis. Poly-L-Lactide (PLLA) arrays of 77 microneedles were used as a sampling platform, as their successful use for either transdermal vaccine delivery or ISF/cell sampling from the skin has been previously reported (A. Mandal, A. V. Boopathy, L. K. W. Lam, K. D. Moynihan, M. E. Welch, N. R. Bennett, M. E. Turvey, N. Thai, J. H. Van, J. C. Love, P. T. Hammond, D. J. Irvine, Sci. Transl. Med. 2018, 10, eaar2227; P. C. DeMuth, X. Su, R. E. Samuel, P. T. Hammond, D. J. Irvine, Adv. Mater. 2010, 22, 4851-4856; P. C. DeMuth, J. J. Moon, H. Suh, P. T. Hammond, D. J. Irvine, ACS Nano 2012, 6, 8041-8051; P. C. DeMuth, A. V. Li, P. Abbink, J. Liu, H. Li, K. A. Stanley, K. M. Smith, C. L. Lavine, M. S. Seaman, J. A. Kramer, Nat. Biotechnol. 2013, 31, 1082; P. C. DeMuth, W. F. Garcia-Beltran, M. L. Ai-Ling, P. T. Hammond, D. J. Irvine, Adv. Funct. Mater. 2013, 23, 161-172; P. C. DeMuth, Y. Min, B. Huang, J. A. Kramer, A. D. Miller, D. H. Barouch, P. T. Hammond, D. J. Irvine, Nat. Mater. 2013, 12, 367; P. C. DeMuth, Y. Min, D. J. Irvine, P. T. Hammond, Adv. Healthc. Mater. 2014, 3, 47-58). Other materials suitable for the microneedle arrays disclosed herein include polymers such as polycarbonate, as well polymers coated with a layer of metal, metal alloy, or metal-containing material, such as a metal oxide. For example, polymer-based microneedles can be coated with chromium, gold, iridium oxide, or a combination thereof.

Figure 4:
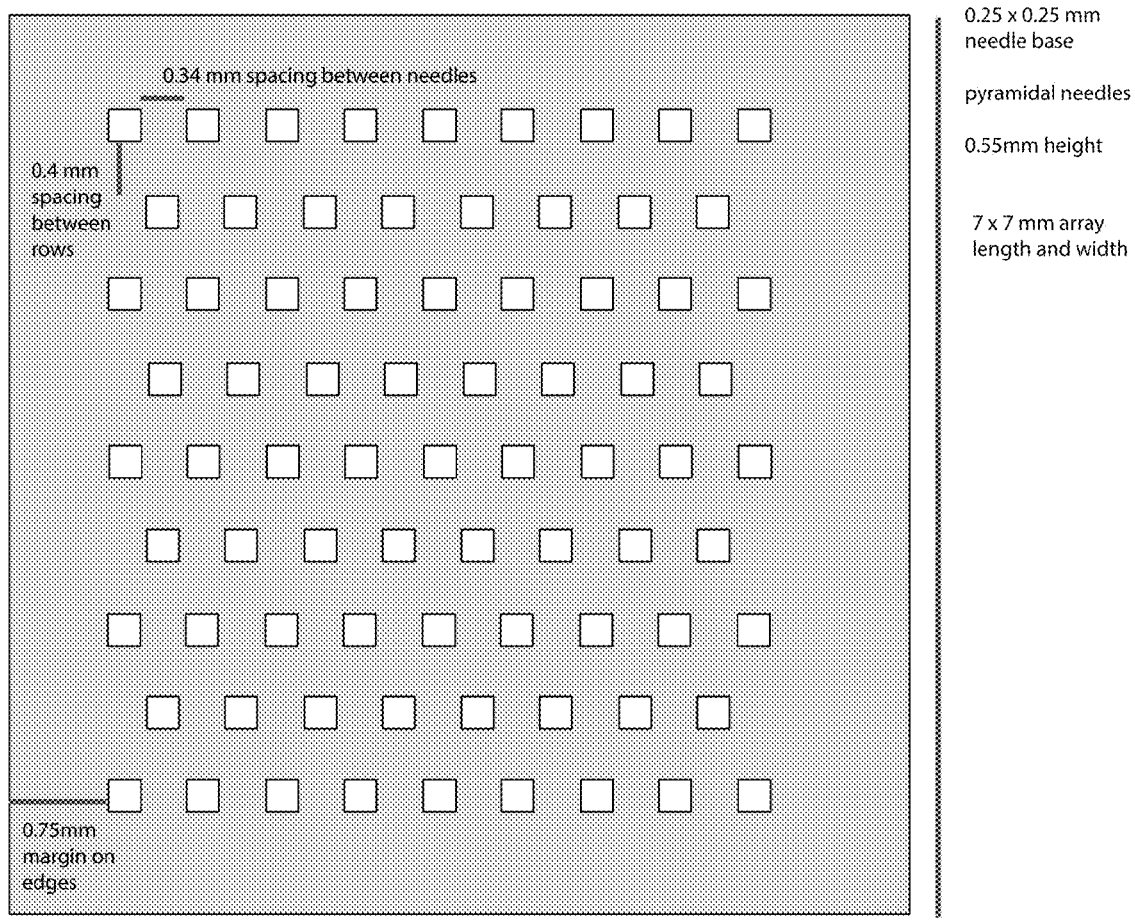
FIG. 4. Diagram showing the dimensions of the bare PLLA MN patches.
Figure 5:
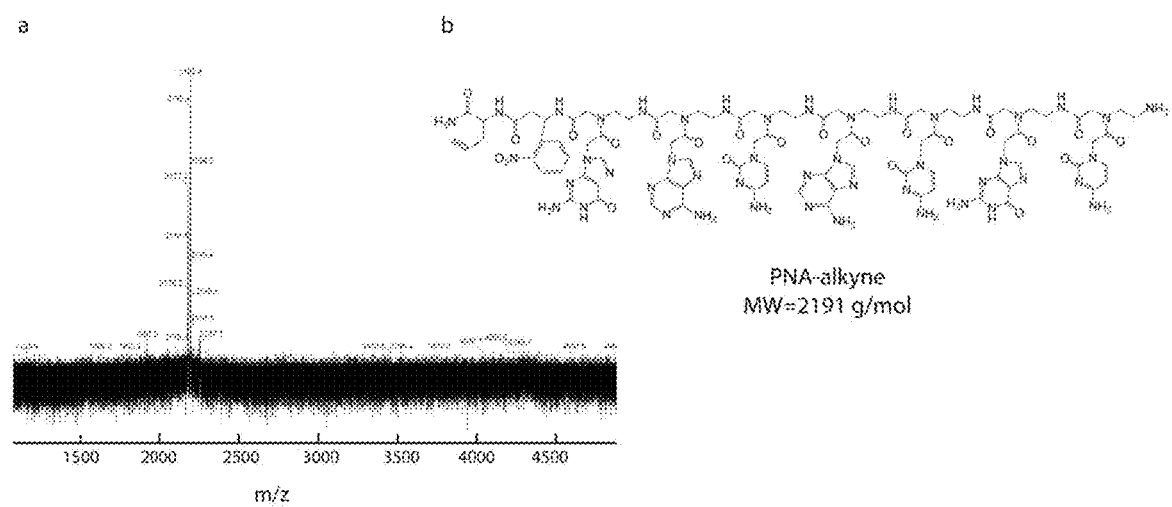
FIG. 5. (a) MALDI-TOF spectrum (matrix=sinapinic acid) and (b) chemical structure of the engineered PNA-alkyne directed against miR-210 (calculated MW 2191 g/mol).
Figure 6:
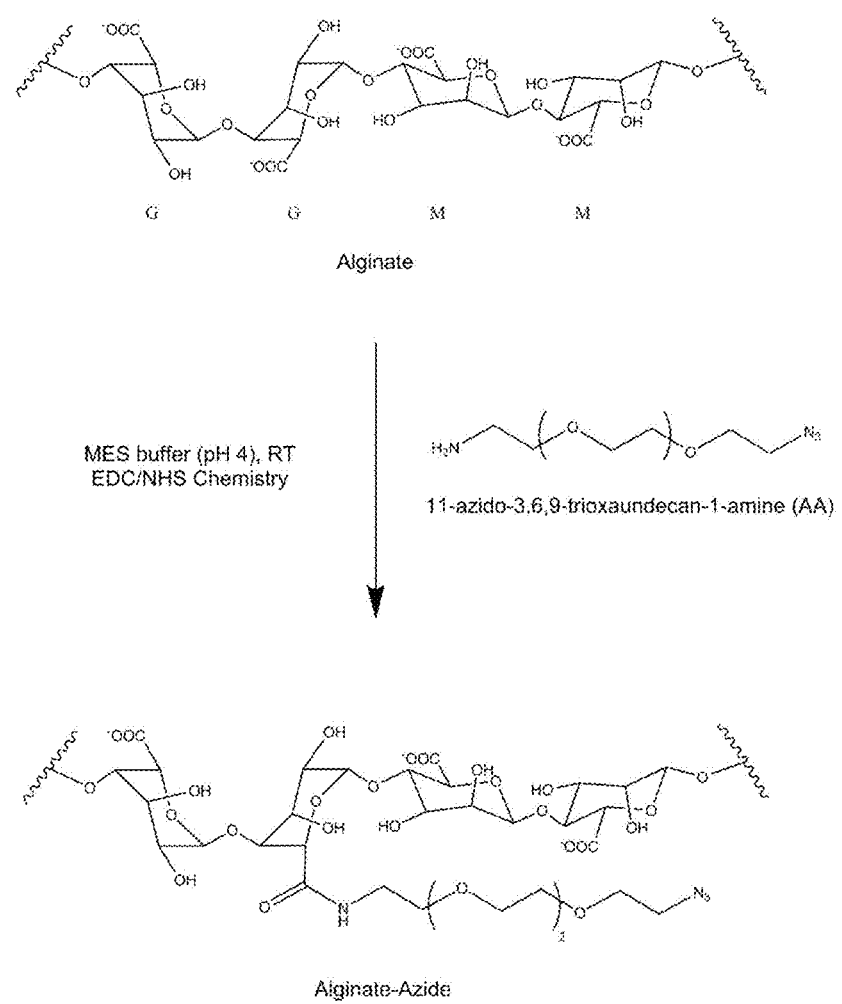
FIG. 6. Scheme depicting the synthesis of alginate-azide.
Figure 7:
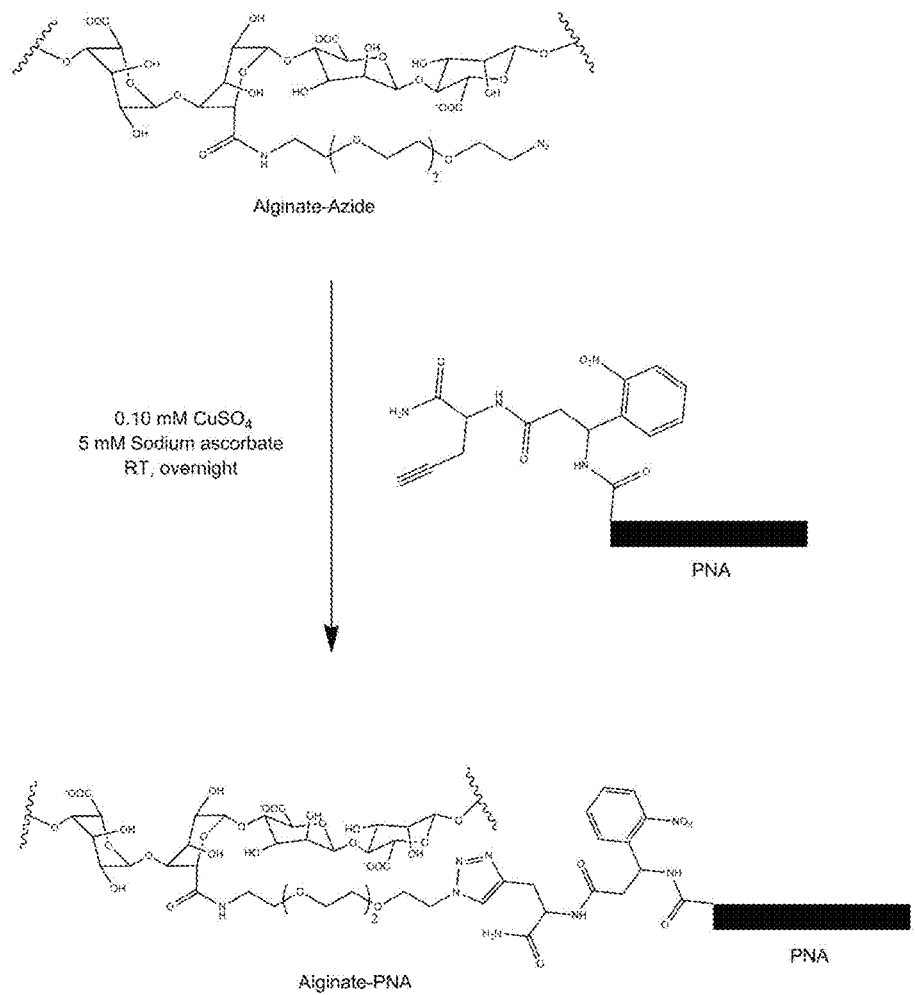
FIG. 7. Scheme depicting the synthesis of Alginate-PNA from Alginate-azide via copper-catalyzed azide-alkyne cycloaddition reaction (Click Chemistry).
Figure 8:
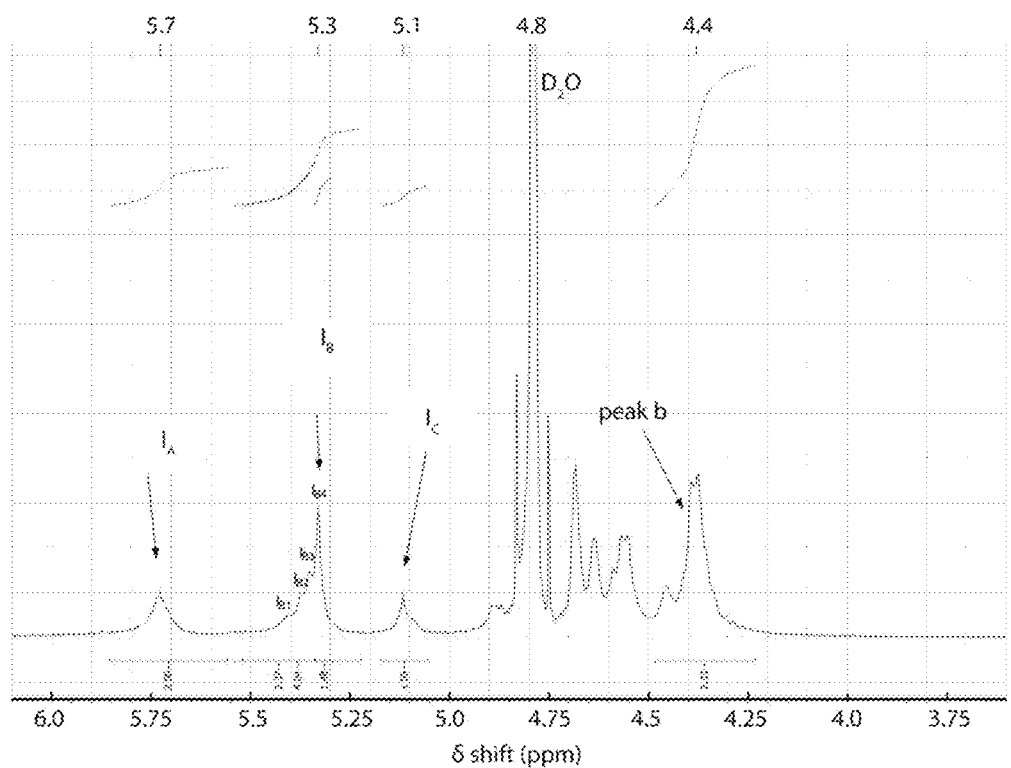
FIG. 8. $^1$H NMR spectrum of an alginate-based hydrogel, identifying peaks A, B, and C.

7×7 mm arrays were produced as previously reported, that were decorated with pyramidal-shaped MNs (FIG. 4). The height of the needles was set to 550 µm to enable them to penetrate through the epidermis layer and reach the underlying, ISF containing, dermis layer. For sampling and isolation of specific miRNA biomarkers from skin ISF, the MN array was coated with alginate polymers functionalized with Peptide Nucleic Acid (PNA) capture probes for sequence-specific immobilization of the only miRNA of interest via Watson-Crick base pairing. When compared to standard oligonucleotides, PNAs offer the advantage of a greater affinity and sequence-specificity when hybridizing to complementary DNA or RNA strands (R. Bakhtiar, *Biochem. Educ.* 1998, 26, 277-280; S. Shakeel, S. Karim, A. Ali, *J. Chem. Technol. Biotechnol.* 2006, 81, 892-899; M. Egholm, O. Buchardt, L. Christensen, G. Behrens, S. M. Freier, D. A. Driver, R. H. Berg, S. K. Kim, B. Norden, P. E. Nielsen, *Nature* 1993, 365, 566-568; V. V. Demidov, V. N. Potaman, M. D. Frank-Kamenetskil, M. Egholm, O. Buchard, S. H. Sonnichsen, P. E. Nielsen, *Biochem. Pharmacol.* 1994, 48, 1310-1313; P. E. Nielsen, M. Egholm, *Curr. Issues Mol. Biol.* 1999, 1). Accessible through easily scalable solid-phase peptide synthesis, PNAs have proven highly valuable analytical tools for nucleic acid sensing, both in vitro and in vivo, and are particularly well suited for the detection of short oligonucleotides such as miRNAs. Herein, a 7-mer PNA was designed that was complementary to the 5'-end of miR -210, a recently identified biomarker for early systemic melanoma recurrence (FIG. 5). Melanoma patients with abnormally elevated levels of circulating miR-210 were indeed found to be more likely to have disease recurrence, reinforcing the need for a non-invasive test suitable for longitudinal monitoring (S. Ono, T. Oyama, S. Lam, K. Chong, L. J. Foshag, D. S. B. Hoon, *Oncotarget* 2015, 6, 7053-7064; S. K. Huang, D. S. B. Hoon, *Mol. Oncol.* 2016, 10, 450-463). DNA version of miR-210 (DNA-210) was chosen as the target of interest. The PNA was functionalized at its C-terminus with an alkyne moiety to facilitate its covalent immobilization to an azide-modified alginate via copper-catalyzed cycloaddition reaction (Click chemistry). A photo-cleavable linker (3-Amino-3-(2-nitrophenyl) propanoic acid) (PCL) was also introduced between the alkyne and the PNA sequence to enable the release of the PNA:DNA hybridization complex post ISF sampling via photo-activation with near-UV light (300-360 nm) (FIG. 1a). The alginate-azide polymer was prepared as previously reported by EDC/NHS mediated peptide coupling between low viscosity alginate and 11-azido-3,6,9-trioxyundecan-1-amine, leading to an average level of azide functionalization of 17 mol % (FIG. 6) (S. I. Presolski, V. P. Hong, M. G. Finn, *Curr. Protoc. Chem. Biol.* 2011, 3, 153-162). The alginate-PNA hybrid material was finally assembled by azide-alkyne cycloaddition reaction, in the presence of Cu(II) sulphate, Tris[(1-benzyl-1H-1,2,3-triazol-4-yl)methyl]amine (TBTA) and sodium ascorbate, leading to an overall level of PNA functionalization of 1 mol % as assessed by $^{1}$H-NMR spectroscopy (FIGS. 7 and 8).

Figure 10:
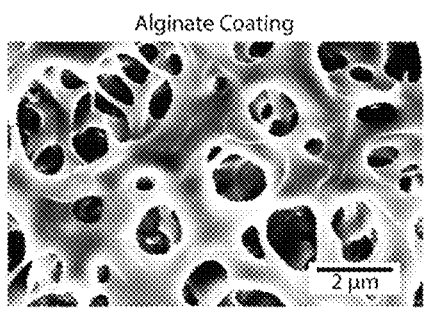
FIG. 10. SEM micrographs (5.00 kV, 10 nm chromium coating, ZEISS Sigma 300) of calcium-crosslinked alginate coating (a) compared to a calcium crosslinked alginate-PNA coating (b) at 100K magnification (top) and 25K magnification (bottom).
Figure 10:
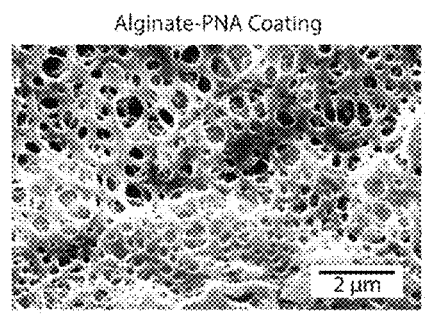
Figure 10:
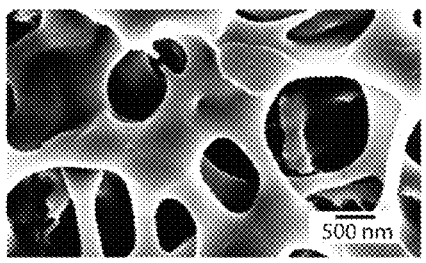
Figure 10:
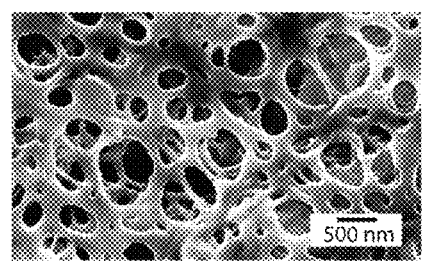
Figure 11:
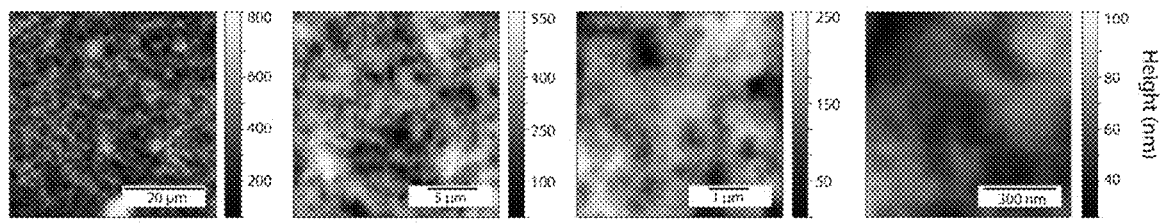
FIG. 11. Atomic force microscopy images of Alginate-PNA coating (AFM, Asylum MFP-3D) conducted at room temperature in standard (AC) tapping mode with PPP-NCHR probes (NANOSENSORS™, Windsor Scientific), showing magnifications of the same sample.

Coating of the MN arrays with the newly engineered alginate-PNA proceeded in three steps: pre-coating with poly-L-Lysine followed by deposition of the alginate and finally physical crosslinking with calcium chloride ($CaCl_2$)), leaving enough time for the MN to dry between each step. Once fully dried, scanning electron microscopy (SEM) was used to characterize and compare the physical morphology at the surface of the MN patches with and without alginate-PNA hydrogel coating (FIG. 1b) To determine the effect of PNA functionalization on the alginate's physical properties, MN patches coated with unmodified alginate were also analyzed. The SEM micrographs of both types of alginate displayed an interconnected network of pores with a relatively consistent pore size. Although SEM only provides information on the hydrogels' structures in their non-swollen dehydrated form, it is noteworthy that the average pore size of the dehydrated alginate-PNA coating was approximately half that of the unmodified alginate (FIG. 10). This could be due to the hydrophobic nature of the charge-free PNAs limiting water uptake and reducing swelling, as previously observed when functionalizing hydrogel fibers with hydrophobic moieties (D. Al Sulaiman, P. Cadinu, A. P. Ivanov, J. B. Edel, S. Ladame, *Nano Lett.* 2018, 18, 6084-6093). Atomic Force Microscopy (AFM) was also used to gain an insight into the topography of the alginate-PNA on surface. For ease of imaging however, the hydrogel was deposited on a glass slide, but this time no lyophilization or metal coating was needed, therefore providing a more accurate representation of the hydrogel structure. The surface topography showed a relatively consistent and homogeneously distributed porous structure over the 50×50 $\mu m^2$ area with pores or voids of 200-800 nm (FIG. 11), only slightly larger than those observed, after lyophilization, by SEM. As earlier studies showed, small oligonucleotides the size of miRNAs could easily diffuse within such porous materials and hybridize to pre-embedded PNAs (D. Al Sulaiman, J. Y. H. Chang, S. Ladame, *Angew. Chem. Int. Ed.* 2017, 56, 5247-5251).

The main limitations of existing ISF sampling platforms are their low sampling capacity and low sampling rates. For example, micro-dialysis techniques typically sample at 1-5 µL/min while less invasive capillary ultrafiltration is even slower, at 100-150 nL/min. The swelling behavior of the hydrogel-coated MNs was assessed in buffer (PBS) and at physiological body temperature (37° C.). FIG. 1d describes the volume of liquid absorbed by the MN over time which can be fitted by the Spring and Dashpot Voight-based model commonly used for describing swelling kinetics of hydrogels. According to this model, the hydrogel-coated MNs have an equilibrium swelling capacity of 6.5±0.2 µL, with a sampling rate constant of 0.74, meaning that 63% of the full swelling capacity is achieved in less than 1 min. This compares very favorably with other recently reported hydrogel-coated MN sampling technologies and can at least in part be attributed to the large surface area of the MNs due their pyramidal shape and porous coating structure.

Figure 2:
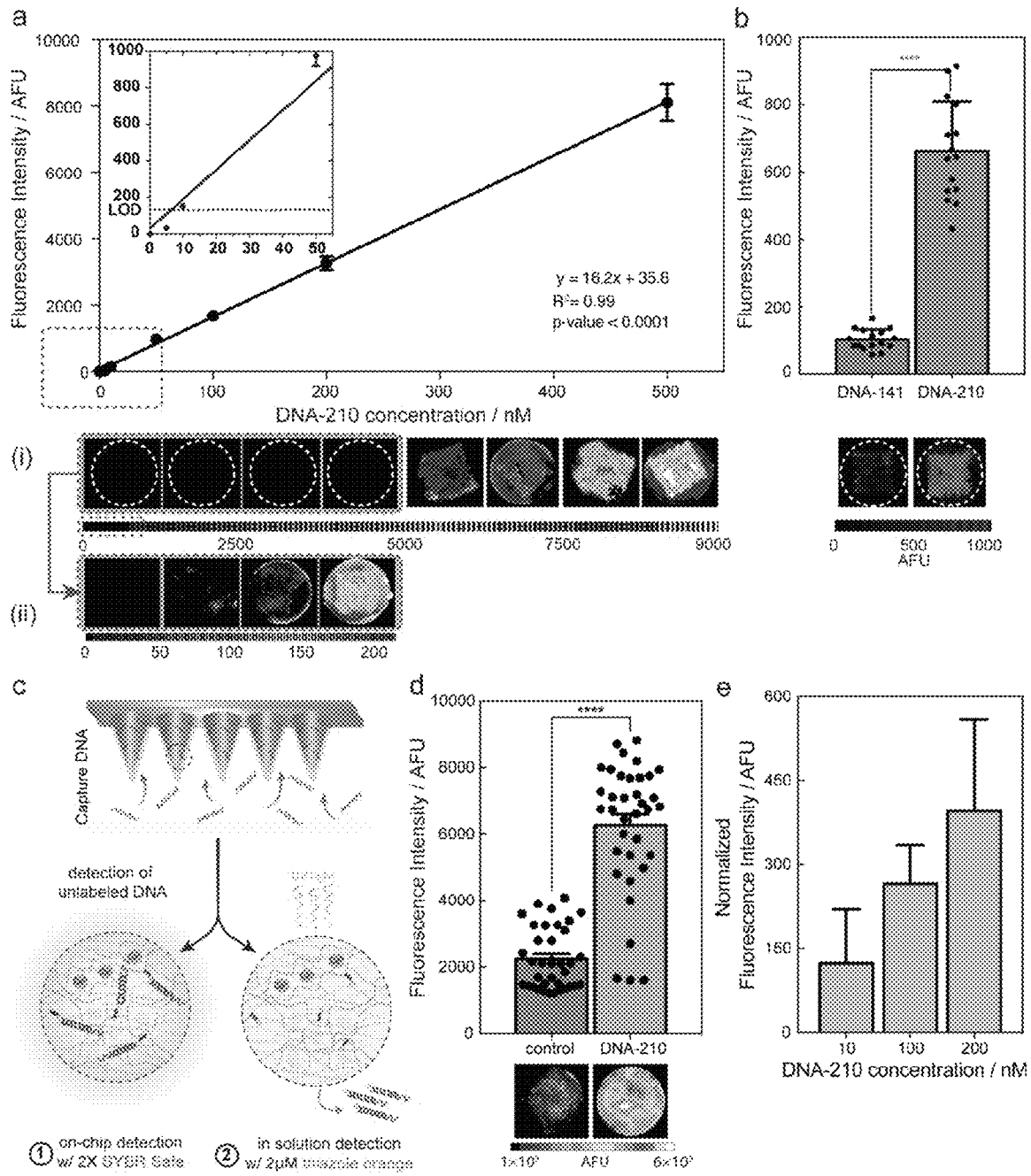
FIG. 2. Validation of the MN sampling and release mechanism. (a) Calibration curve showing the mean fluorescence intensity of N=22 needles from two MN patches (error bars show S.E.M.), with a linear regression fitting and associated equation with fitting $R^2$ and p-value. Fluorescence scanner images of representative MN patches after sampling fluorescently-labelled target DNA-210 at given concentrations (0-500 nM). Two color scale/calibration bars were used to facilitate visualization of the large dynamic range of fluorescence values (a (i) and a (ii), respectively). Inset shows magnification of the boxed area in (a) with the y-intercept (y-int) of the calibration curve and the limit of detection (LOD), calculated as three times the standard deviation of the y-int, equivalent to 6 nM. (b) Specificity of MN Platform. Comparison of the mean fluorescence of N=16 needles from 2 MN patches after sampling 500 nM of non-complementary DNA-141 (left, grey) and complementary DNA-210 (right, red), with fluorescence scans of representative MN patches shown below. (c) Schematic representation illustrating the two mechanisms for detecting captured unlabeled DNA, either (1) on-chip by dipping the MN into intercalator dye to visualize the PNA:DNA complex directly on the MN patch, or (2) by releasing the PNA:DNA complex into solution (UV irradiation) then adding an intercalator dye to the solution. On-chip detection results are plotted in (d) showing a significant difference in fluorescence between MN sampling DNA-210 (500 nM) or control (no DNA target in 100 mM phosphate buffer, pH 7.4) (unpaired two-tailed t-test, p<0.0001). UV-cleaved PNA: DNA complex detection in solution results are plotted in (e) showing an increase in fluorescence of the release solution after sampling target DNA-210 at 10, 100, or 200 nM. Note that data is normalized by subtracting the background fluorescence of the dye (2 µM, control i.e. no DNA).

To test the ability of the MN patches to sample and isolate nucleic acids in a sequence specific manner, MNs were dipped into solutions (100 µL) containing various amounts of DNA -210 (0-500 nM) labelled with Alexa 647 dye. After 15 min sampling, the MNs were washed thoroughly with water and dried overnight at room temperature before imaging with a fluorescence scanner (Typhoon FLA9500, GE Healthcare). As shown in FIG. 2a, a plot of the mean fluorescence intensity (N=22 individual microneedles from 2 different MN patches) versus DNA concentration demonstrates the ability of the patches to detect target concentrations as low as ~6 nM, with a linear regime across almost 2 orders of magnitude (6-500 nM). Sequence specificity was then confirmed by demonstrating the statistically significant ability of the MN patch to discriminate between a complementary and a non-complementary DNA target, both labelled with the same fluorophore (FIG. 2b).

Figure 12:
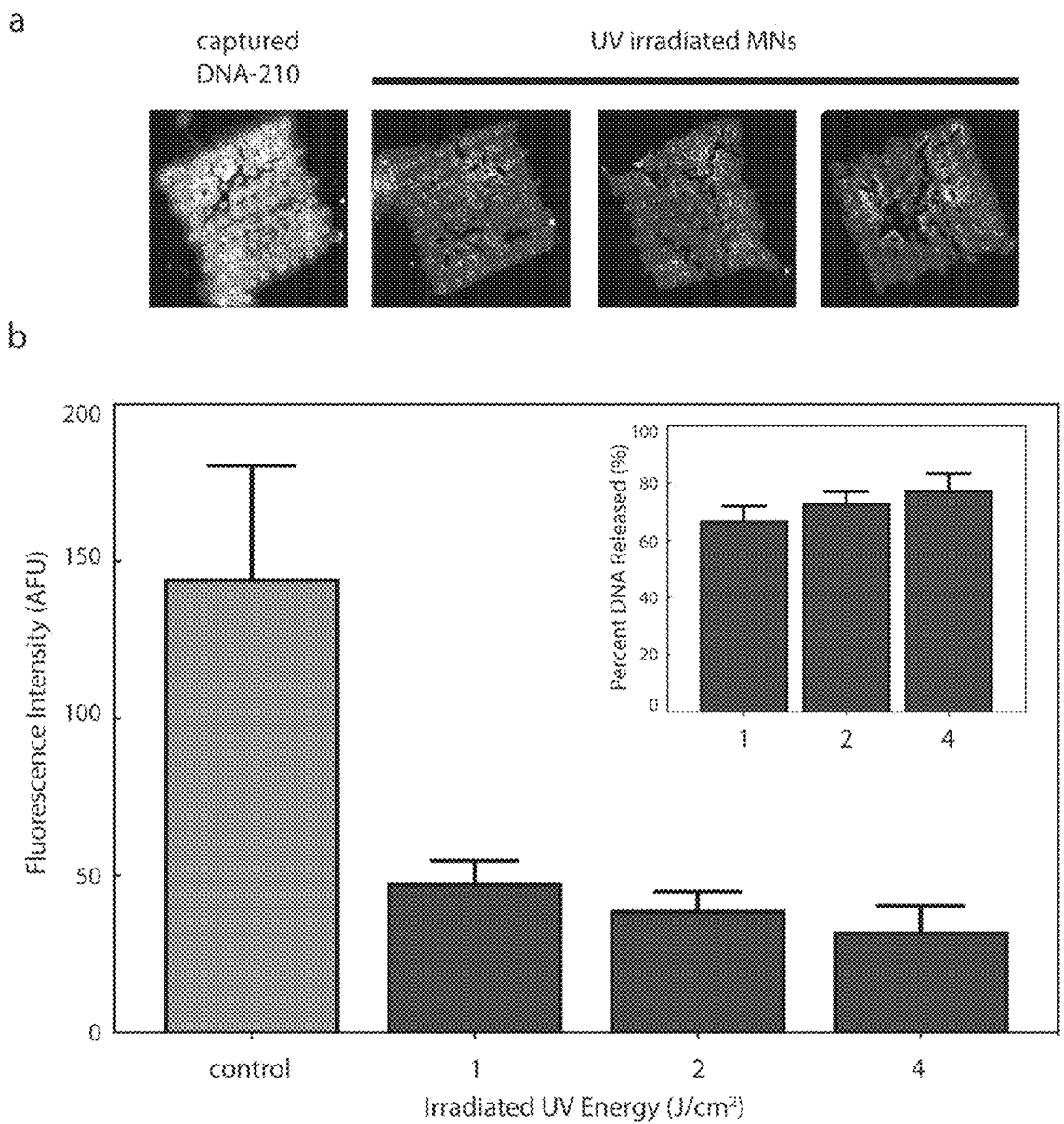
FIG. 12. Validation of MN release mechanism. Fluorescence scans (a) and mean fluorescence (b) of individual MNs after sampling DNA (control, no UV irradiation) and after UV irradiation and release of DNA by 1, 2 or 4 J/cm$^2$ of UV energy. Error bars show S.E.M (N=16 MNs). Inset shows the percentage of DNA released into solution after UV irradiation with different amounts of energy.

In order to demonstrate the possibility to release the captured nucleic acid from the microneedle, MN patches pre-incubated with fluorescently-labelled DNA-210 were placed tips-down in water (100 µL) within a UV crosslinker (UVP) and irradiated with increasing amounts of UV energy ($\lambda_{ex}$=315 nm, 0-4 J/cm$^2$). After shaking for 1 h, the MNs were rinsed, dried and imaged on a fluorescence scanner. A significant loss in fluorescence intensity of the MN was observed post-irradiation that suggested the release of over 70% of the captured DNA after 1 min of irradiation (FIG. 12).

The MN patches were not only designed to sample specific endogenous nucleic acid biomarkers from skin ISF, but also to enable their quantitative detection once sampled. Two different mechanisms for sensing were explored that involved either (i) the direct visualization of the isolated biomarker whilst captured on the microneedle patch or (ii) an alternative two-step process involving light-triggered release of the PNA:DNA complex followed by detection in solution (FIG. 2c). For both sensing strategies, the MN patches were initially dipped into solutions (100 μL) containing various amounts of unlabeled DNA-210 (10-200 nM), then washed thoroughly to remove any unbound DNA and dried. For direct visualization, the MN patches were then incubated in a solution of DNA intercalator (SYBR Safe, 2× concentration, Invitrogen), washed and imaged with a fluorescence scanner (FIG. 2d). For indirect visualization, the DNA-loaded MN were then placed tips-down into 100 μL of water and irradiated for 3 min at 3 J/cm$^2$ in a photo-crosslinker (BLX-315, $\lambda_{ex}$=315 nm). A solution of DNA intercalator was then added to detect the PNA:DNA complex released in solution (FIG. 2e). Both strategies proved successful at detecting nM concentrations of nucleic acids sampled with the MN patches, highlighting the versatility of this platform. Whilst simpler and more direct on-chip detection is perfectly suited for applications that require testing at the point-of-care, the possibility of releasing the captured and purified (i.e. separated from all other ISF constituents, including other nucleic acid) material offer the possibility to detect and sequence less abundant biomarkers (through amplification-based methodologies).

Figure 3:
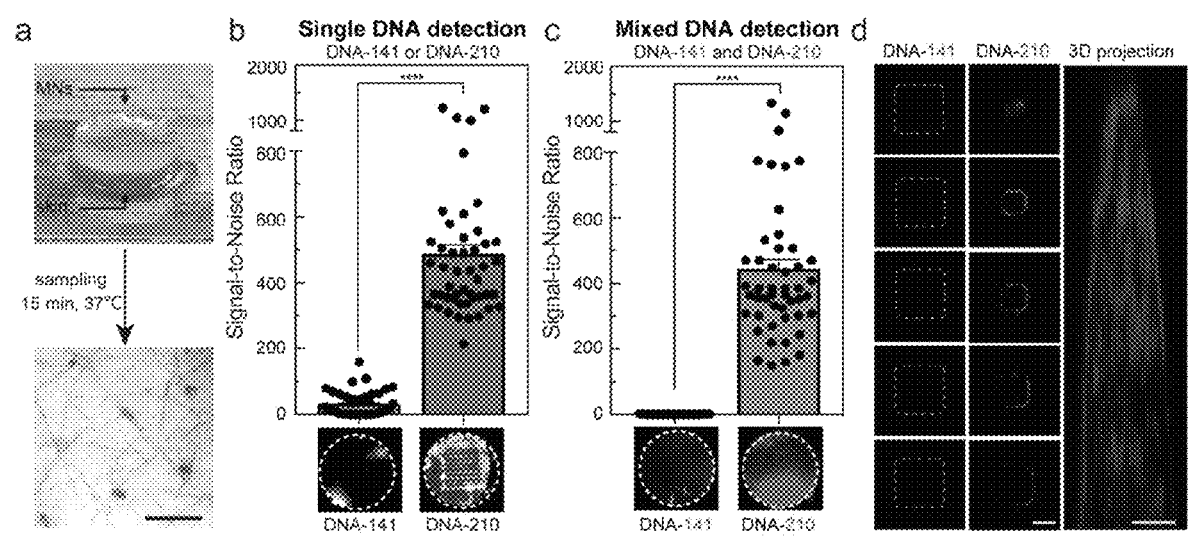
FIG. 3. MN Validation with human skin sample. (a) Experimental protocol for applying MNs to human skin biopsies. (Top) MNs were applied to 8 mm$^2$ human skin biopsies for 15 min at 37° C. to sample target and non-complementary DNA. (Bottom) Optical micrograph of human skin showing MNs penetration pattern stained with trypan blue (scale bar=300 µm). SNR is represented as the ratio between average fluorescence intensity of MNs after sampling skin with DNA and without DNA (i.e. control) (N=48 from three MN patches). (b) Bars depict the SNRs after sampling skin incubated with only non-complementary DNA-141 (left, grey) or only complementary DNA-210 (right, blue), both tagged with Alexa-647 dye. (c) Bars depict the SNRs after sampling skin incubated with a mixture of complementary DNA-210 with a Cy5 dye and non-complementary DNA-210 with a Cy2 dye, imaged under Cy2 filter (left, grey) and Cy5 filter (right, red). In (b) and (c) Statistical analysis shows a significant difference between sampling target and non-complementary DNA (unpaired two-tailed t-test, p-value <0.0001). Representative MN fluorescence scans are displayed below. (d) Representative fluorescent confocal images from the captured DNA bound to the MN are shown in these images. (Left) Non-complementary DNA-141 imaged with $488_{ex}/510_{em}$ shows little to no fluorescence signal on the MNs. (Middle) Complementary DNA-210 imaged with $647_{ex}/665_{em}$ shows fluorescence signal bound to the MN. (Right) 3D projection of the fluorescence signal from a single microneedle. (Scale bar=200 µm).

Having validated the sensitivity and selectivity of the MN sampling in vitro, the sampling of specific nucleic acids from skin ISF directly in human skin, using an ex-vivo model, was investigated. Human abdominal skin samples were first prepared by incubation with either a complementary (DNA-210) or a non-complementary (DNA-141) oligonucleotide labelled with Alexa-647 dye (500 nM each) and then washed thoroughly with water. MN patches were then pressed onto the skin surface (15 min, 37° C.) for sampling and then washed extensively and dried overnight before fluorescence imaging (FIG. 3a). Images were analyzed by taking the average fluorescence of individual microneedles on each patch (N=48 microneedles from three different MN patches). These results not only demonstrate that the MNs can indeed sample nucleic acids from skin ISF but also that they retain their high sequence specificity, capturing preferentially (15-fold) the DNA fragment complementary to the PNA incorporated into the hydrogel (FIG. 3b). To confirm these findings a second experiment was prepared where the skin samples were incubated in a solution containing a mixture of both DNA-210 (red bars) and DNA-141 (green bars) labelled with Alexa-647 and 6-FAM, respectively. After sampling (as described above), MN patches (N=3 per condition) were imaged successively under two excitation filters (FIG. 3c). Whilst no significant difference between the experiments with and without DNA was detectable with the Cy2 filter (for 6-FAM visualization), a very strong signal increase was observed between the DNA-free control and the experiment with DNA, confirming the efficient and sequence-specific capturing of DNA-210 spiked within human skin ISF. Fluorescent confocal imaging of the MNs was also performed to confirm the previous findings and visualize the DNA captured around each MN (FIG. 3d). Non-complementary DNA-141 imaged with 488ex/510em showed little to no fluorescence signal on the MNs (FIG. 3d, left), while complementary DNA-210 imaged with 647ex/665em showed fluorescence signal bound to the MN (FIG. 3d, middle). A 3D projection of the fluorescence signal from a single microneedle is also shown (FIG. 3d, right).

Figure 13:
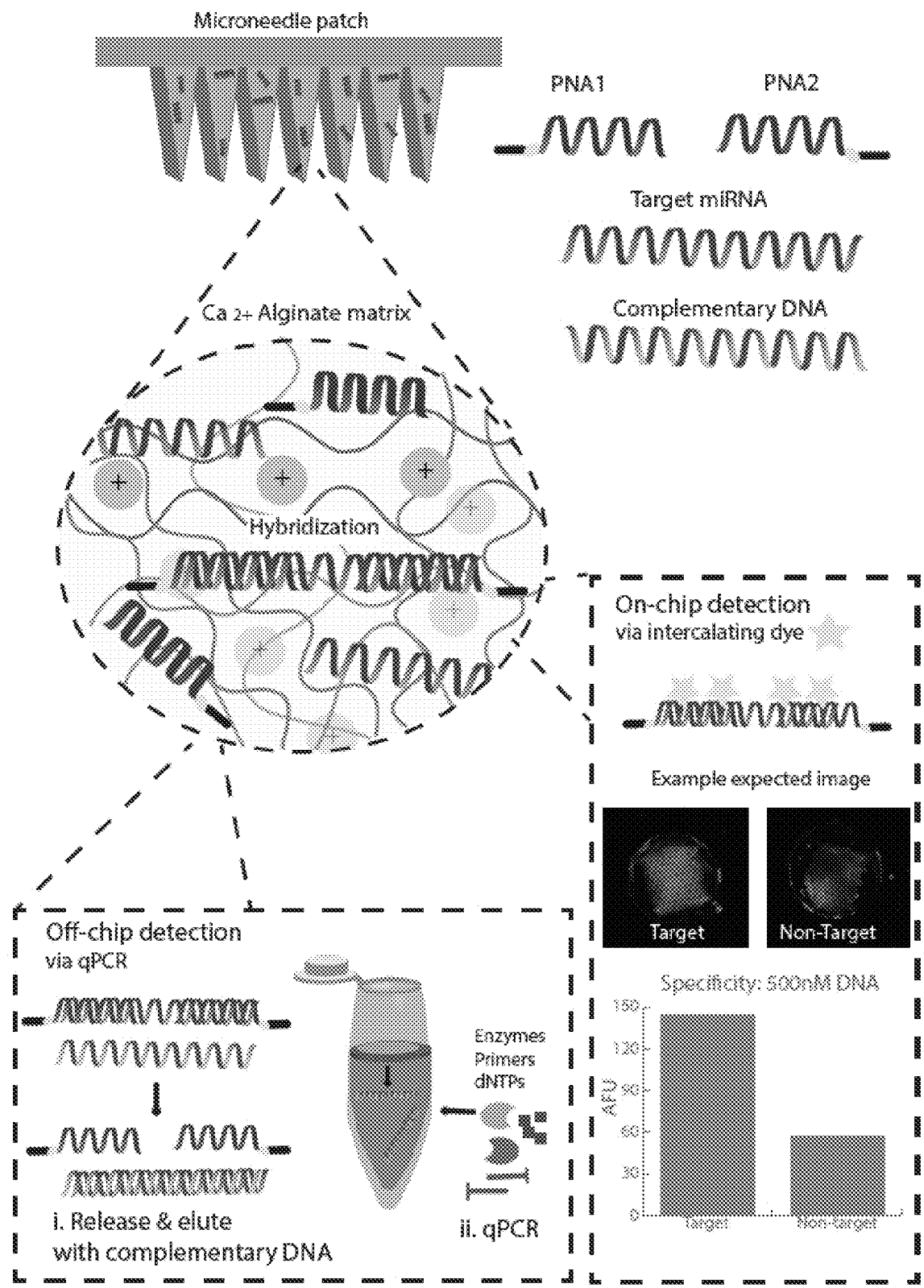
FIG. 13. Microneedle patch containing two PNAs complementary to the 5' and 3' ends of the same target miRNA for on-chip and off-chip detection.

The disclosed technology can be modified to introduce 2 or more different PNA oligomers into the hydrogel. For example, FIG. 13 shows a schematic representation of an MN patch coated with engineered hydrogels functionalized with 2 short PNA oligomers (5-8 bases long) that are complementary to the 5' and 3' ends of the same target miRNA. In this case capturing of the miRNA of interest proceeded via sequence-specific hybridization to both short PNA probes whilst all miRNAs not fully complementary to both probes were washed away. Subsequent MRNA detection can be carried out on-chip or off-chip. On-chip detection was performed via addition of a fluorogenic DNA intercalator (e.g. SYBR-green, SYBR-safe, or Thiazole orange) to detect the amount of PNA:DNA heteroduplex present in the hydrogel. Off-chip detection was performed via addition of a (natural or functionalized) DNA oligonucleotide fully complementary to the miRNA of interest. The DNA:RNA heteroduplex can then be eluted of the hydrogel and detected in solution. Functionalization of the DNA oligonucleotide will include biotin and thiol or any other chemical functionality that will enable capturing of the released miRNA:DNA duplex onto particles or lateral flow assay.

Using 2 short PNA oligomers enables optimal sequence specificity for unique miRNA sequences. Only miRNA that are complementary to both PNA oligomers with remain bound to the MN through sequence specific hybridization whilst partially bound miRNAs (e.g. miRNAs complementary to only one of the PNA oligomers) will be eluted off through stringent washes prior to detection.

Figure 14:
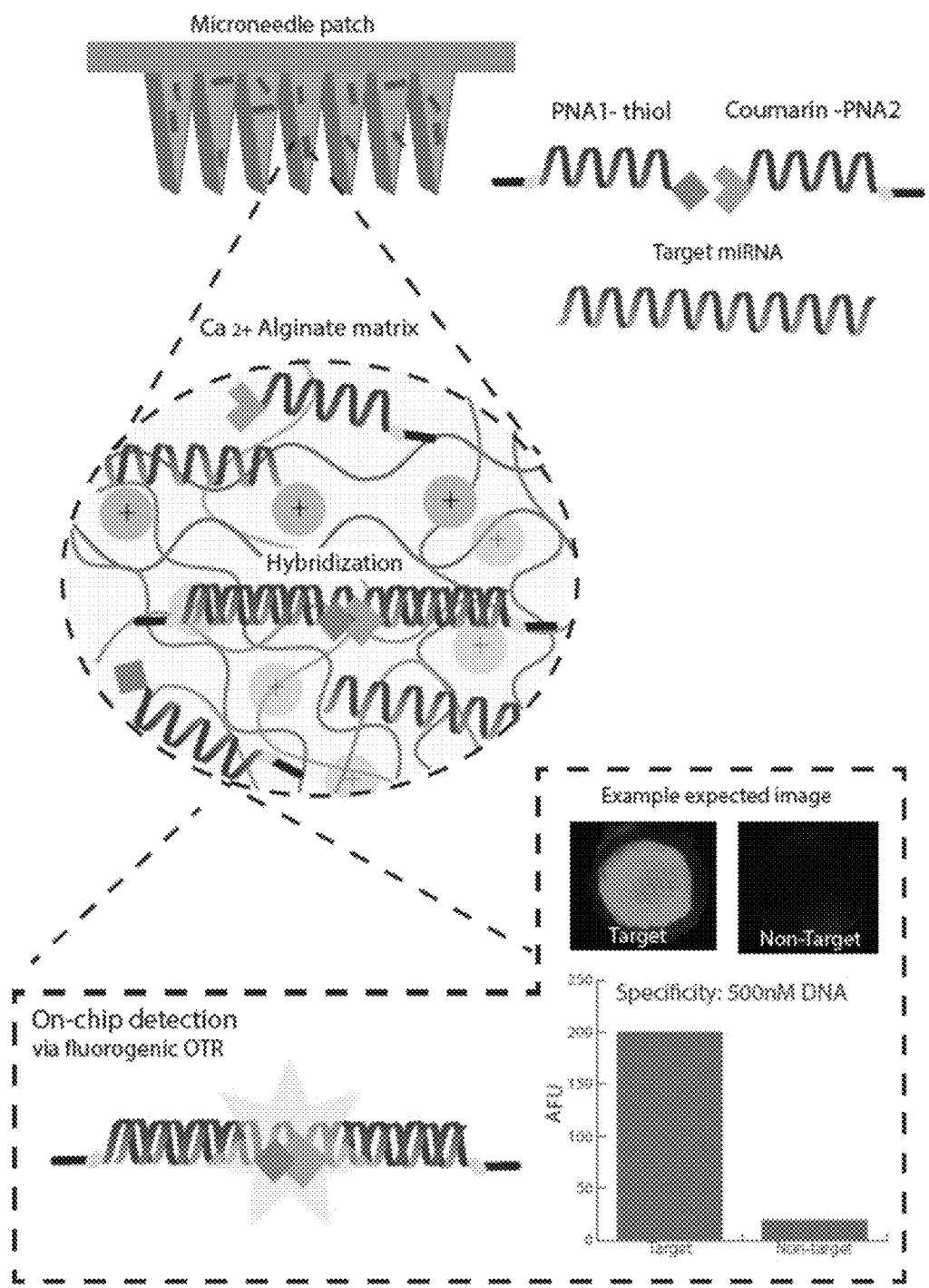
FIG. 14. Microneedle patch containing two short PNA oligomers (5-8 bases long) that are functionalized with chemical probe heads for on-chip detection. Probes are designed to be complementary to two different part of the same miRNA, bringing both probe heads in close proximity to each other in order for both PNAs to hybridize simultaneously to the same miRNA.

Alternatively, MN patches can be coated with engineered hydrogels functionalized with 2 or more short PNA oligomers (5-8 bases long) that are functionalized with chemical probe heads (FIG. 14). Probes are designed so that they are complementary to two different part of the same miRNA, bringing both probe heads in close proximity to each other with both PNA hybridize simultaneously to the same miRNA. Capturing of the miRNA of interest proceeds via sequence-specific hybridization to both short PNA probes whilst all miRNAs not fully complementary to both probes are washed away. miRNA detection is carried out on-chip using either an optical or electrochemical readout as a result of an on-chip oligonucleotide-templated reaction (OTR). Both probe heads are kept far away from each other unless they are both hybridized to the same template miRNA, therefore accounting for an extremely low background fluorescence. Example of probe head pairs can include, for example, a thiol derivative and a quenched coumarin; or an aniline derivative and a quinone.

Probe heads can be designed so that they can react with each other upon simultaneous binding to the same miRNA target to form an electrochemically active product with characteristic redox properties, significantly distinct from those of the unreacted probes (see example below), thus producing an electrochemical signal. The electrochemical signal generated upon formation of the product can be measured using electrochemistry techniques such as cyclic voltammetry (CV), differential pulse voltammetry (DPV), square wave voltammetry (SWV) electrochemical impedance spectroscopy (EIS) or amperometry.

A characteristic readout (optical or electrochemical) is provided by stimulus-responsive probe-heads already incorporated into the hydrogel structure through covalent attachment at the end of the PNA oligomers. This offers the advantage of a direct, real-time and on-chip monitoring of the miRNA biomarkers as they diffuse into the MN patch, without the need for further processing or use of additional chemicals. Most useful optical probe heads will (i) have a fluorescence quantum yield close to zero and react with each other to form a product with a high fluorescence quantum yield (i.e. fluorogenic probes) or (ii) will form a product that is characterized with excitation and/or emission wavelengths significantly different from those of the two probe heads (i.e. ratiometric probes). They will also ideally have emission and excitation wavelengths >450 nm to avoid interference from any background fluorescence. Most useful electrochemical probe heads will possess redox properties that are significantly different from those of the product (or adduct) formed upon reaction of the probe heads with each other.

Figure 15:
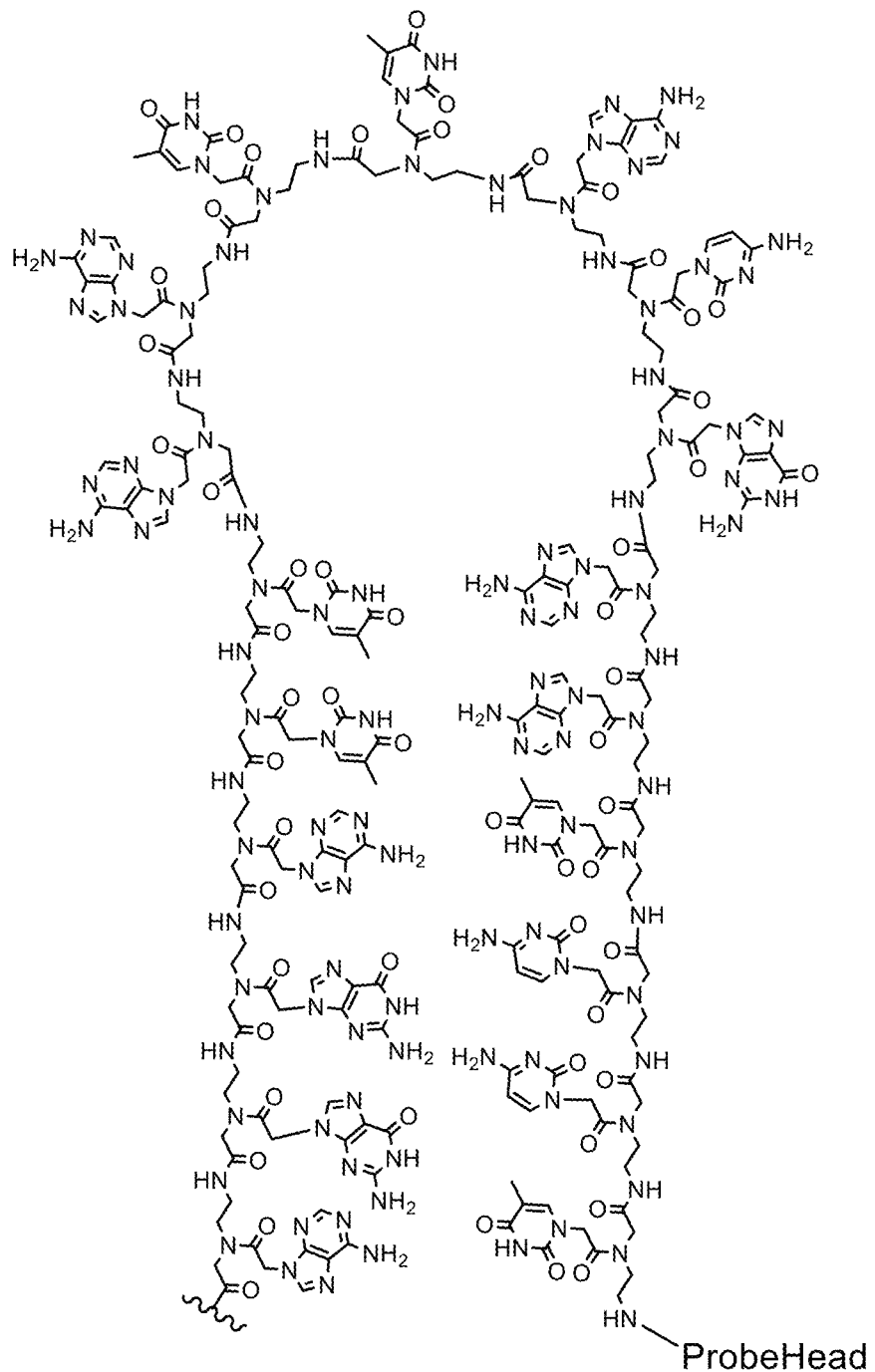
FIG. 15. Structure of a hairpin PNA comprising a probe head.

Alternatively, MN patches can be coated with at least one folded PNA oligomer, such as hairpin PNA (as described, for example, in Armitage, B., Koch, T., Frydenlund, H., Orum, H., Schuster, G. B., *Biochemistry* 1998, 37(26), 9417-9425), that is functionalized with a chemical probe head. Hairpin PNAs are single-stranded PNA oligomers having self-complementary sequences that form stem-loop-containing structures. An Example of a hairpin PNA comprising a probe head is shown in FIG. 15.

The PNA is designed to be complementary to the target miRNA. Capturing of the miRNA of interest proceeds via unfolding and sequence-specific hybridization to the PNA probe resulting in a characteristic change in the optical or electrochemical properties of the probe head The change in the probe head environment is caused by the conformational change of the PNA, and results in generation of a detectable signal.

In summary, a new generation of MN patches coated with hybrid alginate-PNA hydrogels that can sample up to 6.5 μL of fluid in 2 minutes was developed. Unlike other sampling technologies reported to date, it was demonstrated that attaching PNA oligomers to the hydrogel's fibers also enables the specific sampling, purification and release of the only nucleic acid fragments that are complementary to the PNA sequence. This versatile platform can therefore by easily tuned by simply adapting the PNA sequence to that of any miRNA of interest. Functionalization of the hydrogel with different PNA sequences complementary to different miRNAs will also enable the sampling and sensing of multiple miRNAs simultaneously (known as multiplexed analysis or profiling). Optical sensing of the captured biomarkers is also possible, either directly on-chip or in-solution after an additional light-triggered release step. Using a human skin ex-vivo model, it was demonstrated that this technology could efficiently capture nucleic acids spiked within skin interstitial fluids with both high efficiency and sequence specificity. With the recent experimental evidence that skin ISF contains the same RNA species (including circulating miRNAs) as blood with comparable natural abundance, minimally-invasive technologies that can not only sample this body fluid but can also interrogate its composition have the potential to transform the field of molecular diagnostics from liquid biopsies.

Definitions

As used herein, "eluting" refers to the process of removing analytes from the adsorbent by running a suitable solvent or solution, called an "eluent", past the adsorbent/analyte complex.

As used herein, "probe head", also known as "terminating head group", refers to a chemical moiety covalently bound to the N-terminus or C-terminus of the PNA.

The term "selective binding", as used herein, refers to two molecules forming a complex having the dissociation constant ($k_d$) of less than or equal to $10^{-6}$ M (e.g., $10^{-7}$, $10^{-8}$, $10^{-9}$, or $10^{-10}$ M).

The term "alkyl," as used herein, means a saturated straight-chain, branched or cyclic hydrocarbon. When straight-chained or branched, an alkyl group is typically $C_{1-8}$, more typically $C_{1-6}$; when cyclic, an alkyl group is typically $C_{3-12}$, more typically $C_{3-7}$. As such, "$C_{1-6}$ alkyl" means a straight or branched saturated monovalent hydrocarbon radical having from one to six carbon atoms (e.g., 1, 2, 3, 4, 5 or 6). The terms "alkyl", "alkoxy", "hydroxyalkyl", "haloalkyl", "aralkyl", "alkoxyalkyl", "alkylamine", "dialkyamine", "alkylamino", "dialkyamino", "alkoxycarbonyl", "carbocyclylalkyl", "heterocyclylalkyl" and the like, used alone or as part of a larger moiety includes both straight and branched saturated chains containing one to eight carbon atoms. The term "cycloalkyl" used alone or as part of a larger moiety, shall include cyclic $C_{3-12}$ hydrocarbons which are completely saturated. Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like.

The term "aryl," alone or in combination, as used herein, means an aromatic hydrocarbon radical of 6-18 carbon atoms (i.e., $C_{6-18}$ aryl) derived by the removal of hydrogen atom from a carbon atom of a parent aromatic ring system. In some instances, an aryl group has 6-12 carbon atoms (i.e., $C_{6-12}$ aryl), preferably 6-10 carbon atoms (i.e., $C_{6-10}$ aryl). Some aryl groups are represented in the exemplary structures as "Ar." Aryl includes bicyclic radicals comprising an aromatic ring fused to a saturated, partially unsaturated ring, or aromatic carbocyclic or heterocyclic ring. In particular embodiments, aryl is one, two or three rings. Typical aryl groups include, but are not limited to, radicals derived from benzene (phenyl), substituted benzenes, naphthalene (naphthyl), anthracene (anthryl) etc. Other aryl groups include, indanyl, biphenyl, phenanthryl, acenaphthyl and the like. Preferably, aryl is phenyl group.

The term "halo" or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The term "haloalkyl", as used herein, includes an alkyl substituted with one or more F, Cl, Br, or I, wherein alkyl is defined above.

The term "heteroaryl", as used herein, refers to an aromatic radical of 5-18 ring atoms (i.e., a 5- to 18-membered heteroaryl), containing one or more heteroatoms independently selected from nitrogen, oxygen, and sulfur. A heteroaryl group can be monocyclic or polycyclic, e.g. a monocyclic heteroaryl ring fused to one or more carbocyclic aromatic groups or other monocyclic heteroaryl groups. The heteroaryl groups of this invention can also include ring systems substituted with one or more oxo moieties. In one aspect, heteroaryl has from 5-15 ring atoms (i.e., 5- to 15-membered heteroaryl), such as a 5- to 12-membered ring (i.e, a 5- to 12-membered heteroaryl). In certain instances, heteroaryl is a 5-membered heteroaryl and in other instances heteroaryl is a 6-membered heteroaryl. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. The foregoing heteroaryl groups may be C-attached or N-attached (where such is possible). For instance, a group derived from pyrrole may be pyrrol-1-yl (N-attached) or pyrrol-3-yl (C-attached).

The present disclosure relates to a device for detecting an analyte, comprising a base, and a plurality of microneedles attached to the base, wherein: each microneedle has an outer surface; and the outer surface of at least one microneedle is coated with a composition comprising at least one polymer and least one first Peptide Nucleic Acid (PNA).

In some embodiments, the composition further comprises at least one second PNA, wherein the second PNA is different from the first PNA.

In some embodiments, the polymer is hydrophilic. In some embodiments, the polymer is alginate, xanthan, dextran, hyaluronic acid, poly(vinylalcohol) (PVA), polymethacrylic acid (PMAA), polyacrylic acid (PAA), poly(N-vinylpyrrolidone) (PVP), poly(lactic-co-glycolic acid) (PLGA), poly(N-isopropylacrylamide), poly(ethylene glycol) (PEG), poly(propylene oxide) (PPO), poly(ethylene glycol) diacrylate/dimethacrylate (PEGDA/PEGDMA), or poly(ethylene glycol) acrylate/methacrylate (PEGA/PEGMA), or a combination thereof. In some embodiments, the polymer is alginate.

In some embodiments, the polymer is covalently attached to the first PNA, optionally by a linker. In some embodiments, the polymer is covalently attached to the second PNA, optionally by a linker. In some embodiments, the linker is selected from ⁀—OC(=O)—⁀, ⁀—(O=)CO—⁀, ⁀—NH—C(=O)— ⁀, ⁀—C(=O)NH—⁀, ⁀—O—⁀, ⁀—NH—C(=O)—NH-⁀, or ⁀—S—⁀, wherein ⁀ indicates a point of attachment of the linker to the polymer, to the first PNA, or to the second PNA. In some embodiments, the linker is represented by structural formula (I) or (Ia),

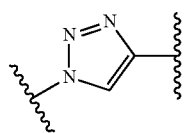
(I)

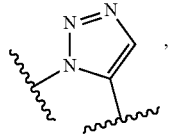
(Ia)

wherein ⁀ indicates a point of attachment of the linker to the polymer, to the first PNA, or to the second PNA In some embodiments, the linker is cleavable. In some embodiments, the linker is photocleavable. In some embodiments, the linker is a photocleavable linker represented by structural formula (II) or (IIa),

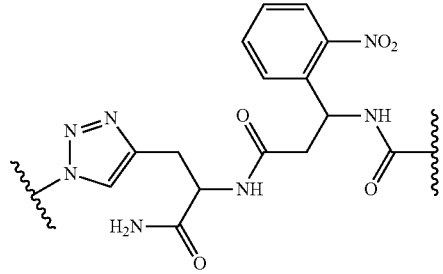
(II)

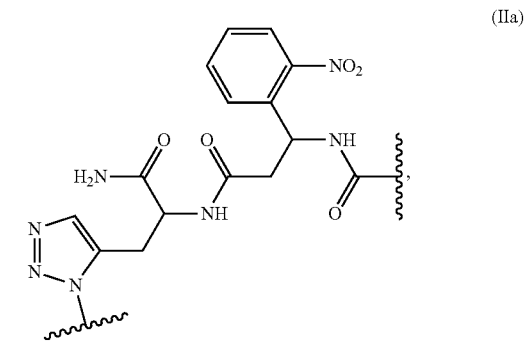
(IIa)

wherein ⁀ indicates a point of attachment of the linker to the polymer, to the first PNA, or to the second PNA.

In some embodiments, the first PNA comprises from 5 to 30 nucleobases. In some embodiments, the first PNA comprises from 5 to 8 nucleobases. In some embodiments, the second PNA comprises from 5 to 8 nucleobases.

In some embodiments, the PNA comprises a modified peptide backbone. For example, the PNA is a γ-PNA, an aegPNA, or an acpcPNA.

In some embodiments, the analyte is a nucleic acid; the first PNA is complementary to the 5' end of the nucleic acid; and the second PNA is complementary to the 3' end of the nucleic acid. In some embodiments, the is nucleic acid is microRNA.

In some embodiments, the first PNA is represented by the structural formula (III),
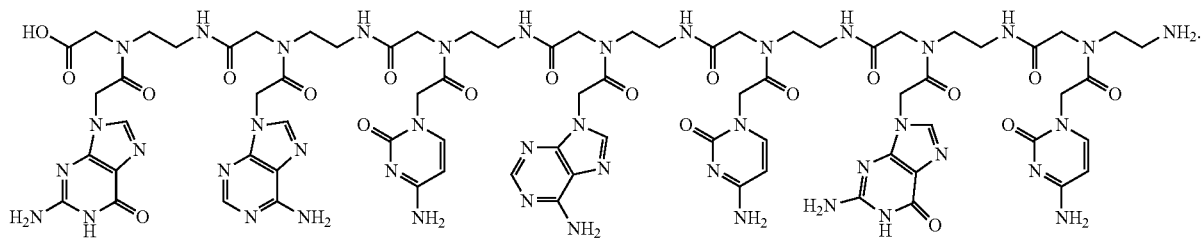
(III)
In some embodiments, the first PNA is represented by a structural formula selected from
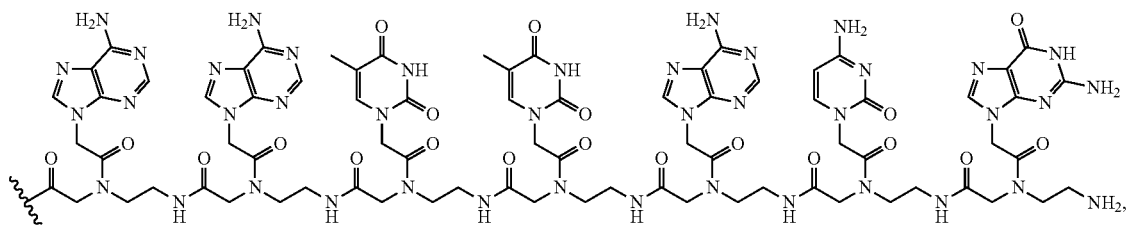
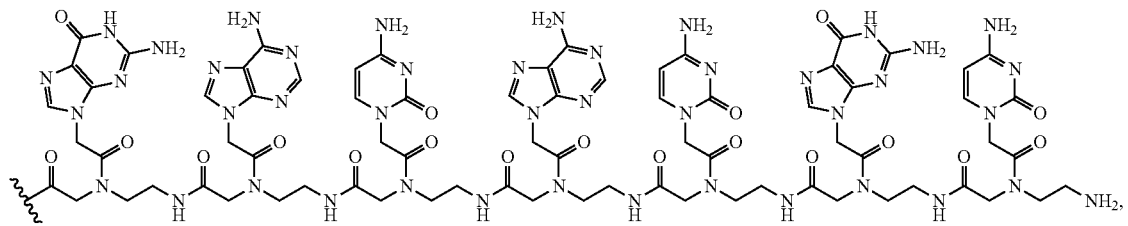
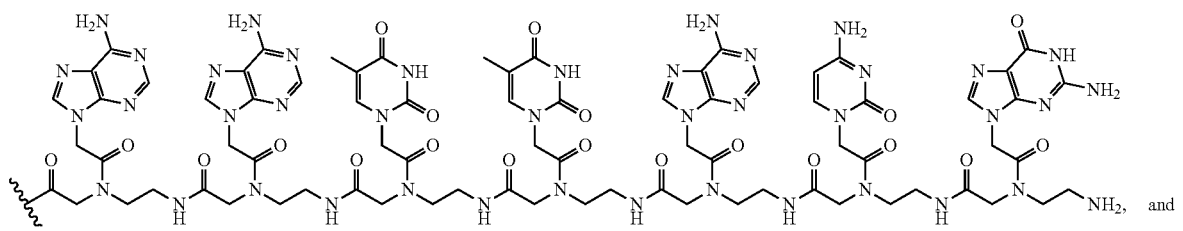
and
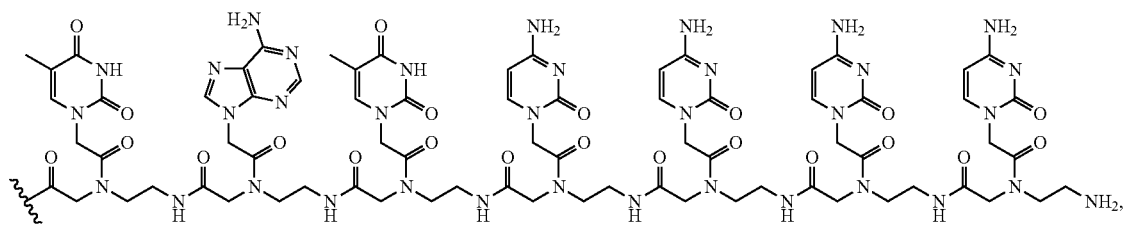

wherein ⌇ indicates a point of attachment of the first PNA to the linker.

In some embodiments, the first PNA is represented by a structural formula selected from

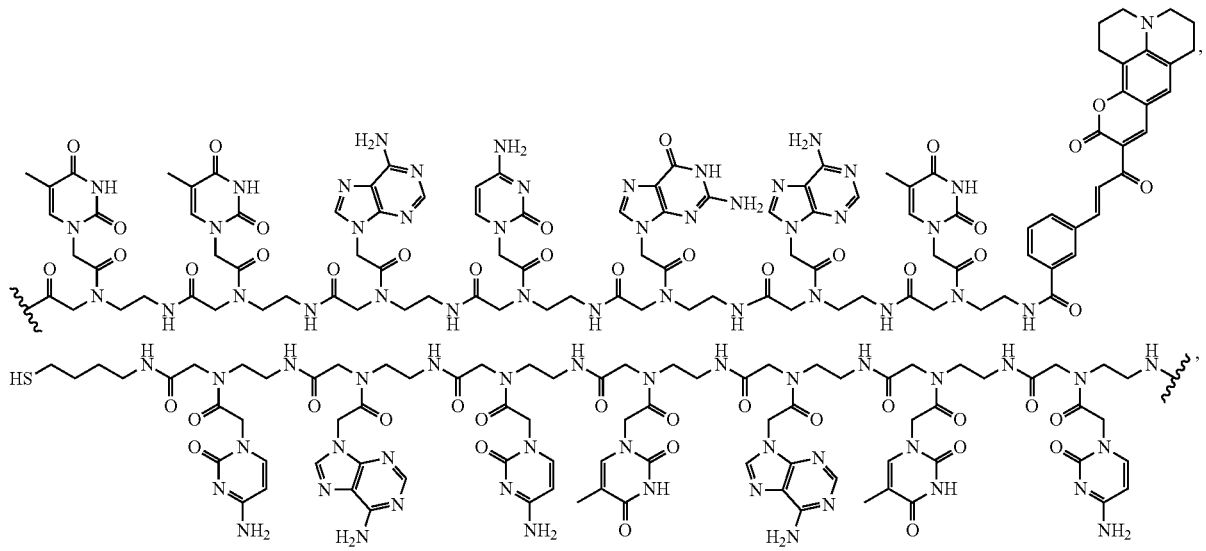

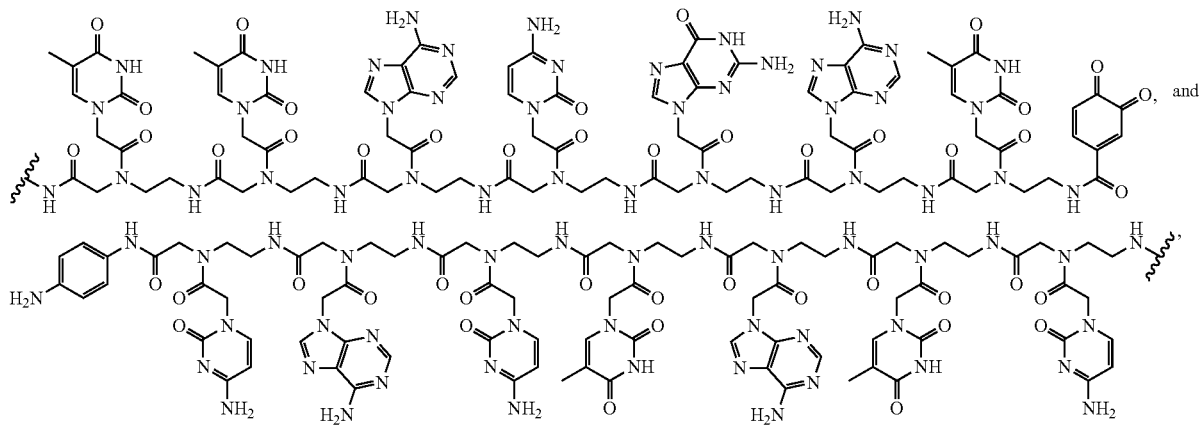

wherein ⌇ indicates a point of attachment of the first PNA to the linker.

In some embodiments, the first PNA comprises a first probe head; the second PNA comprises a second probe head; and the first probe head and the second probe head selectively bind each other, thereby producing a detectable signal. In some embodiments, the first probe head comprises a chemical moiety selected from the group consisting of

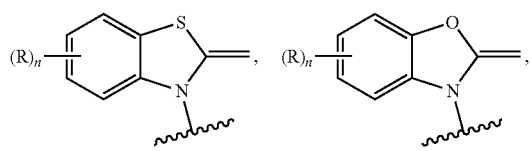

-continued

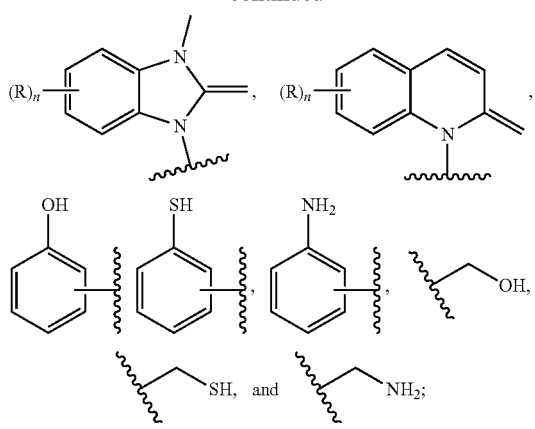

and
the second probe head comprises a chemical moiety selected from the group consisting of

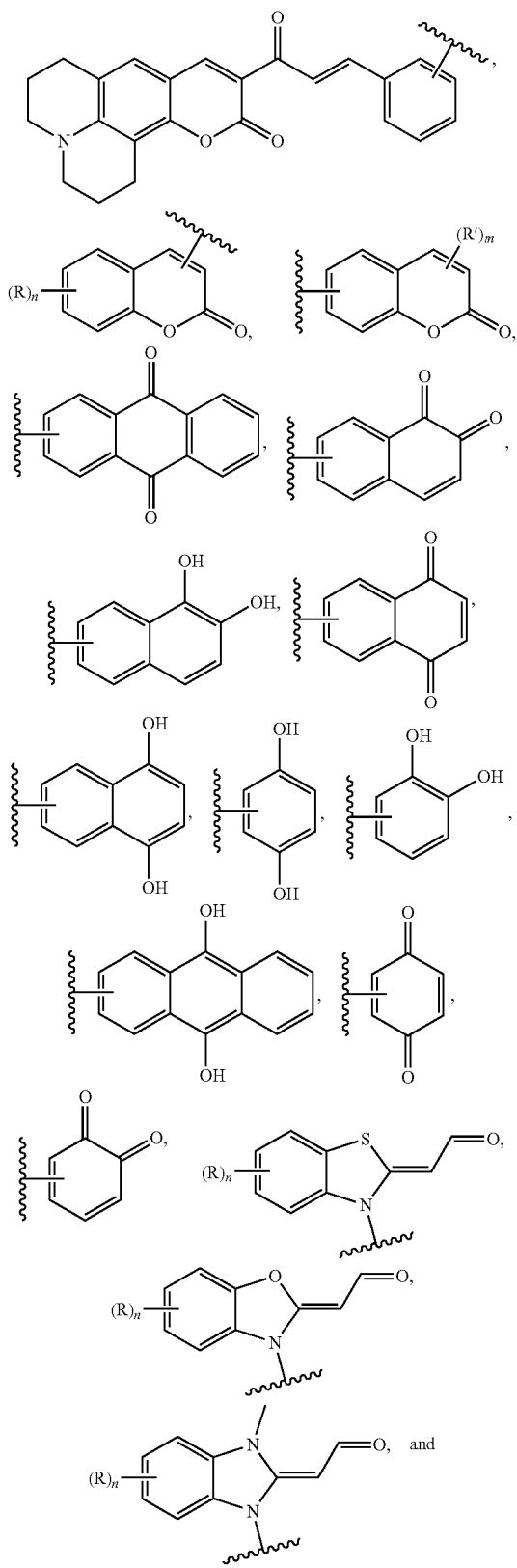

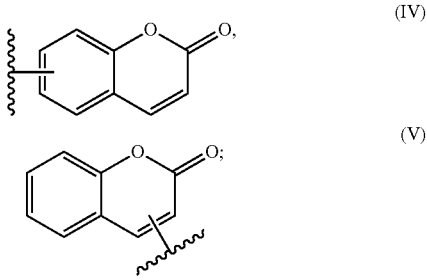

wherein:
each R or R' is independently selected from Halogen, —NO$_2$, —OH, —NH$_2$, —NH(C$_{1-6}$ alkyl), —N(C$_{1-6}$ alkyl)$_2$, —NCS, C$_{1-6}$ alkyl, C$_{1-6}$ haloalkyl, C$_{6-10}$ aryl, 5- to 12-membered heteroaryl, —O(C$_{1-6}$ alkyl), —C(O)O(C$_{1-6}$ alkyl), —OC(O)(C$_{1-6}$ alkyl), —C(O)NH$_2$, —C(O)NH(C$_{1-6}$ alkyl), —C(O)N(C$_{1-6}$ alkyl)$_2$, —NHC(O)(C$_{1-6}$ alkyl), —N(C$_{1-6}$ alkyl)C(O)(C$_{1-6}$ alkyl), —SO$_2$(C$_{1-6}$ alkyl), —SO$_2$(C$_{6-10}$ aryl), and —SO$_3^+$X$^+$;
X$^+$ is Li$^+$, Na$^+$, K$^+$, or N(C$_{1-6}$ alkyl)$_4^+$;
m is 0 to 2; and
n is 0 to 4.

In some embodiments, the first probe head comprises a thiol and the second probe head comprises a chemical moiety represented by the structural formula (IV) or structural formula (V):

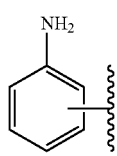 (IV)

(V)

or the first probe head comprises a chemical moiety represented by the following structural formula and the second probe head comprises a chemical moiety represented by the following structural formula

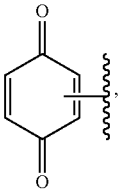

wherein ⸹ indicates a point of attachment of the chemical moiety to the first PNA or to the second PNA.

In some embodiments, the first PNA is a hairpin PNA comprising a third probe head; and further wherein the third probe head produces a detectable signal upon the hairpin PNA binding to the analyte.

In some embodiments, the third probe head comprises a chemical moiety selected from the group consisting of

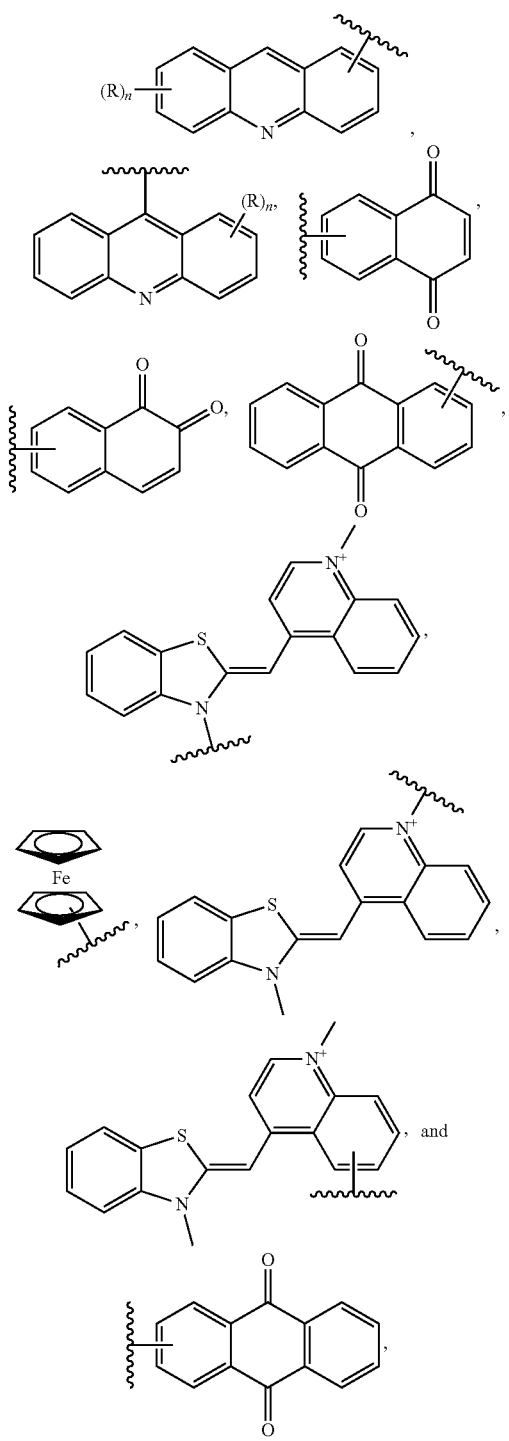

wherein:

⸹ is a point of attachment of the chemical moiety to the first PNA or to the second PNA;

each R or R' is independently selected from Halogen, —$NO_2$, —OH, —$NH_2$, —NH($C_{1-6}$ alkyl), —N($C_{1-6}$ alkyl)$_2$, —NCS, $C_{1-6}$ alkyl, $C_{1-6}$ haloalkyl, $C_{6-10}$ aryl, 5- to 12-membered heteroaryl, —O($C_{1-6}$ alkyl), —C(O)O($C_{1-6}$ alkyl), —OC(O)($C_{1-6}$ alkyl), —C(O)$NH_2$, —C(O)NH($C_{1-6}$ alkyl), —C(O)N($C_{1-6}$ alkyl)$_2$, —NHC(O)($C_{1-6}$ alkyl), —N($C_{1-6}$ alkyl)C(O)($C_{1-6}$ alkyl), —$SO_2$($C_{1-6}$ alkyl), —$SO_2$($C_{6-10}$ aryl), and —$SO_3^+X^+$;

$X^+$ is $Li^+$, $Na^+$, $K^+$, or N($C_{1-6}$ alkyl)$_4^+$; and n is 0 to 4.

In some embodiments, the detectable signal is fluorescent signal. In some embodiments, the detectable signal is electrochemical signal.

The present disclosure relates to a method of detecting an analyte in interstitial fluid (ISF) of a subject, comprising: contacting the subject with the device of the disclosure, exposing the device to the ISF of the subject; detaching the device from the subject; and measuring an intensity of the detectable signal.

The present disclosure relates to a method of detecting an analyte in ISF of a subject, comprising: contacting the subject with the device of the disclosure, and exposing the device to the ISF of the subject.

In some embodiments, the method further comprises detaching the device from the subject.

In some embodiments, the method further comprises contacting the device with a first detection reagent, wherein the first detection reagent binds the analyte and to produce a first signal. In some embodiments, the first signal is a fluorescence, absorbance, or electrical signal.

In some embodiments, the method further comprises determining a concentration of the analyte in ISF of the subject. In some embodiments, the method further comprises measuring an intensity of the first signal, thereby determining the concentration of the analyte.

In some embodiments, the first detection reagent is selected from a fluorogenic reagent or a DNA intercalator. In some embodiments, the first detection reagent is selected from SYBR-Safe, SYBR-green, SYBR-red, YOYO-1, YOYO-3, TOTO-1, TOTO-3, TOPO-1, TOPO-3, POPO-1, POPO-3, Thiazole orange, or Ethidium bromide.

In some embodiments, the analyte forms an analyte:PNA complex with the first PNA and with the second PNA, if present.

In some embodiments, the linker is photocleavable, and the method further comprises exposing the device to electromagnetic radiation, thereby releasing a free PNA:analyte complex. In some embodiments, the method further comprises contacting the free PNA:analyte complex with a second detection agent, wherein the second detection agent binds to the free PNA:analyte complex and produce a second signal. In some embodiments, the second signal is a fluorescence, absorbance, or electrical signal.

In some embodiments, the method further comprises determining the concentration of the free PNA:analyte complex. In some embodiments, the method further comprises measuring an intensity of the second signal, thereby determining the concentration of the free PNA:analyte complex.

In some embodiments, the second detection reagent is selected from a fluorogenic reagent or a DNA intercalator. In some embodiments, the second detection reagent is selected from SYBR-Safe, SYBR-green, SYBR-red, YOYO-1, YOYO-3, TOTO-1, TOTO-3, TOPO-1, TOPO-3, POPO-1, POPO-3, Thiazole orange, Ethidium bromide, molecular beacon, Taqman probe, or Lexicon probe.

In certain embodiments, the first detection agent and the second detection agent are the same. Alternatively, the first detection agent and the second detection agent are different.

In certain embodiments, only the first detection agent is used. In other embodiments, only the second detection agent is used.

In some embodiments, both the first detection agent and the second detection agent are used.

The present disclosure relates to a method of detecting an analyte in interstitial fluid (ISF) of a subject, comprising: contacting the subject with the device of the disclosure; exposing the device to the ISF of the subject; detaching the device from the subject; eluting the analyte from the device; and exposing the analyte to a detection agent, wherein the detection agent binds to the analyte. In some embodiments, the detection reagent is selected from a fluorogenic reagent, a DNA intercalator, or a third PNA. In some embodiments, the detection reagent is a third PNA.

In some embodiments, eluting the analyte comprises exposing the analyte to a solution comprising at least one salt, for example, to an aqueous solution comprising at least one salt. For example, the salt is selected from KCl, NaCl, LiCl, $K_3PO_4$, $Na_3PO_4$, $Li_3PO_4$, $MgCl_2$, $CaCl_2$), or sodium dodecyl sulfate.

In some embodiments, the method further comprises determining a concentration of the analyte.

In some embodiments, contacting the subject comprises contacting a skin surface of the subject.

In some embodiments, the subject is a human subject.

In some embodiments, the analyte is a nucleic acid. In some embodiments, the analyte is RNA. In some embodiments, the analyte is microRNA. In some embodiments, the analyte is DNA. In some embodiments, first PNA is complementary to the 5' end of the nucleic acid, and the second PNA is complementary to the 3' end of the nucleic acid.

In some embodiments, the analyte comprises a biomarker for a disease selected from cancer or infection. In some embodiments, the infection is bacterial infection, viral infection, viroid infection, parasite infection, protozoa infection, or fungal infection.

In various embodiments the present invention is
1. A device, comprising a base, and a plurality of microneedles attached to the base, wherein:
   each microneedle has an outer surface; and
   the outer surface of at least one microneedle is coated with a composition comprising at least one polymer and least one Peptide Nucleic Acid (PNA).
2. The device of claim 1, wherein the polymer is hydrophilic.
3. The device of claim 1 or 2, wherein the polymer is alginate, xanthan, dextran, hyaluronic acid, poly(vinylalcohol) (PVA), polymethacrylic acid (PMAA), polyacrylic acid (PAA), poly(N-vinylpyrrolidone) (PVP), poly(lactic-co-glycolic acid) (PLGA), poly(N-isopropylacrylamide), poly(ethylene glycol) (PEG), poly(propylene oxide) (PPO), poly(ethylene glycol) diacrylate/dimethacrylate (PEGDA/PEGDMA), or poly(ethylene glycol) acrylate/methacrylate (PEGA/PEGMA), or a combination thereof.
4. The device of any one of claims 1-3, wherein the polymer is alginate.
5. The device of any one of claims 1-4, wherein at least one polymer is covalently attached to at least one PNA, optionally by a linker.
6. The device of claim 5, wherein the linker is selected from

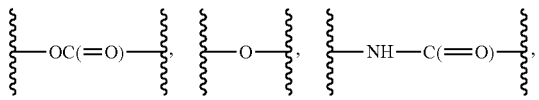

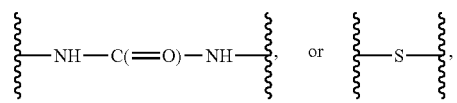

wherein ⸹ indicates a point of attachment of the linker to the polymer or to the PNA.

7. The device of claim 5, wherein the linker is represented by structural formula (I),

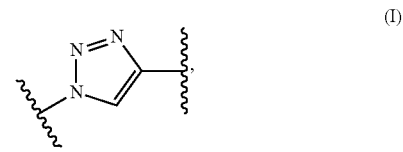 [SMILES: *c1cn(*)nn1]

wherein ⸹ indicates a point of attachment of the linker to the polymer or to the PNA.

8. The device of claim 5, wherein the linker cleavable.
9. The device of claim 8, wherein the linker is a photocleavable linker represented by structural formula (II),

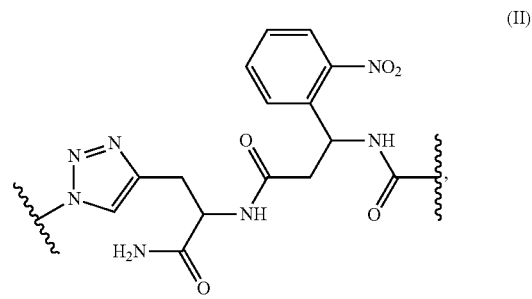 [SMILES: *C(=O)NC(CC(=O)NC(Cc1cn(*)nn1)C(N)=O)c1ccccc1[N+](=O)[O-]]

wherein ⸹ indicates a point of attachment of the linker to the polymer or to the PNA.

10. The device of any one of claims 1-9, wherein the PNA comprises from 5 to 30 nucleobases.
11. The device of any one of claims 1-10, wherein the nucleobases are selected from adenine, thymine, guanine, cytosine, or uracil.
12. The device of any one of claims 1-11, wherein the PNA is represented by the structural formula (III),

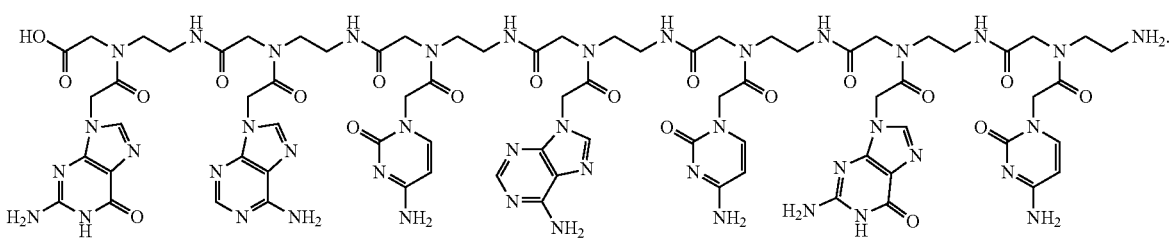

(III)

13. A method of detecting an analyte in interstitial fluid (ISF) of a subject, comprising:
    contacting the subject with the device of any one of claims 1-12, and
    exposing the device to the ISF of the subject.
14. The method of claim 13, further comprising detaching the device from the subject.
15. The method of claim 13 or 14, further comprising contacting the device with a first detection reagent, wherein the first detection reagent is adapted to bind to the analyte and to produce a first signal.
16. The method of claim 15, wherein the first signal is a fluorescence, absorbance, or electrical signal.
17. The method of any one of claims 13-16, further comprising determining a concentration of the analyte in ISF of the subject.
18. The method of claim 17, further comprising measuring an intensity of the first signal, thereby determining the concentration of the analyte.
19. The method of any one of claims 15-18, wherein the first detection reagent is selected from a fluorogenic reagent or a DNA intercalator.
20. The method of any one of claims 15-18, wherein the first detection reagent is selected from SYBR-Safe, SYBR-green, SYBR-red, YOYO-1, YOYO-3, TOTO-1, TOTO-3, TOPO-1, TOPO-3, POPO-1, POPO-3, Thiazole orange, or Ethidium bromide.
21. The method of any one of claims 13-20, wherein the analyte and at least one PNA form an analyte:PNA complex.
22. The method of claim 21, wherein the linker is photocleavable, further comprising exposing the device to electromagnetic radiation, thereby releasing a free PNA:analyte complex.
23. The method of claim 22, further comprising contacting the free PNA:analyte complex with a second detection agent, wherein the second detection agent is adapted to bind to the free PNA:analyte complex and produce a second signal.
24. The method of claim 23, wherein the second signal is a fluorescence, absorbance, or electrical signal.
25. The method of claim 23 or 24, further comprising determining the concentration of the free PNA:analyte complex.
26. The method claim 25, further comprising measuring an intensity of the second signal, thereby determining the concentration of the free PNA:analyte complex.
27. The method of any one of claims 23-26, wherein the second detection reagent is selected from a fluorogenic reagent or a DNA intercalator.
28. The method of claim 23-26, wherein the second detection reagent is selected from SYBR-Safe, SYBR-green, SYBR-red, YOYO-1, YOYO-3, TOTO-1, TOTO-3, TOPO-1, TOPO-3, POPO-1, POPO-3, Thiazole orange, Ethidium bromide, molecular beacon, Taqman probe, or Lexicon probe.
29. A method of detecting an analyte in interstitial fluid (ISF) of a subject, comprising:
    contacting the subject with the device of any one of claims 1-12;
    exposing the device to the ISF of the subject;
    detaching the device from the subject;
    eluting the analyte from the device;
    exposing the analyte to a detection agent, wherein the detection agent c the analyte.
30. The method of claim 29, wherein the detection reagent is selected from a fluorogenic reagent, a DNA intercalator, or a PNA.
31. The method of claim 29 or 30, wherein the detection reagent is a PNA.
32. The method of any one of claims 29-31, further comprising determining a concentration of the analyte.
33. The method of any one of claims 13-32, wherein contacting the subject comprises contacting a skin surface of the subject.
34. The method of any one of claims 13-33, wherein the subject is a human subject.
35. The method of any one of claims 13-34, wherein the analyte is a nucleic acid.
36. The method of any one of claims 13-35, wherein the analyte is RNA.
37. The method of any one of claims 13-36, wherein the analyte is microRNA.
38. The method of any one of claims 13-34, wherein the analyte is DNA.
39. The method of any one of claims 13-38, wherein the analyte comprises a biomarker for a disease selected from cancer or infection.
40. The method of claim 39, wherein the infection is bacterial infection, viral infection, viroid infection, parasite infection, protozoa infection, or fungal infection.

EXAMPLES

Preparation of Hydrogel-Coated Microneedles:

Poly-L-Lactide (PLLA; RESOMER L 207 S, Evonik Industries AG) MNs were prepared as previously reported. The dimensions of the MN patch can be seen in the diagram shown in FIG. 4. It is noteworthy that the height of the MN patch, which is 0.55 mm or 550 microns, was designed to allow the needles to penetrate the epidermis layer (100-200 microns) and reach the underlying dermis layer, containing a rich source of IF. The bare MNs were functionalized with an engineered hydrogel coating via a three-step coating procedure based on a protocol developed by Mandal et al. (A. Mandal, A. V. Boopathy, L. K. W. Lam, K. D. Moynihan, M. E. Welch, N. R. Bennett, M. E. Turvey, N. Thai, J. H. Van, J. C. Love, P. T. Hammond, D. J. Irvine, Sci. Transl. Med. 2018, 10, eaar2227). Firstly, 50 μL of a 0.01 wt % solution of positively-charged poly-L-lysine (Sigma-Aldrich, P4832) was pipetted onto each MN to facilitate electrostatic adhesion of the alginate to the MN patch. The solution was removed after 30 min, and the MNs were left to dry under a fume hood at RT for at least 1 h. Secondly, 60 μL of alginate solution, composed of 0.35 mg alginate-PNA and 1.4 mg sucrose (Sigma) in 60 μL ddH$_2$O, was pipetted onto each MN array. The MNs were then left to dry under a fume hood at RT for at least 3 h. Finally, 50 μL of crosslinking solution, composed of 20 mM CaCl$_2$) (Sigma), was pipetted onto each MN, after which the coated arrays were left to dry at RT overnight (>12 h).

MN Sampling Protocol:

To visualize the captured DNA after MN sampling, fluorescently-labeled (Alexa-647, unless otherwise indicated) single stranded target DNA-210 (as a proxy for miRNA-210) and non-target DNA-141 (as a proxy for miR-141) were purchased from Invitrogen. For sampling, single MN patches were placed tips-down into individual wells of a clear 48-well microplate (Corning, half-area) filled with 100 μL of analyte solution. The solution consisted of either water/buffer (control), target DNA-210 or non-target DNA-141 at concentrations indicated for each experiment. After sampling at 37° C. for 15 min (unless otherwise indicated), the MNs were removed, washed thoroughly with ddH$_2$0 (10 min, 3 washes) then imaged by a fluorescence scanner (Typhoon FLA 9500, PMT 300V, 25 μm pixel resolution, λex=635 nm unless otherwise indicated).

In another detection method, MNs were dipped into solutions (100 μL) containing various amounts of unlabeled DNA-210 (0-500 nM). After 15 min sampling, the MNs were washed thoroughly with water and dipped into a solution of SYBR-safe for 10 minutes. The MNs were then imaged with a fluorescence scanner (Typhoon FLA9500, GE Healthcare).

Images were analyzed by Fiji (Image J) software to quantify fluorescence intensity.

MN Release Protocol:

To release or recover captured NA after sampling, MN patches were placed tips-down into individual wells of a clear 48-well microplate (Corning, half-area) filled with 100 μL of ddH$_2$0. Next, the plate was inserted into a UV-crosslinker (BLX-315 crosslinker, 315 nm, Consort) and irradiated with amounts of UV energy as indicated by each experiment to break off the PNA:DNA complex. After 1 h of shaking (250 RPM, RT), the MNs were removed from the wells, rinsed and dried overnight. In the case when DNA was labelled with Alexa-647 dye, the MNs were imaged after release to show loss of fluorescence, equivalent to release of DNA (Typhoon FLA 9500, PMT 300V, 25 μm pixel resolution, λex=635 nm). In the case when DNA was unlabeled, thiazole orange (TO, 2 μM) was added to the solution in each well and kept for 30 min before imaging with a plate reader (Omega, λex=488 nm, λem=520 nm, gain=1000).

Characterization of Hydrogel Swelling Properties:

To estimate the amount of water that is absorbed by the hydrogel coating, a swelling study was performed and monitored over time. MNs were prepared as outlined previously. After preparing the MNs, the MNs were weighed once dry to provide the initial dry mass. MNs were then placed into wells of a 48-well microplate containing 100 μL of phosphate buffered saline (PBS, pH 7.4), and left to swell at 37° C. At designated time points, MNs were removed, dabbed gently to remove excess water droplets then weighed to provide the swollen mass. Masses were recorded for 20 min when no further changes in mass were observed.

Preparation of Human Skin Samples:

Human abdominal skin with adipose tissue was purchased from Caltag medsystems (Buckingham, U.K.). The sample was washed in Dulbecco's minimal essential medium (DMEM; Gibco Life Technologies) supplemented with 2% Antimycotic-Antibiotic (ABAM; Gibco Life Technologies) for 30 min. Then, it was moved to DMEM supplemented with 1% ABAM for the rest of the procedure. Using sterile surgical scissors, subcutaneous fat was removed in order to obtain only the epidermis with the dermis. A series of 8 mm$^2$ area punches were made using a biopsy punch (Stiefel) to create nine skin samples (N=3 replicates per condition) for the following MN sampling experiment.

MN Application to Human Skin:

MNs were pressed onto human skin samples by a gentle thumb press. After 15 min at 37° C., MNs were gently removed. To show penetration, skin was stained with trypan blue (0.4% diluted in half by ddH$_2$O, sterile-filtered, Sigma, T8154). After 10 min, skin samples were rinsed thoroughly then imaged by a wide field microscope under bright field illumination to show a characteristic MN penetration pattern.

MN Sampling from Skin:

Just before sampling with MNs, skin samples were removed from the culture media (DMEM with 1% ABAM) then washed thoroughly with ddH$_2$O (three times). To load the skin with DNA, the samples were gently transferred to 48-well microplates and placed on top of 100 μL solutions containing either: ddH$_2$O (control), 500 nM non-target DNA-141, or 500 nM target DNA-210, where both DNA fragments were labelled with Alexa-647 dye (N=3 samples per condition). Skin samples were left to incubate on the solutions overnight in the fridge. On the next day, the samples were carefully removed from the incubation solutions with sterile tweezers, rinsed thoroughly with ddH$_2$O, then placed in a 48-well microplate.

For the MN sampling experiment, single MN patches were gently pressed onto each skin sample by a gentle thumb press, and the MNs were left to sample at 37° C. for 15 min. Next, the MNs were gently removed from the skin, rinsed thoroughly (ddH$_2$O, three times) and left to dry overnight before being imaged with a fluorescence scanner (Typhoon FLA 9500, PMT 400V, 25 μm pixel resolution, λex=635 nm, Cy 5 setting). A second experiment was conducted exactly as the first described above but wherein skin samples were left to incubate on a solution containing a mixture of DNA: target DNA-210 tagged with Alexa-647 and non-target DNA-141 tagged with fluorescein, both at 500 nM. The rest of the experiment was prepared as outlined above but the MNs were imaged after sampling at two wavelengths: 635 nm (Cy 5 setting) to image the target DNA-210 and 473 nm (Cy 2 setting) to image the non-target DNA-141.

It is important to note that when incubating the skin samples in the solutions containing fluorescently-labelled DNA, the samples were floating on the surface with the bottom dermis layer of the skin in contact with the solution. Molecules from the solution could not cross the intact and highly impermeable stratum corneum from the top. Thus, after sampling the skin with MNs, any fluorescence signal detected on the MN originated from molecules which have diffused from solution through the dermis and into the epidermis.

Synthesis of PNA Targeting miR-210 by Solid Phase Peptide Synthesis:

PNA probe directed against miR-210 was designed to contain an alkyne group (C-terminus) for ease of functionalization to the alginate hydrogel as well as a photosensitive group for ease of release by UV irradiation after sampling. The 7-mer PNA oligomer was synthesized via standard Solid Phase Peptide Synthesis (SPPS) exploiting the chemistry of 9-fluoromethoxycarbonyl (Fmoc) protecting groups as previously described (D. Al Sulaiman, J. Y. H. Chang, S. Ladame, *Angew. Chem. Int. Ed.* 2017, 56, 5247-5251; G. A. D. Metcalf, A. Shibakawa, H. Patel, A. Sita-Lumsden, A. Zivi, N. Rama, C. L. Bevan, S. Ladame, *Anal. Chem.* 2016, 88, 8091-8098).

Functionalization of Alginate with Azide by EDC/NHS Chemistry:

Alginate was functionalized with azide groups via peptide bond formation following a protocol adapted from Breger et al. (FIG. 5) (J. C. Breger, B. Fisher, R. Samy, S. Pollack, N. S. Wang, I. Isayeva, *J. Biomed. Mat. Res. B Appl. Biomat.* 2015, 103, 1120-1132). Briefly, a 1 wt % solution of alginate was prepared by dissolving 500 mg of alginate (low viscosity alginate from brown algae, Sigma) in 50 mL of MES buffer (50 mM, pH 4.0). To this solution, the following was added sequentially: 20 mM N-ethyl-N'-(3-dimethylaminopropyl) carbodiimide hydrochloride (EDC.HCl, Sigma), 140 mM N-hydroxysuccinimide (NHS, Sigma), and 1.8 mL of 11-azido -3,6,9-trioxaundecan-1-amine (AA, SelectLab 134179-38-7). The reaction was set at RT overnight with constant stirring. The reaction solution was next dialyzed (MWCO 12 kDa) against aqueous NaCl for 1 day then against ddH$_2$O for three days. Finally, the purified product was lyophilized to produce a white product, which was characterized by $^1$H-NMR (D$_2$O, 400 MHz, 363 K).

Synthesis of Alginate-PNA by Click Chemistry:

Alginate-azide was functionalized with PNA-alkyne via a copper-catalyzed azide-alkyne cycloaddition reaction (Click chemistry) as adapted from Presolski et al. (S. I. Presolski, V. P. Hong, M. G. Finn, *Curr. Protoc. Chem. Biol.* 2011, 3, 153-162). Briefly, a 1 wt % solution of alginate-azide was prepared in 100 mM phosphate buffer (pH=7.4). To this solution, PNA-alkyne was added at an amount equivalent to 1 mol % (i.e. 8.1 mg PNA-alkyne per 100 mg alginate-azide). Next, copper (II) sulphate (CuSO$_4$, Sigma) and the ligand Tris[(1-benzyl-1H-1,2,3-triazol-4-yl)methyl]amine (TBTA, Sigma) were mixed together then added to the reaction solution to produce a final concentration of 0.1 mM CuSO$_4$ and 0.5 mM TBTA. Finally, sodium ascorbate (Sigma) was added to the solution at a final concentration of 5 mM. The reaction vessel was then sealed and left to react at RT overnight. After 24 h, the reaction solution was diluted 5 times, and the reaction was left to proceed for a further 24 h. To chelate and remove copper (II) ions from the solution, 10 mM Ethylenediaminetetraacetic acid (EDTA, Sigma) was added before the entire solution was dialyzed against ddH$_2$O for three days, lyophilized, and characterized by $^1$H-NMR (D$_2$O, 400 MHz, 363 K).

$^1$H-NMR Characterization of Hydrogels:

All three hydrogel samples (unmodified Alginate, Alginate-azide and Alginate-PNA) were characterized by $^1$H-NMR following the same protocol. Briefly, each sample was dissolved in deuterated water (D$_2$O) to produce a 5 mg/mL solution. For improved peak resolution and separation, NMR characterization was performed at 363 K (400 MHz or 500 MHz). Firstly, the G fraction (FG) of the unmodified alginate was characterized by analysis of the NMR peaks according to established protocols and the following Equation (1), Equation (2), and Equation (3) (H. M. Jensen, F. H. Larsen, S. B. Engelsen, *Methods Mol. Biol.* 2015, 1308, 347-363).

$$F_G = \frac{G}{M + G} \quad \text{Equation (1)}$$

$$G = \frac{1}{2}\left[I_A + I_C + \frac{1}{2}(I_{B1} + I_{B2} + I_{B3})\right] \quad \text{Equation (2)}$$

$$M = I_{B4} + \frac{1}{2}(I_{B1} + I_{B2} + I_{B3}) \quad \text{Equation (3)}$$

Peaks A, B, and C were first identified and integrated to produce $I_A$ ($\delta$=5.72 ppm), $I_B$ ($\delta$=5.3 ppm) and $I_C$ ($\delta$=5.1 ppm) (FIG. 8). From these, the G fraction, which is the fraction of G subunits compared to the total G and M subunits, was determined to be 44 mol %.

Figure 9:
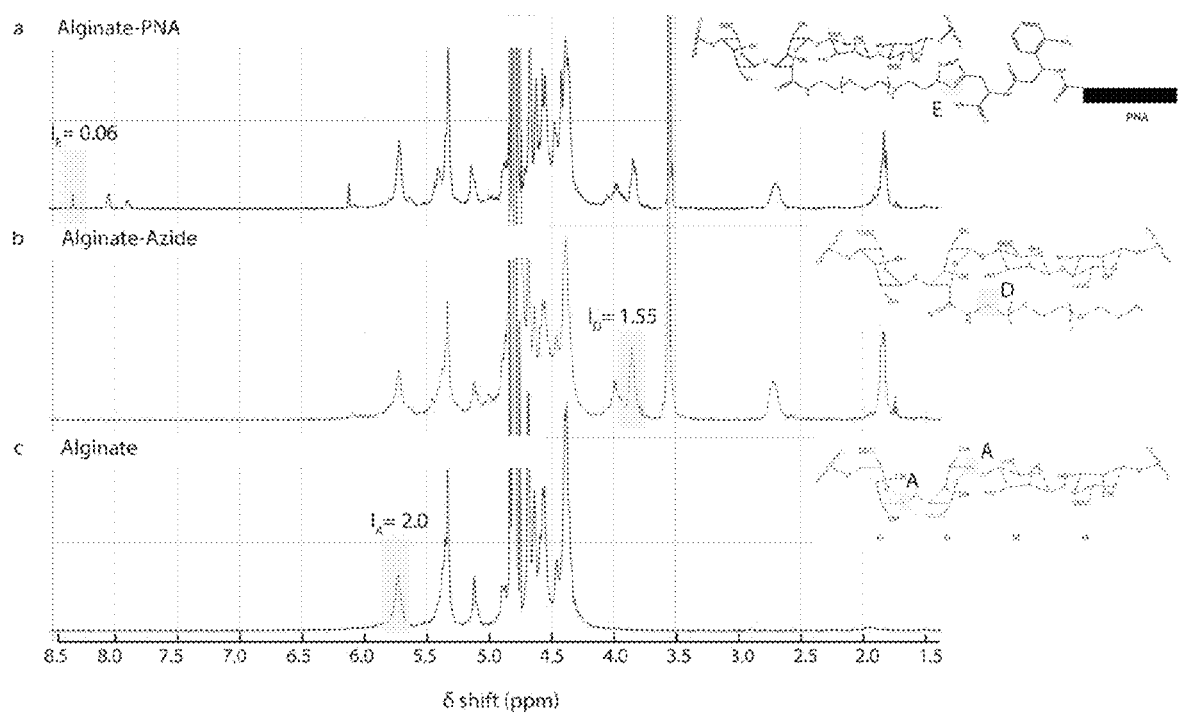
FIG. 9. $^1$H-NMR spectra of the engineered alginate hydrogels (D$_2$O, 363 K, 400-500 MHz) showing (c) unmodified alginate; (b) alginate-azide; and the final alginate-PNA (a) with equivalent chemical structures shown on the right, highlighting the characteristic peaks and equivalent proton(s) on the structure.

Next, the NMR spectrum of Alginate-azide was analyzed to characterize the amount of azide functionalization. The triplet at $\delta$=3.85 ppm was attributed to the two protons next to the peptide bond between AA and the alginate fiber, labelled D. Comparing the ratio of ID to $2\times I_A$ and multiplying by FG produced a 17 mol % functionalization. Finally, the amount of PNA modification on alginate-PNA was determined by comparing the integral of the peak at $\delta$=8.34 ppm ($I_E$), attributed to the proton on the imidazole product of the cycloaddition reaction, and $I_A$ (FIG. 9*c*). Multiplying this by FG produced a 1 mol % functionalization.

Physical Morphology by Scanning Electron Microscopy:

An SEM study was conducted to evaluate and compare the physical morphologies of the unmodified alginate and alginate-PNA coatings. Images were taken using a ZEISS Sigma 300 instrument (EHT 5.00 kV). Samples were prepared as outlined in the methods Section 'Preparation of Hydrogel-coated Microneedles'. In this case, MNs were coated with either alginate-PNA or unmodified alginate then lyophilized and attached onto a metal support using double-sided carbon tape. The samples were then coated with a 10 nm chromium or gold coating using a sputtering coater before being imaged by SEM. Different magnifications were taken as outlined on the micrographs.

Surface Topography by Atomic Force Microscopy:

Atomic force microscopy (AFM) (Asylum MFP-3D) was used to visualize the surface topography of the alginate-PNA film used to coat the MN patches. PPP-NCHR probes (NANOSENSORS™, Windsor Scientific) with resonance frequency of 330 kHz and tips with <7 nm radius were used. Images were taken in ambient air at room temperature in standard tapping mode (AC). Multiple scans were taken at different zones on the sample surface to ensure images are representative of the entire surface state. Furthermore, scan areas were varied from 50×50 µm' down to 1×1 µm$^2$. Gwyddion and MatLab software were used for image analysis. Freshly prepared alginate-PNA samples were deposited on a glass slide for ease of imaging by AFM. No further lyophilization or coating steps were required.

Validation of PNA:DNA complex Release:

Four MNs were prepared and used to sample 500 nM of fluorescently-labelled target DNA, as previously described. After confirming capture by a fluorescence scanner (control), the MNs were placed tips-down into 100 µL of water and irradiated with 0 (control), 1, 2, or 4 J/cm$^2$ of UV energy (BLX-315, 315 nm) to break off the PNA-DNA complex. After 1 h of shaking (250 RPM, RT), the MNs were rinsed, dried overnight, then imaged by a fluorescence scanner (Typhoon FLA 9500, PMT 300V, 25 µm pixel resolution, $\lambda_{ex}$=635 nm) (FIG. 12a). The fluorescence intensity of the UV irradiated MNs was over 70% lower than that of the non-irradiated MNs (FIG. 12b). Assuming no photobleaching of the DNA label (Alexa-647) by the UV light (315 nm), this decrease in fluorescence indicated that 1 J/cm² of energy (~1 min irradiation) can release over 70% of captured DNA.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A device for detecting an analyte, comprising a base, and a plurality of microneedles attached to the base, wherein:
    each microneedle has an outer surface; and
    the outer surface of at least one microneedle is coated with a composition comprising at least one polymer and at least one first Peptide Nucleic Acid (PNA),
        wherein the polymer is covalently attached to the first PNA, by a first linker, wherein the first linker is a photocleavable linker represented by structural formula (II) or (IIa),

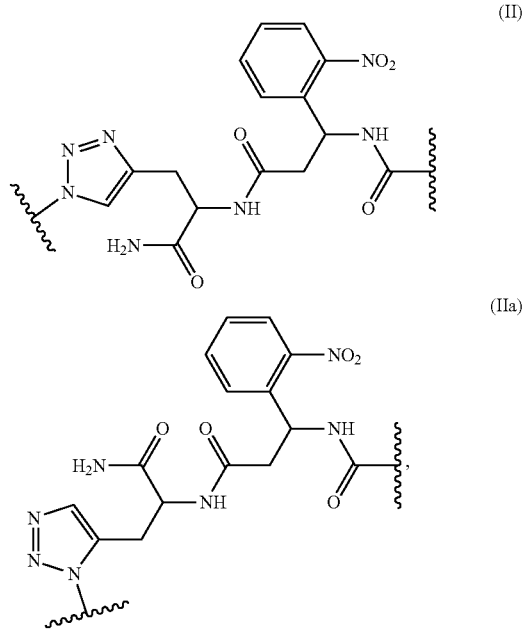

wherein ⧼ indicates a point of attachment of the first linker to the polymer or to the first PNA.

2. The device of claim 1, wherein the composition further comprises at least one second PNA, wherein the second PNA is different from the first PNA.

3. The device of claim 1, wherein the polymer is hydrophilic.

4. The device of claim 1, wherein the polymer is alginate, xanthan, dextran, hyaluronic acid, poly(vinylalcohol) (PVA), polymethacrylic acid (PMAA), polyacrylic acid (PAA), poly(N-vinylpyrrolidone) (PVP), poly(lactic-co-glycolic acid) (PLGA), poly(N-isopropylacrylamide), poly(ethylene glycol) (PEG), poly(propylene oxide) (PPO), poly(ethylene glycol) diacrylate/dimethacrylate (PEGDA/PEGDMA), or poly(ethylene glycol) acrylate/methacrylate (PEGA/PEGMA), or a combination thereof.

5. The device of claim 1, wherein the polymer is alginate.

6. The device of claim 2, wherein the polymer is covalently attached to the second PNA, optionally by a second linker.

7. The device of claim 6, wherein the second linker is represented by structural formula (I) or (Ia),

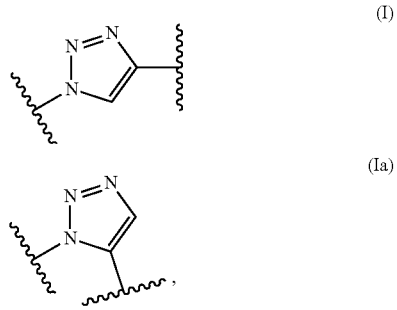

wherein ⧼ indicates a point of attachment of the linker to the polymer, to the first PNA, or to the second PNA.

8. The device of claim 6, wherein the second linker is cleavable.

9. The device of claim 8, wherein the second linker is a photocleavable linker represented by structural formula (II) or (IIa),

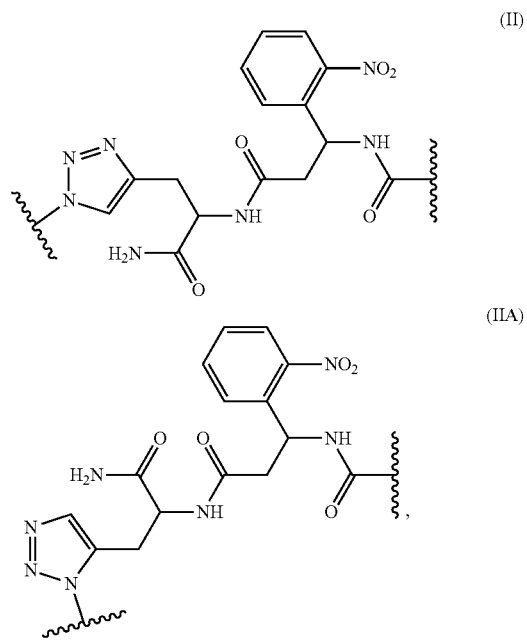

wherein ⧼ indicates a point of attachment of the linker to the polymer or to the second PNA.

10. The device of claim 1, wherein the first PNA comprises from 5 to 30 nucleobases.

11. The device of claim 1, wherein the first PNA comprises from 5 to 8 nucleobases.

12. The device of claim 2, wherein the second PNA comprises from 5 to 8 nucleobases.

13. The device of claim 2, wherein:
the analyte is a nucleic acid;
the first PNA is complementary to the 5' end of the nucleic acid; and
the second PNA is complementary to the 3' end of the nucleic acid.

14. The device of claim 1, wherein the analyte is microRNA.

15. The device of claim 1, wherein the first PNA is represented by a structural formula selected from

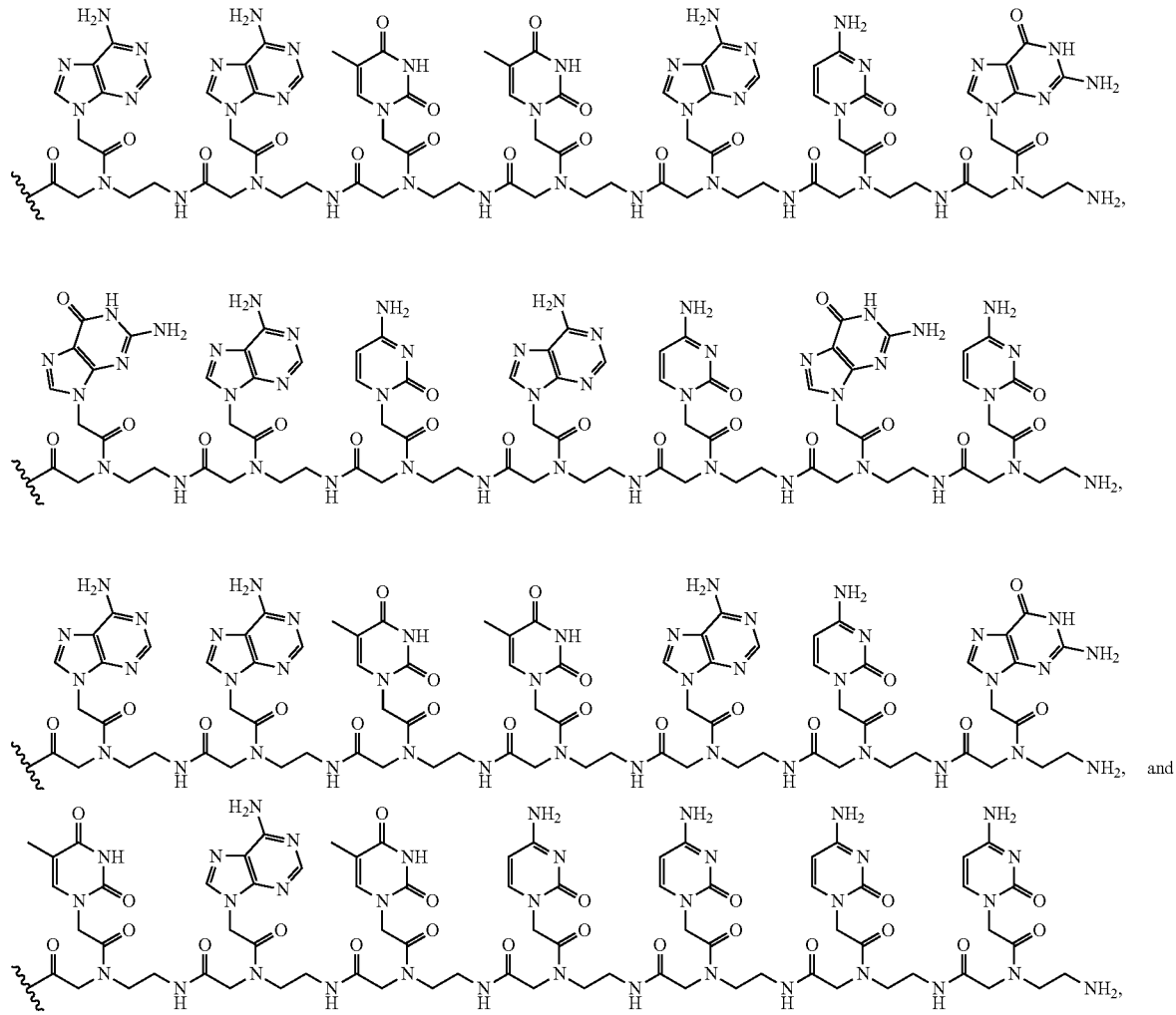

wherein ⸹ indicates a point of attachment of the first PNA to the linker.

16. The device of claim 6, wherein:
the first PNA comprises a first probe head;
the second PNA comprises a second probe head; and
the first probe head and the second probe head selectively bind each other, thereby producing a detectable signal.

17. The device of claim 16, wherein the first probe head comprises a chemical moiety selected from the group consisting of

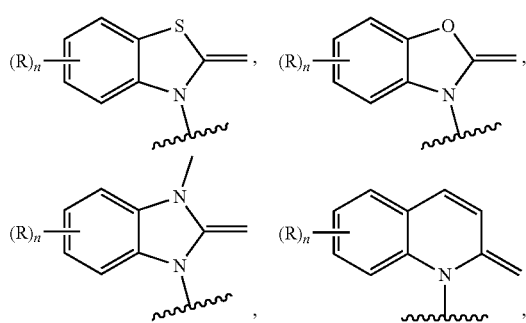

-continued

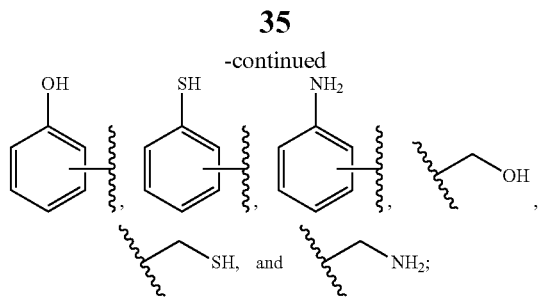

and the second probe head comprises a chemical moiety selected from the group consisting of

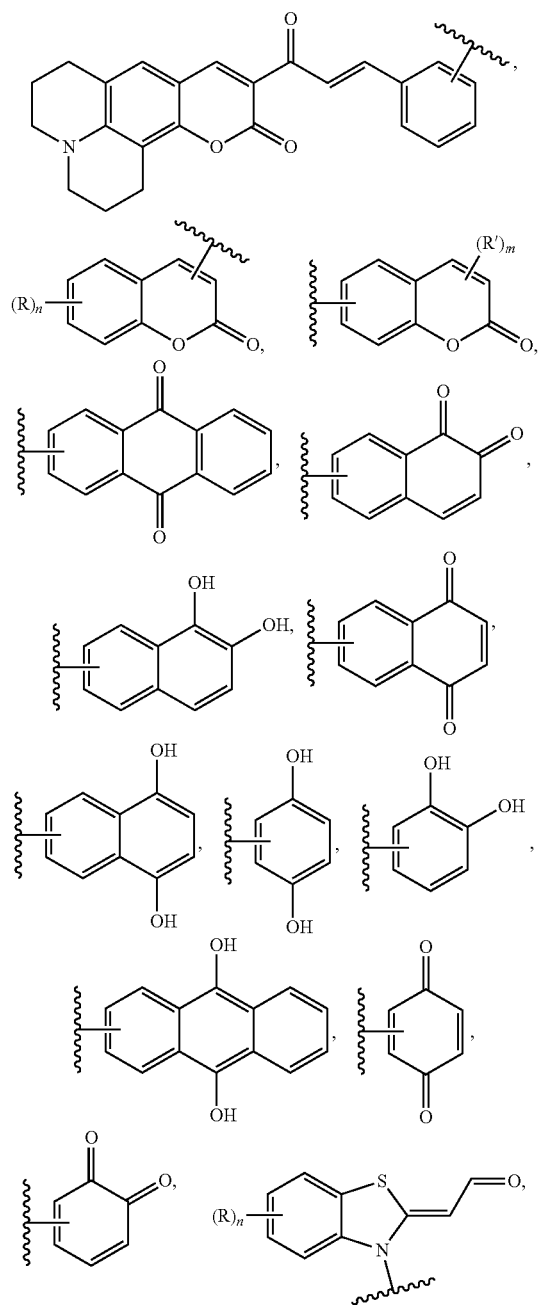

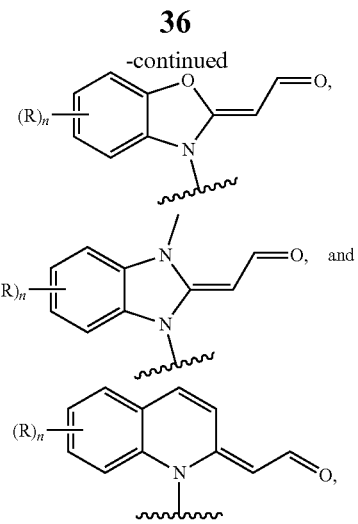

wherein:

⸹ is a point of attachment of the chemical moiety to the first PNA or to the second PNA;

each R or R' is independently selected from Halogen, —NO$_2$, —OH, —NH$_2$, —NH(C$_{1-6}$ alkyl), —N(C$_{1-6}$ alkyl)$_2$, —NCS, C$_{1-6}$ alkyl, C$_{1-6}$ haloalkyl, C$_{6-10}$ aryl, 5- to 12-membered heteroaryl, —O(C$_{1-6}$ alkyl), —C(O)O (C$_{1-6}$ alkyl), —OC(O)(C$_{1-6}$ alkyl), —C(O)NH$_2$, —C(O)NH(C$_{1-6}$ alkyl), —C(O)N(C$_{1-6}$ alkyl)$_2$, —NHC (O)(C$_{1-6}$ alkyl), —N(C$_{1-6}$ alkyl)C(O)(C$_{1-6}$ alkyl), —SO$_2$(C$_{1-6}$ alkyl), —SO$_2$(C$_{6-10}$ aryl), and —SO$_3^-$X$^+$;

X$^+$ is Li$^+$, Na$^+$, K$^+$, or N(C$_{1-6}$ alkyl)$_4^+$;

m is 0 to 2; and n is 0 to 4.

18. The device of claim 16, wherein:

the first probe head comprises a thiol and the second probe head comprises a chemical moiety represented by the structural formula (IV) or structural formula (V):

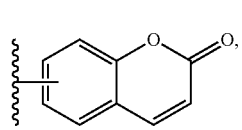 (IV)

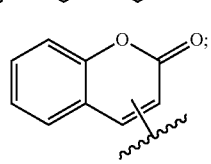 (V)

or the first probe head comprises a chemical moiety represented by the following structural formula

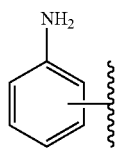

and the second probe head comprises a chemical moiety represented by the following structural formula

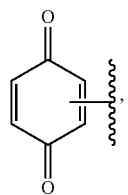

wherein ⸽ indicates a point of attachment of the chemical moiety to the first PNA or to the second PNA.

19. The device of claim 16, wherein the first PNA is represented by a structural formula selected from

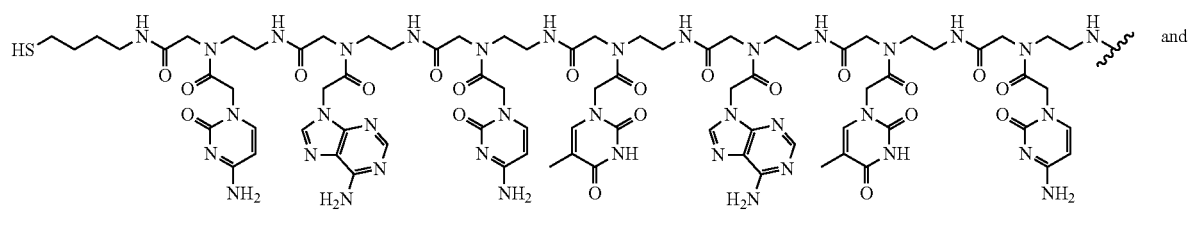

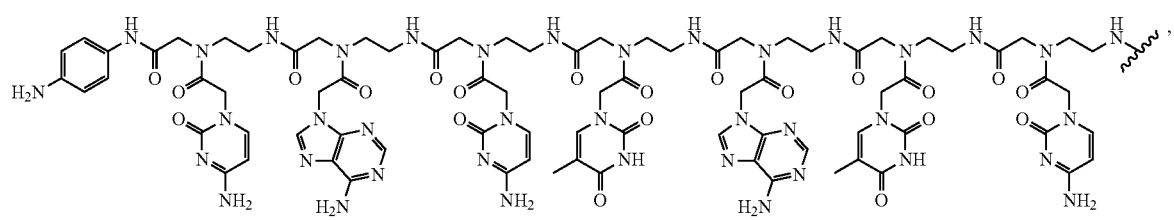

wherein ⸽ indicates a point of attachment of the first PNA to the first linker.

20. The device of claim 16, wherein the second PNA is represented by a structural formula selected from

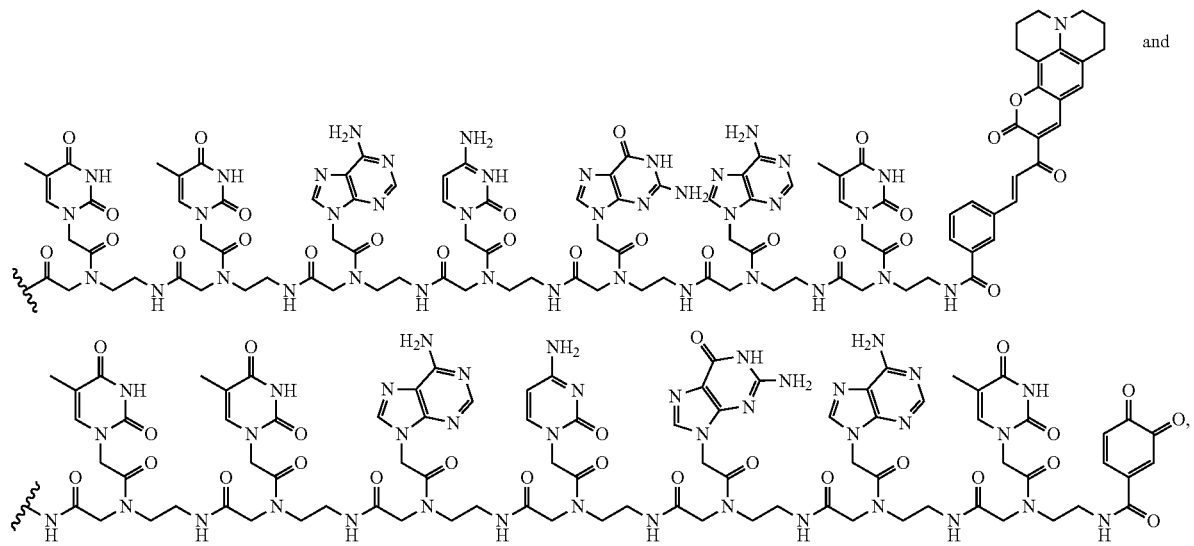

wherein ⸹ indicates a point of attachment of the second PNA to the second linker.

21. The device of claim 16, wherein the first PNA is a hairpin PNA comprising a third probe head; and further wherein the third probe head produces a detectable signal upon the hairpin PNA binding to the analyte.

22. The device of claim 21, wherein the third probe head comprises a chemical moiety selected from the group consisting of

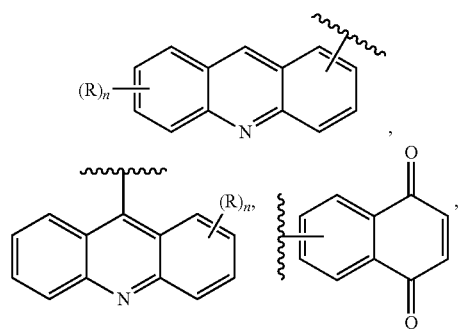

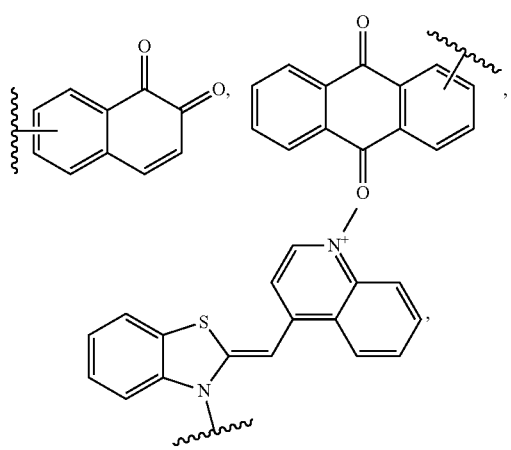

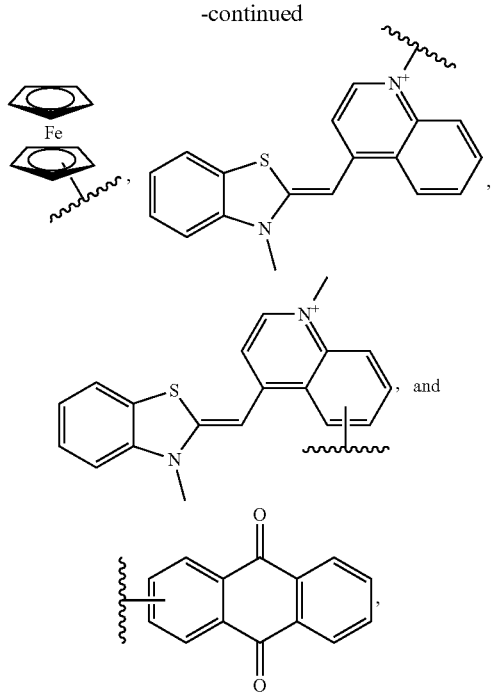

wherein:

⸹ is a point of attachment of the chemical moiety to the first PNA or to the second PNA;

each R or R' is independently selected from Halogen, $-NO_2$, $-OH$, $-NH_2$, $-NH(C_{1-6}$ alkyl), $-N(C_{1-6}$ alkyl)$_2$, $-NCS$, $C_{1-6}$ alkyl, $C_{1-6}$ haloalkyl, $C_{6-10}$ aryl, 5- to 12-membered heteroaryl, $-O(C_{1-6}$ alkyl), $-C(O)O(C_{1-6}$ alkyl), $-OC(O)(C_{1-6}$ alkyl), $-C(O)NH_2$, $-C(O)NH(C_{1-6}$ alkyl), $-C(O)N(C_{1-6}$ alkyl)$_2$, $-NHC(O)(C_{1-6}$ alkyl), $-N(C_{1-6}$ alkyl)$C(O)(C_{1-6}$ alkyl), $-SO_2(C_{1-6}$ alkyl), $-SO_2(C_{6-10}$ aryl), and $-SO_3^-X^+$;

$X^+$ is $Li^+$, $Na^+$, $K^+$, or $N(C_{1-6}$ alkyl)$_4^+$; and n is 0 to 4.

23. The device of claim 16, wherein the detectable signal is fluorescent signal.

24. The device of claim 16, wherein the detectable signal is electrochemical signal.

* * * * *